(12) United States Patent
Jones

(10) Patent No.: US 11,965,175 B2
(45) Date of Patent: Apr. 23, 2024

(54) CELL EXPANSION

(71) Applicant: Terumo BCT, Inc., Lakewood, CO (US)

(72) Inventor: Mark E. Jones, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 985 days.

(21) Appl. No.: 16/302,951

(22) PCT Filed: May 25, 2017

(86) PCT No.: PCT/US2017/034544
§ 371 (c)(1),
(2) Date: Nov. 19, 2018

(87) PCT Pub. No.: WO2017/205667
PCT Pub. Date: Nov. 30, 2017

(65) Prior Publication Data
US 2019/0119628 A1    Apr. 25, 2019

Related U.S. Application Data

(60) Provisional application No. 62/341,523, filed on May 25, 2016.

(51) Int. Cl.
| C12N 5/00 | (2006.01) |
| A61K 35/15 | (2015.01) |
| C12M 1/10 | (2006.01) |
| C12M 1/12 | (2006.01) |
| C12M 3/00 | (2006.01) |
| C12N 5/0789 | (2010.01) |

(52) U.S. Cl.
CPC ............ *C12N 5/0068* (2013.01); *A61K 35/15* (2013.01); *C12M 1/10* (2013.01); *C12M 3/00* (2013.01); *C12M 25/10* (2013.01); *C12N 5/0647* (2013.01); *C12N 2502/1358* (2013.01)

(58) Field of Classification Search
CPC .............. C12N 5/0068; C12N 5/0647; C12N 2502/1358; A61K 35/15; C12M 1/10; C12M 3/00; C12M 25/10
See application file for complete search history.

(56) References Cited

U.S. PATENT DOCUMENTS

| 2,997,077 A | 8/1961 | Rodrigues |
| 3,013,435 A | 12/1961 | Rodrigues |
| 3,067,915 A | 12/1962 | Shapiro et al. |
| 3,191,807 A | 6/1965 | Rodrigues |
| 3,283,727 A | 11/1966 | Rodrigues |
| 3,701,717 A | 10/1972 | Ingvorsen |
| 3,821,087 A | 6/1974 | Knazek et al. |
| 3,896,061 A | 7/1975 | Tanzawa et al. |
| 4,173,415 A | 11/1979 | Wyatt |
| 4,301,010 A | 11/1981 | Eddleman et al. |
| 4,301,118 A | 11/1981 | Eddleman et al. |
| 4,391,912 A | 7/1983 | Yoshida et al. |
| 4,412,990 A | 11/1983 | Lundblad et al. |
| 4,418,691 A | 12/1983 | Yannas et al. |
| 4,439,322 A | 3/1984 | Sonoda et al. |
| 4,439,901 A | 4/1984 | Eddleman |
| 4,440,853 A | 4/1984 | Michaels et al. |
| 4,478,829 A | 10/1984 | Landaburu et al. |
| 4,486,188 A | 12/1984 | Altshuler et al. |
| 4,509,695 A | 4/1985 | Bessman |
| 4,585,654 A | 4/1986 | Landaburu et al. |
| 4,618,586 A | 10/1986 | Walker et al. |
| 4,629,686 A | 12/1986 | Gruenberg |
| 4,647,539 A | 3/1987 | Bach |
| 4,650,766 A | 3/1987 | Harm et al. |
| 4,670,544 A | 6/1987 | Schwinn et al. |
| 4,722,902 A | 2/1988 | Harm et al. |
| 4,727,059 A | 2/1988 | Binder et al. |
| 4,789,658 A | 12/1988 | Yoshimoto et al. |
| 4,804,628 A | 2/1989 | Cracauer et al. |
| 4,828,706 A | 5/1989 | Eddleman |
| 4,885,087 A | 12/1989 | Kopf |
| 4,889,812 A | 12/1989 | Guinn et al. |
| 4,894,342 A | 1/1990 | Guinn et al. |
| 4,897,358 A | 1/1990 | Carrasco |
| 4,910,139 A | 3/1990 | Chang et al. |
| 4,918,019 A | 4/1990 | Guinn |
| 4,960,521 A | 10/1990 | Keller |
| 4,973,558 A | 11/1990 | Wilson et al. |
| 4,988,623 A | 1/1991 | Schwarz et al. |
| 5,015,585 A | 5/1991 | Robinson |
| 5,019,054 A | 5/1991 | Clement et al. |
| 5,079,168 A | 1/1992 | Amiot |
| 5,081,035 A | 1/1992 | Halberstadt |
| 5,126,238 A | 6/1992 | Gebhard et al. |
| 5,130,141 A | 7/1992 | Law et al. |
| 5,149,544 A | 9/1992 | Gentile et al. |

(Continued)

FOREIGN PATENT DOCUMENTS

| CA | 1016332 A | 8/1977 |
| CN | 102406926 A | 4/2012 |

(Continued)

OTHER PUBLICATIONS

Housler et al. "Compartmental hollow fiber capillary membrane-based bioreactor technology for in vitro studies on red blood cell lineage direction of hematopoietic stem cells", Tissue Engineering, Part C: Methods, 18:2 133-142 (Year: 2011).*

(Continued)

*Primary Examiner* — Laura Schuberg
*Assistant Examiner* — Joseph Paul Miano
(74) *Attorney, Agent, or Firm* — Harness, Dickey & Pierce, P.L.C.

(57) ABSTRACT

Embodiments are described that relate to methods and systems for growing cells in a hollow fiber bioreactor. In embodiments, the cells may be exposed to a number of growth factors including a combination of recombinant growth factors. In other embodiments, the cells may be grown in co-culture with other cells, e.g., hMSC's. In embodiments, the cells may include CD34+ cells.

8 Claims, 15 Drawing Sheets

(56) References Cited

U.S. PATENT DOCUMENTS

| | | |
|---|---|---|
| 5,156,844 A | 10/1992 | Aebischer et al. |
| 5,162,225 A | 11/1992 | Sager et al. |
| 5,169,930 A | 12/1992 | Ruoslahti et al. |
| 5,192,553 A | 3/1993 | Boyse et al. |
| 5,197,985 A | 3/1993 | Caplan et al. |
| 5,202,254 A | 4/1993 | Amiot et al. |
| 5,225,346 A | 7/1993 | Matsumiya et al. |
| 5,226,914 A | 7/1993 | Caplan et al. |
| 5,240,614 A | 8/1993 | Ofsthun et al. |
| 5,240,861 A | 8/1993 | Bieri |
| 5,252,216 A | 10/1993 | Folena-Wasserman et al. |
| 5,283,058 A | 2/1994 | Faustman |
| 5,310,676 A | 5/1994 | Johansson et al. |
| 5,324,428 A | 6/1994 | Flaherty |
| 5,330,915 A | 7/1994 | Wilson et al. |
| 5,342,752 A | 8/1994 | Platz et al. |
| 5,399,493 A | 3/1995 | Emerson et al. |
| 5,416,022 A | 5/1995 | Amiot |
| 5,422,197 A | 6/1995 | Zito |
| 5,436,151 A | 7/1995 | McGlave et al. |
| 5,437,994 A | 8/1995 | Emerson et al. |
| 5,439,757 A | 8/1995 | Zito |
| 5,459,069 A | 10/1995 | Palsson et al. |
| 5,460,964 A | 10/1995 | McGlave et al. |
| H1509 H | 12/1995 | Eran et al. |
| 5,478,739 A | 12/1995 | Slivka et al. |
| 5,486,359 A | 1/1996 | Caplan et al. |
| 5,496,659 A | 3/1996 | Zito |
| 5,507,949 A | 4/1996 | Ho |
| 5,510,257 A | 4/1996 | Sirkar et al. |
| 5,512,180 A | 4/1996 | Ho |
| 5,527,467 A | 6/1996 | Ofsthun et al. |
| 5,541,105 A | 7/1996 | Melink et al. |
| 5,543,316 A | 8/1996 | Zawadzka et al. |
| 5,545,492 A | 8/1996 | Zito |
| 5,549,674 A | 8/1996 | Humes et al. |
| 5,571,720 A | 11/1996 | Grandics et al. |
| 5,581,687 A | 12/1996 | Lyle et al. |
| 5,591,625 A | 1/1997 | Gerson et al. |
| 5,593,580 A | 1/1997 | Kopf |
| 5,595,909 A | 1/1997 | Hu et al. |
| 5,599,703 A | 2/1997 | Davis et al. |
| 5,605,822 A | 2/1997 | Emerson et al. |
| 5,605,829 A | 2/1997 | McGlave et al. |
| 5,605,835 A | 2/1997 | Hu et al. |
| 5,622,857 A | 4/1997 | Goffe |
| 5,626,731 A | 5/1997 | Cooley et al. |
| 5,627,070 A | 5/1997 | Gruenberg |
| 5,631,006 A | 5/1997 | Melink et al. |
| 5,635,386 A | 6/1997 | Palsson et al. |
| 5,635,387 A | 6/1997 | Fei et al. |
| 5,643,736 A | 7/1997 | Bruder et al. |
| 5,646,043 A | 7/1997 | Emerson et al. |
| 5,653,887 A | 8/1997 | Wahl et al. |
| 5,654,186 A | 8/1997 | Cerami et al. |
| 5,656,421 A | 8/1997 | Gebhard et al. |
| 5,658,995 A | 8/1997 | Kohn et al. |
| 5,667,985 A | 9/1997 | O'Leary et al. |
| 5,670,147 A | 9/1997 | Emerson et al. |
| 5,670,351 A | 9/1997 | Emerson et al. |
| 5,674,750 A | 10/1997 | Kraus et al. |
| 5,684,712 A | 11/1997 | Goffe et al. |
| 5,686,289 A | 11/1997 | Humes et al. |
| 5,688,687 A | 11/1997 | Palsson et al. |
| 5,695,989 A | 12/1997 | Kalamasz |
| 5,700,289 A | 12/1997 | Breitbart et al. |
| 5,705,534 A | 1/1998 | D'Agostino et al. |
| 5,707,859 A | 1/1998 | Miller et al. |
| 5,712,163 A | 1/1998 | Parenteau et al. |
| 5,728,581 A | 3/1998 | Schwartz et al. |
| 5,733,541 A | 3/1998 | Taichman et al. |
| 5,733,542 A | 3/1998 | Haynesworth et al. |
| 5,736,396 A | 4/1998 | Bruder et al. |
| 5,744,347 A | 4/1998 | Wagner et al. |
| 5,750,651 A | 5/1998 | Oppermann et al. |
| 5,753,506 A | 5/1998 | Johe |
| 5,763,194 A | 6/1998 | Slowiaczek et al. |
| 5,763,197 A | 6/1998 | Tsukamoto et al. |
| 5,763,261 A | 6/1998 | Gruenberg |
| 5,763,266 A | 6/1998 | Palsson et al. |
| 5,766,944 A | 6/1998 | Ruiz |
| 5,772,994 A | 6/1998 | Ildstad et al. |
| 5,783,075 A | 7/1998 | Eddleman et al. |
| 5,783,216 A | 7/1998 | Faustman |
| 5,785,912 A | 7/1998 | Cooley et al. |
| 5,804,446 A | 9/1998 | Cerami et al. |
| 5,806,529 A | 9/1998 | Reisner et al. |
| 5,807,686 A | 9/1998 | Wagner et al. |
| 5,811,094 A | 9/1998 | Caplan et al. |
| 5,811,397 A | 9/1998 | Francavilla et al. |
| 5,817,773 A | 10/1998 | Wilson et al. |
| 5,821,218 A | 10/1998 | Toback et al. |
| 5,827,735 A | 10/1998 | Young et al. |
| 5,827,740 A | 10/1998 | Pittenger |
| 5,830,921 A | 11/1998 | Cooley et al. |
| 5,833,979 A | 11/1998 | Schinstine et al. |
| 5,837,258 A | 11/1998 | Grotendorst |
| 5,837,539 A | 11/1998 | Caplan et al. |
| 5,840,502 A | 11/1998 | Van Vlasselaer |
| 5,840,576 A | 11/1998 | Schinstine et al. |
| 5,840,580 A | 11/1998 | Terstappen et al. |
| 5,842,477 A | 12/1998 | Naughton et al. |
| 5,843,633 A | 12/1998 | Yin et al. |
| 5,846,796 A | 12/1998 | Cerami et al. |
| 5,853,247 A | 12/1998 | Shroyer |
| 5,853,717 A | 12/1998 | Schinstine et al. |
| 5,855,608 A | 1/1999 | Brekke et al. |
| 5,855,613 A | 1/1999 | Antanavich et al. |
| 5,855,619 A | 1/1999 | Caplan et al. |
| 5,858,747 A | 1/1999 | Schinstine et al. |
| 5,858,782 A | 1/1999 | Long et al. |
| 5,861,315 A | 1/1999 | Nakahata |
| 5,866,115 A | 2/1999 | Kanz et al. |
| 5,866,420 A | 2/1999 | Talbot et al. |
| 5,868,930 A | 2/1999 | Kopf |
| 5,882,295 A | 3/1999 | Kope |
| 5,882,918 A | 3/1999 | Goffe |
| 5,882,929 A | 3/1999 | Fofonoff et al. |
| 5,888,807 A | 3/1999 | Palsson et al. |
| 5,902,741 A | 5/1999 | Purchio et al. |
| 5,906,827 A | 5/1999 | Khouri et al. |
| 5,906,934 A | 5/1999 | Grande et al. |
| 5,908,782 A | 6/1999 | Marshak et al. |
| 5,908,784 A | 6/1999 | Johnstone et al. |
| 5,912,177 A | 6/1999 | Turner et al. |
| 5,914,108 A | 6/1999 | Tsukamoto et al. |
| 5,922,597 A | 7/1999 | Verfaillie et al. |
| 5,922,847 A | 7/1999 | Broudy et al. |
| 5,925,567 A | 7/1999 | Kraus et al. |
| 5,928,945 A | 7/1999 | Seliktar et al. |
| 5,935,849 A | 8/1999 | Schinstine et al. |
| 5,938,929 A | 8/1999 | Shimagaki et al. |
| 5,939,323 A | 8/1999 | Valentini et al. |
| 5,942,225 A | 8/1999 | Bruder et al. |
| 5,955,353 A | 9/1999 | Amiot |
| 5,958,763 A | 9/1999 | Goffe |
| 5,965,436 A | 10/1999 | Thiede et al. |
| 5,972,703 A | 10/1999 | Long et al. |
| 5,980,795 A | 11/1999 | Klotzer et al. |
| 5,981,211 A | 11/1999 | Hu et al. |
| 5,981,708 A | 11/1999 | Lawman et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,001,643 A | 12/1999 | Spaulding |
| 6,001,647 A | 12/1999 | Peck et al. |
| 6,004,743 A | 12/1999 | Kenyon et al. |
| 6,010,696 A | 1/2000 | Caplan et al. |
| 6,015,554 A | 1/2000 | Galy |
| 6,022,540 A | 2/2000 | Bruder et al. |
| 6,022,742 A | 2/2000 | Kopf |
| 6,022,743 A | 2/2000 | Naughton et al. |
| 6,027,743 A | 2/2000 | Khouri et al. |

(56) References Cited

U.S. PATENT DOCUMENTS

| | | |
|---|---|---|
| 6,029,101 A | 2/2000 | Yoshida et al. |
| 6,030,836 A | 2/2000 | Thiede et al. |
| 6,040,180 A | 3/2000 | Johe |
| 6,045,818 A | 4/2000 | Cima et al. |
| 6,048,721 A | 4/2000 | Armstrong et al. |
| 6,048,727 A | 4/2000 | Kopf |
| 6,049,026 A | 4/2000 | Muschler |
| 6,054,121 A | 4/2000 | Cerami et al. |
| 6,060,270 A | 5/2000 | Humes |
| 6,066,317 A | 5/2000 | Yang et al. |
| 6,071,691 A | 6/2000 | Hoekstra et al. |
| 6,074,366 A | 6/2000 | Rogers et al. |
| 6,077,708 A | 6/2000 | Collins et al. |
| 6,082,364 A | 7/2000 | Balian et al. |
| 6,083,747 A | 7/2000 | Wong et al. |
| 6,086,643 A | 7/2000 | Clark et al. |
| 6,087,113 A | 7/2000 | Caplan et al. |
| 6,096,532 A | 8/2000 | Armstrong et al. |
| 6,096,537 A | 8/2000 | Chappel |
| 6,103,117 A | 8/2000 | Shimagaki et al. |
| 6,103,522 A | 8/2000 | Torok-Storb et al. |
| 6,110,176 A | 8/2000 | Shapira |
| 6,110,482 A | 8/2000 | Khouri et al. |
| 6,114,307 A | 9/2000 | Jaspers et al. |
| 6,117,985 A | 9/2000 | Thomas et al. |
| 6,120,491 A | 9/2000 | Kohn et al. |
| 6,127,141 A | 10/2000 | Kopf |
| 6,129,911 A | 10/2000 | Faris |
| 6,143,293 A | 11/2000 | Weiss et al. |
| 6,146,360 A | 11/2000 | Rogers et al. |
| 6,146,888 A | 11/2000 | Smith et al. |
| 6,149,902 A | 11/2000 | Artavanis-Tsakonas et al. |
| 6,149,906 A | 11/2000 | Mosca |
| 6,150,164 A | 11/2000 | Humes |
| 6,152,964 A | 11/2000 | Van Blitterswijk et al. |
| 6,162,643 A | 12/2000 | Wille, Jr. |
| 6,165,225 A | 12/2000 | Antanavich et al. |
| 6,165,785 A | 12/2000 | Ogle et al. |
| 6,174,333 B1 | 1/2001 | Kadiyala et al. |
| 6,174,526 B1 | 1/2001 | Cerami et al. |
| 6,174,666 B1 | 1/2001 | Pavlakis et al. |
| 6,179,871 B1 | 1/2001 | Halpern |
| 6,197,325 B1 | 3/2001 | MacPhee et al. |
| 6,197,575 B1 | 3/2001 | Griffith et al. |
| 6,200,606 B1 | 3/2001 | Peterson et al. |
| 6,214,369 B1 | 4/2001 | Grande et al. |
| 6,214,574 B1 | 4/2001 | Kopf |
| 6,224,860 B1 | 5/2001 | Brown |
| 6,225,119 B1 | 5/2001 | Qasba et al. |
| 6,225,368 B1 | 5/2001 | D'Agostino et al. |
| 6,228,117 B1 | 5/2001 | De Bruijn et al. |
| 6,228,607 B1 | 5/2001 | Kersten et al. |
| 6,228,635 B1 | 5/2001 | Armstrong et al. |
| 6,238,908 B1 | 5/2001 | Armstrong et al. |
| 6,239,157 B1 | 5/2001 | Mbalaviele |
| 6,242,252 B1 | 6/2001 | Reid et al. |
| 6,248,319 B1 | 6/2001 | Zsebo et al. |
| 6,248,587 B1 | 6/2001 | Rodgers et al. |
| 6,255,112 B1 | 7/2001 | Thiede et al. |
| 6,258,597 B1 | 7/2001 | Bachovchin et al. |
| 6,258,778 B1 | 7/2001 | Rodgers et al. |
| 6,261,549 B1 | 7/2001 | Fernandez et al. |
| 6,280,718 B1 | 8/2001 | Kaufman et al. |
| 6,280,724 B1 | 8/2001 | Moore |
| 6,281,012 B1 | 8/2001 | McIntosh et al. |
| 6,281,195 B1 | 8/2001 | Rueger et al. |
| 6,287,864 B1 | 9/2001 | Bagnis et al. |
| 6,291,249 B1 | 9/2001 | Mahant et al. |
| 6,297,213 B1 | 10/2001 | Oppermann et al. |
| 6,299,650 B1 | 10/2001 | Van Blitterswijk et al. |
| 6,306,424 B1 | 10/2001 | Vyakarnam et al. |
| 6,306,575 B1 | 10/2001 | Thomas et al. |
| 6,322,784 B1 | 11/2001 | Pittenger et al. |
| 6,322,786 B1 | 11/2001 | Anderson |
| 6,326,198 B1 | 12/2001 | Emerson et al. |
| 6,326,201 B1 | 12/2001 | Fung et al. |
| 6,328,765 B1 | 12/2001 | Hardwick et al. |
| 6,328,960 B1 | 12/2001 | McIntosh et al. |
| 6,333,029 B1 | 12/2001 | Vyakarnam et al. |
| 6,335,195 B1 | 1/2002 | Rodgers et al. |
| 6,338,942 B2 | 1/2002 | Kraus et al. |
| 6,340,592 B1 | 1/2002 | Stringer |
| 6,342,370 B1 | 1/2002 | Connolly et al. |
| 6,355,239 B1 | 3/2002 | Bruder et al. |
| 6,358,252 B1 | 3/2002 | Shapira |
| 6,361,997 B1 | 3/2002 | Huss |
| 6,365,149 B2 | 4/2002 | Vyakarnam et al. |
| 6,368,636 B1 | 4/2002 | McIntosh et al. |
| 6,372,210 B2 | 4/2002 | Brown |
| 6,372,244 B1 | 4/2002 | Antanavich et al. |
| 6,372,494 B1 | 4/2002 | Naughton et al. |
| 6,372,892 B1 | 4/2002 | Ballinger et al. |
| 6,376,742 B1 | 4/2002 | Zdrahala et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,387,693 B2 | 5/2002 | Rieser et al. |
| 6,387,964 B1 | 5/2002 | D'Agostino et al. |
| 6,392,118 B1 | 5/2002 | Hammang et al. |
| 6,394,812 B1 | 5/2002 | Sullivan et al. |
| 6,399,580 B1 | 6/2002 | Elias et al. |
| 6,410,320 B1 | 6/2002 | Humes |
| 6,414,219 B1 | 7/2002 | Denhardt et al. |
| 6,416,496 B1 | 7/2002 | Rogers et al. |
| 6,417,205 B1 | 7/2002 | Cooke et al. |
| 6,419,829 B2 | 7/2002 | Ho et al. |
| 6,420,138 B1 | 7/2002 | Gentz et al. |
| 6,423,681 B1 | 7/2002 | Barasch et al. |
| 6,426,332 B1 | 7/2002 | Rueger et al. |
| 6,428,802 B1 | 8/2002 | Atala |
| 6,429,012 B1 | 8/2002 | Kraus et al. |
| 6,429,013 B1 | 8/2002 | Halvorsen et al. |
| 6,432,653 B1 | 8/2002 | Okarma |
| 6,432,711 B1 | 8/2002 | Dinsmore et al. |
| 6,440,407 B1 | 8/2002 | Bauer et al. |
| 6,440,734 B1 | 8/2002 | Pykett et al. |
| 6,451,562 B1 | 9/2002 | Ruben et al. |
| 6,454,811 B1 | 9/2002 | Sherwood et al. |
| 6,455,678 B1 | 9/2002 | Yin et al. |
| 6,458,585 B1 | 10/2002 | Vachula et al. |
| 6,458,589 B1 | 10/2002 | Rambhatla et al. |
| 6,461,495 B1 | 10/2002 | Morrissey et al. |
| 6,461,853 B1 | 10/2002 | Zhu |
| 6,464,983 B1 | 10/2002 | Grotendorst |
| 6,465,205 B2 | 10/2002 | Hicks, Jr. |
| 6,465,247 B1 | 10/2002 | Weissman et al. |
| 6,465,249 B2 | 10/2002 | Reya et al. |
| 6,468,794 B1 | 10/2002 | Uchida et al. |
| 6,472,200 B1 | 10/2002 | Mitrani |
| 6,475,481 B2 | 11/2002 | Talmadge |
| 6,479,064 B1 | 11/2002 | Atala |
| 6,482,231 B1 | 11/2002 | Abatangelo et al. |
| 6,482,411 B1 | 11/2002 | Ahuja et al. |
| 6,482,645 B2 | 11/2002 | Atala |
| 6,482,926 B1 | 11/2002 | Thomas et al. |
| 6,488,925 B2 | 12/2002 | Ruben et al. |
| 6,491,918 B1 | 12/2002 | Thomas et al. |
| 6,495,129 B1 | 12/2002 | Li et al. |
| 6,495,364 B2 | 12/2002 | Hammang et al. |
| 6,497,875 B1 | 12/2002 | Sorrell et al. |
| 6,498,034 B1 | 12/2002 | Strobl |
| 6,506,574 B1 | 1/2003 | Rambhatla et al. |
| 6,511,510 B1 | 1/2003 | de Bruijn et al. |
| 6,511,767 B1 | 1/2003 | Calver et al. |
| 6,511,958 B1 | 1/2003 | Atkinson et al. |
| 6,514,514 B1 | 2/2003 | Atkinson et al. |
| 6,524,452 B1 | 2/2003 | Clark et al. |
| 6,528,052 B1 | 3/2003 | Smith et al. |
| 6,528,245 B2 | 3/2003 | Sanchez-Ramos et al. |
| 6,531,445 B1 | 3/2003 | Cohen et al. |
| 6,534,084 B1 | 3/2003 | Vyakarnam et al. |
| 6,537,807 B1 | 3/2003 | Smith et al. |
| 6,541,024 B1 | 4/2003 | Kadiyala et al. |
| 6,541,249 B2 | 4/2003 | Wager et al. |

(56) References Cited

U.S. PATENT DOCUMENTS

| | | |
|---|---|---|
| 6,544,506 B2 | 4/2003 | Reisner |
| 6,548,734 B1 | 4/2003 | Glimcher et al. |
| 6,555,324 B1 | 4/2003 | Olweus et al. |
| 6,555,374 B1 | 4/2003 | Gimble et al. |
| 6,559,119 B1 | 5/2003 | Burgess et al. |
| 6,562,616 B1 | 5/2003 | Toner et al. |
| 6,565,843 B1 | 5/2003 | Cohen et al. |
| 6,566,126 B2 | 5/2003 | Cadwell |
| 6,569,421 B2 | 5/2003 | Hodges |
| 6,569,427 B1 | 5/2003 | Boyse et al. |
| 6,569,428 B1 | 5/2003 | Isner et al. |
| 6,569,654 B2 | 5/2003 | Shastri et al. |
| 6,576,188 B1 | 6/2003 | Rose et al. |
| 6,576,428 B1 | 6/2003 | Assenmacher et al. |
| 6,576,464 B2 | 6/2003 | Gold et al. |
| 6,576,465 B1 | 6/2003 | Long |
| 6,582,471 B1 | 6/2003 | Bittmann et al. |
| 6,582,955 B2 | 6/2003 | Martinez et al. |
| 6,586,192 B1 | 7/2003 | Peschle et al. |
| 6,589,728 B2 | 7/2003 | Csete et al. |
| 6,589,786 B1 | 7/2003 | Mangano et al. |
| 6,593,123 B1 | 7/2003 | Wright et al. |
| 6,596,274 B1 | 7/2003 | Abatangelo et al. |
| 6,599,300 B2 | 7/2003 | Vibe-Hansen et al. |
| 6,599,520 B2 | 7/2003 | Scarborough et al. |
| 6,610,535 B1 | 8/2003 | Lu et al. |
| 6,613,798 B1 | 9/2003 | Porter et al. |
| 6,616,912 B2 | 9/2003 | Eddleman et al. |
| 6,617,070 B1 | 9/2003 | Morrissey et al. |
| 6,617,152 B2 | 9/2003 | Bryhan et al. |
| 6,617,159 B1 | 9/2003 | Cancedda et al. |
| 6,623,749 B2 | 9/2003 | Williams et al. |
| 6,623,942 B2 | 9/2003 | Ruben et al. |
| 6,624,108 B1 | 9/2003 | Clark et al. |
| 6,626,950 B2 | 9/2003 | Brown et al. |
| 6,627,191 B1 | 9/2003 | Bartelmez et al. |
| 6,629,003 B1 | 9/2003 | Frizzell et al. |
| 6,632,425 B1 | 10/2003 | Li et al. |
| 6,632,620 B1 | 10/2003 | Makarovskiy |
| 6,632,934 B1 | 10/2003 | Moreadith et al. |
| 6,638,765 B1 | 10/2003 | Rosenberg |
| 6,642,019 B1 | 11/2003 | Anderson et al. |
| 6,642,048 B2 | 11/2003 | Xu et al. |
| 6,642,049 B1 | 11/2003 | Chute et al. |
| 6,642,201 B1 | 11/2003 | Khavinson et al. |
| 6,645,489 B2 | 11/2003 | Pykett et al. |
| 6,645,727 B2 | 11/2003 | Thomas et al. |
| 6,645,763 B2 | 11/2003 | Kobayashi et al. |
| 6,649,189 B2 | 11/2003 | Talmadge et al. |
| 6,649,595 B2 | 11/2003 | Clackson et al. |
| 6,649,631 B1 | 11/2003 | Orme et al. |
| 6,653,105 B2 | 11/2003 | Triglia et al. |
| 6,653,134 B2 | 11/2003 | Prockop et al. |
| 6,660,523 B2 | 12/2003 | Blom et al. |
| 6,662,805 B2 | 12/2003 | Frondoza et al. |
| 6,667,034 B2 | 12/2003 | Palsson et al. |
| 6,667,176 B1 | 12/2003 | Funk et al. |
| 6,670,169 B1 | 12/2003 | Schob et al. |
| 6,670,175 B2 | 12/2003 | Wang et al. |
| 6,673,603 B2 | 1/2004 | Baetge et al. |
| 6,673,606 B1 | 1/2004 | Tennekoon et al. |
| 6,677,306 B1 | 1/2004 | Veis et al. |
| 6,683,192 B2 | 1/2004 | Baxter et al. |
| 6,685,936 B2 | 2/2004 | McIntosh et al. |
| 6,685,971 B2 | 2/2004 | Xu |
| 6,686,198 B1 | 2/2004 | Melton et al. |
| 6,689,324 B2 | 2/2004 | Inoue |
| 6,690,981 B1 | 2/2004 | Kawachi et al. |
| 6,696,575 B2 | 2/2004 | Schmidt et al. |
| 6,699,716 B2 | 3/2004 | Sullivan et al. |
| 6,703,017 B1 | 3/2004 | Peck et al. |
| 6,703,209 B1 | 3/2004 | Baetscher et al. |
| 6,706,293 B1 | 3/2004 | Quintanilla Almagro et al. |
| 6,709,864 B1 | 3/2004 | Pittenger et al. |
| 6,712,850 B2 | 3/2004 | Vyakarnam et al. |
| 6,719,969 B1 | 4/2004 | Hogaboam et al. |
| 6,719,970 B1 | 4/2004 | Costantino et al. |
| 6,720,340 B1 | 4/2004 | Cooke et al. |
| 6,730,314 B2 | 5/2004 | Jeschke et al. |
| 6,730,315 B2 | 5/2004 | Usala et al. |
| 6,730,510 B2 | 5/2004 | Roos et al. |
| 6,733,746 B2 | 5/2004 | Daley et al. |
| 6,734,000 B2 | 5/2004 | Chin et al. |
| 6,740,493 B1 | 5/2004 | Long et al. |
| 6,759,039 B2 | 7/2004 | Tsang et al. |
| 6,759,245 B1 | 7/2004 | Toner et al. |
| 6,761,883 B2 | 7/2004 | Weissman et al. |
| 6,761,887 B1 | 7/2004 | Kavalkovich et al. |
| 6,767,699 B2 | 7/2004 | Polo et al. |
| 6,767,737 B1 | 7/2004 | Wilson et al. |
| 6,767,738 B1 | 7/2004 | Gage et al. |
| 6,767,740 B2 | 7/2004 | Sramek et al. |
| 6,770,478 B2 | 8/2004 | Crowe et al. |
| 6,777,227 B2 | 8/2004 | Ricci et al. |
| 6,777,231 B1 | 8/2004 | Katz et al. |
| 6,780,612 B1 | 8/2004 | Ford et al. |
| 6,787,355 B1 | 9/2004 | Miller et al. |
| 6,790,455 B2 | 9/2004 | Chu et al. |
| 6,793,939 B2 | 9/2004 | Badylak |
| 6,797,269 B2 | 9/2004 | Mosca et al. |
| 6,797,514 B2 | 9/2004 | Berenson et al. |
| 6,800,480 B1 | 10/2004 | Bodnar et al. |
| 6,802,971 B2 | 10/2004 | Gorsuch et al. |
| 6,805,860 B1 | 10/2004 | Alt |
| 6,809,117 B2 | 10/2004 | Enikolopov et al. |
| 6,811,773 B1 | 11/2004 | Gentz et al. |
| 6,811,776 B2 | 11/2004 | Kale et al. |
| 6,814,961 B1 | 11/2004 | Jensen et al. |
| 6,821,513 B1 | 11/2004 | Fleming |
| 6,821,790 B2 | 11/2004 | Mahant et al. |
| 6,828,145 B2 | 12/2004 | Avital et al. |
| 6,833,269 B2 | 12/2004 | Carpenter |
| 6,835,377 B2 | 12/2004 | Goldberg et al. |
| 6,835,566 B2 | 12/2004 | Smith et al. |
| 6,838,284 B2 | 1/2005 | de Bruijn et al. |
| 6,841,150 B2 | 1/2005 | Halvorsen et al. |
| 6,841,151 B2 | 1/2005 | Stringer |
| 6,841,294 B1 | 1/2005 | Morrissey et al. |
| 6,841,355 B1 | 1/2005 | Livant |
| 6,841,386 B2 | 1/2005 | Kraus et al. |
| 6,841,542 B2 | 1/2005 | Bartelmez et al. |
| 6,844,011 B1 | 1/2005 | Faustman |
| 6,844,187 B1 | 1/2005 | Weschler et al. |
| 6,849,051 B2 | 2/2005 | Sramek et al. |
| 6,849,255 B2 | 2/2005 | Gazit et al. |
| 6,849,454 B2 | 2/2005 | Kelly et al. |
| 6,849,662 B2 | 2/2005 | Enikolopov et al. |
| 6,852,308 B2 | 2/2005 | Kohn et al. |
| 6,852,321 B2 | 2/2005 | Colucci et al. |
| 6,852,533 B1 | 2/2005 | Rafii et al. |
| 6,855,242 B1 | 2/2005 | Comninellis et al. |
| 6,855,542 B2 | 2/2005 | DiMilla et al. |
| 6,863,900 B2 | 3/2005 | Kadiyala et al. |
| 6,866,843 B2 | 3/2005 | Habener et al. |
| 6,872,389 B1 | 3/2005 | Faris |
| 6,875,430 B2 | 4/2005 | McIntosh et al. |
| 6,887,600 B2 | 5/2005 | Morrissey et al. |
| 6,887,704 B2 | 5/2005 | Peled et al. |
| 6,908,763 B1 | 6/2005 | Akashi et al. |
| 6,911,201 B1 | 6/2005 | Merchav et al. |
| 6,914,279 B2 | 7/2005 | Lu et al. |
| 6,939,955 B2 | 9/2005 | Rameshwar |
| 6,943,008 B1 | 9/2005 | Ma |
| 6,944,522 B2 | 9/2005 | Karmiy et al. |
| 6,965,018 B2 | 11/2005 | Mikesell et al. |
| 6,969,308 B2 | 11/2005 | Doi et al. |
| 6,979,308 B1 | 12/2005 | McDonald et al. |
| 6,979,321 B2 | 12/2005 | Geis et al. |
| 6,988,004 B2 | 1/2006 | Kanno et al. |
| 7,008,394 B2 | 3/2006 | Geise et al. |
| 7,015,037 B1 | 3/2006 | Furcht et al. |
| 7,029,666 B2 | 4/2006 | Bruder et al. |
| 7,033,339 B1 | 4/2006 | Lynn |
| 7,033,823 B2 | 4/2006 | Chang |

(56) References Cited

U.S. PATENT DOCUMENTS

| | | |
|---|---|---|
| 7,041,493 B2 | 5/2006 | Rao |
| 7,045,098 B2 | 5/2006 | Stephens |
| 7,052,517 B2 | 5/2006 | Murphy et al. |
| 7,056,493 B2 | 6/2006 | Kohn et al. |
| 7,112,441 B2 | 9/2006 | Uemura et al. |
| 7,118,672 B2 | 10/2006 | Husain et al. |
| 7,122,178 B1 | 10/2006 | Simmons et al. |
| 7,160,719 B2 | 1/2007 | Nyberg |
| 7,169,295 B2 | 1/2007 | Husain et al. |
| 7,172,696 B1 | 2/2007 | Martinez et al. |
| 7,175,763 B2 | 2/2007 | Husain et al. |
| 7,192,776 B2 | 3/2007 | Stephens |
| 7,195,711 B2 | 3/2007 | Gorsuch et al. |
| 7,250,154 B2 | 7/2007 | Kohn et al. |
| 7,270,996 B2 | 9/2007 | Cannon et al. |
| 7,271,234 B2 | 9/2007 | Kohn et al. |
| 7,294,259 B2 | 11/2007 | Cote et al. |
| 7,300,571 B2 | 11/2007 | Cote et al. |
| 7,303,676 B2 | 12/2007 | Husain et al. |
| 7,303,677 B2 | 12/2007 | Cote et al. |
| 7,341,062 B2 | 3/2008 | Chachques et al. |
| 7,358,001 B2 | 4/2008 | Morrissey et al. |
| 7,361,493 B1 | 4/2008 | Hammond et al. |
| 7,368,169 B2 | 5/2008 | Kohn et al. |
| 7,378,271 B2 | 5/2008 | Bader |
| 7,399,872 B2 | 7/2008 | Webster et al. |
| 7,416,884 B2 | 8/2008 | Gemmiti et al. |
| 7,425,440 B2 | 9/2008 | Malinge et al. |
| 7,435,586 B2 | 10/2008 | Bartlett et al. |
| 7,438,902 B2 | 10/2008 | Habener et al. |
| 7,439,057 B2 | 10/2008 | Frangos et al. |
| 7,452,529 B2 | 11/2008 | Brown, Jr. et al. |
| 7,491,388 B1 | 2/2009 | McIntosh et al. |
| 7,494,811 B2 | 2/2009 | Wolfinbarger, Jr. et al. |
| 7,514,074 B2 | 4/2009 | Pittenger et al. |
| 7,514,075 B2 | 4/2009 | Hedrick et al. |
| 7,524,676 B2 | 4/2009 | Reiter et al. |
| 7,531,351 B2 | 5/2009 | Marx et al. |
| 7,534,609 B2 | 5/2009 | Merchav et al. |
| 7,572,374 B2 | 8/2009 | Gorsuch et al. |
| 7,579,179 B2 | 8/2009 | Bryhan et al. |
| 7,585,412 B2 | 9/2009 | Gorsuch et al. |
| 7,588,938 B2 | 9/2009 | Ma |
| 7,598,075 B2 | 10/2009 | Smith et al. |
| 7,608,447 B2 | 10/2009 | Cohen et al. |
| 7,659,118 B2 | 2/2010 | Furcht et al. |
| 7,678,573 B2 | 3/2010 | Merchav et al. |
| 7,682,822 B2 | 3/2010 | Noll et al. |
| 7,682,823 B1 | 3/2010 | Runyon |
| 7,718,430 B2 | 5/2010 | Antwiler |
| 7,722,896 B2 | 5/2010 | Kohn et al. |
| D620,732 S | 8/2010 | Andrews |
| 7,838,122 B2 | 11/2010 | Kohn et al. |
| 7,838,289 B2 | 11/2010 | Furcht et al. |
| 7,892,829 B2 | 2/2011 | Pittenger et al. |
| 7,919,307 B2 | 4/2011 | Klaus et al. |
| 7,927,587 B2 | 4/2011 | Blazer et al. |
| 7,989,851 B2 | 8/2011 | Lu et al. |
| 8,008,528 B2 | 8/2011 | Kohn et al. |
| 8,034,365 B2 | 10/2011 | Baluca |
| 8,075,881 B2 | 12/2011 | Verfaillie et al. |
| 8,147,824 B2 | 4/2012 | Maziarz et al. |
| 8,147,863 B2 | 4/2012 | Kohn et al. |
| 8,158,120 B2 | 4/2012 | Pittenger et al. |
| 8,158,121 B2 | 4/2012 | Pittenger et al. |
| 8,252,280 B1 | 8/2012 | Verfaillie et al. |
| 8,252,887 B2 | 8/2012 | Bolikal et al. |
| 8,288,159 B2 | 10/2012 | Warren et al. |
| 8,288,590 B2 | 10/2012 | Kohn et al. |
| 8,298,823 B2 | 10/2012 | Warren et al. |
| 8,309,347 B2 | 11/2012 | Antwiler |
| 8,321,145 B2 | 11/2012 | Antwiler |
| 8,361,453 B2 | 1/2013 | Uhrich et al. |
| 8,377,683 B2 | 2/2013 | Lu et al. |
| 8,383,397 B2 | 2/2013 | Wojciechowski et al. |
| 8,383,806 B2 | 2/2013 | Rameshwar |
| 8,399,245 B2 | 3/2013 | Leuthaeuser et al. |
| 8,415,449 B2 | 4/2013 | Kohn et al. |
| 8,435,781 B2 | 5/2013 | Kodama |
| 8,461,289 B2 | 6/2013 | Kohn et al. |
| 8,476,399 B2 | 7/2013 | Bolikal et al. |
| 8,486,621 B2 | 7/2013 | Luo et al. |
| 8,486,695 B2 | 7/2013 | Danilkovitch et al. |
| 8,492,140 B2 | 7/2013 | Smith et al. |
| 8,492,150 B2 | 7/2013 | Parker et al. |
| 8,524,496 B2 | 9/2013 | Meiron et al. |
| 8,529,888 B2 | 9/2013 | Meiron et al. |
| 8,540,499 B2 | 9/2013 | Page et al. |
| 8,551,511 B2 | 10/2013 | Brandom et al. |
| 8,580,249 B2 | 11/2013 | Blazar et al. |
| 8,678,638 B2 | 3/2014 | Wong |
| 8,785,181 B2 | 7/2014 | Antwiler |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,895,291 B2 | 11/2014 | Dilorenzo et al. |
| 9,057,045 B2 | 6/2015 | Gibbons et al. |
| 9,109,193 B2 | 8/2015 | Galliher et al. |
| 9,175,259 B2 | 11/2015 | Nankervis |
| 9,220,810 B2 | 12/2015 | Ma et al. |
| 9,260,698 B2 | 2/2016 | Antwiler |
| 9,441,195 B2 | 9/2016 | Wojciechowski et al. |
| 9,534,198 B2 | 1/2017 | Page et al. |
| 9,677,042 B2 | 6/2017 | Stanton, IV et al. |
| 9,725,689 B2 | 8/2017 | Stanton, IV et al. |
| 9,732,313 B2 | 8/2017 | Hirschel et al. |
| 10,093,956 B2 | 10/2018 | Hirschel et al. |
| 10,494,421 B2 | 12/2019 | Castillo |
| 2001/0017188 A1 | 8/2001 | Cooley et al. |
| 2001/0020086 A1 | 9/2001 | Hubbell et al. |
| 2001/0021516 A1 | 9/2001 | Wei et al. |
| 2001/0029046 A1 | 10/2001 | Beaulieu |
| 2001/0033834 A1 | 10/2001 | Wilkison et al. |
| 2001/0036663 A1 | 11/2001 | Kraus et al. |
| 2001/0041687 A1 | 11/2001 | Mruk |
| 2001/0044413 A1 | 11/2001 | Pierce et al. |
| 2001/0049139 A1 | 12/2001 | Lagasse et al. |
| 2002/0015724 A1 | 2/2002 | Yang et al. |
| 2002/0018804 A1 | 2/2002 | Austin et al. |
| 2002/0028510 A1 | 3/2002 | Sanberg et al. |
| 2002/0031757 A1 | 3/2002 | Ohgushi et al. |
| 2002/0037278 A1 | 3/2002 | Ueno et al. |
| 2002/0045260 A1 | 4/2002 | Hung et al. |
| 2002/0064869 A1 | 5/2002 | Ebner et al. |
| 2002/0076400 A1 | 6/2002 | Katz et al. |
| 2002/0077687 A1 | 6/2002 | Ahn |
| 2002/0082698 A1 | 6/2002 | Parenteau et al. |
| 2002/0116054 A1 | 8/2002 | Lundell et al. |
| 2002/0128581 A1 | 9/2002 | Vishnoi et al. |
| 2002/0128582 A1 | 9/2002 | Farrell et al. |
| 2002/0128583 A1 | 9/2002 | Min et al. |
| 2002/0128584 A1 | 9/2002 | Brown et al. |
| 2002/0130100 A1 | 9/2002 | Smith |
| 2002/0132343 A1 | 9/2002 | Lum |
| 2002/0139743 A1 | 10/2002 | Critz et al. |
| 2002/0142457 A1 | 10/2002 | Umezawa et al. |
| 2002/0146678 A1 | 10/2002 | Benvenisty |
| 2002/0146817 A1 | 10/2002 | Cannon et al. |
| 2002/0150989 A1 | 10/2002 | Greene et al. |
| 2002/0151056 A1 | 10/2002 | Sasai et al. |
| 2002/0159981 A1 | 10/2002 | Peled et al. |
| 2002/0160032 A1 | 10/2002 | Long et al. |
| 2002/0160510 A1 | 10/2002 | Hariri |
| 2002/0168765 A1 | 11/2002 | Prockop et al. |
| 2002/0169408 A1 | 11/2002 | Beretta et al. |
| 2002/0182241 A1 | 12/2002 | Borenstein et al. |
| 2002/0182664 A1 | 12/2002 | Dolecek et al. |
| 2002/0188962 A1 | 12/2002 | Denhardt et al. |
| 2002/0197240 A1 | 12/2002 | Chiu |
| 2003/0021850 A1 | 1/2003 | Xu |
| 2003/0022390 A1 | 1/2003 | Stephens |

(56) References Cited

U.S. PATENT DOCUMENTS

| | | |
|---|---|---|
| 2003/0027330 A1 | 2/2003 | Lanza et al. |
| 2003/0027331 A1 | 2/2003 | Yan et al. |
| 2003/0032143 A1 | 2/2003 | Neff et al. |
| 2003/0036168 A1 | 2/2003 | Ni et al. |
| 2003/0037836 A1 | 2/2003 | Blatt et al. |
| 2003/0040113 A1 | 2/2003 | Mizuno et al. |
| 2003/0049236 A1 | 3/2003 | Kassem et al. |
| 2003/0054331 A1 | 3/2003 | Fraser et al. |
| 2003/0059851 A1 | 3/2003 | Smith |
| 2003/0059939 A1 | 3/2003 | Page et al. |
| 2003/0069650 A1 | 4/2003 | Karmiy et al. |
| 2003/0078345 A1 | 4/2003 | Morrisey |
| 2003/0082795 A1 | 5/2003 | Shuler et al. |
| 2003/0086915 A1 | 5/2003 | Rader et al. |
| 2003/0089471 A1 | 5/2003 | Gehr et al. |
| 2003/0092101 A1 | 5/2003 | Ni et al. |
| 2003/0101465 A1 | 5/2003 | Lawman et al. |
| 2003/0103957 A1 | 6/2003 | McKerracher |
| 2003/0104568 A1 | 6/2003 | Lee |
| 2003/0113813 A1 | 6/2003 | Heidaran et al. |
| 2003/0113910 A1 | 6/2003 | Levanduski |
| 2003/0124091 A1 | 7/2003 | Tuse et al. |
| 2003/0124721 A1 | 7/2003 | Cheatham et al. |
| 2003/0130593 A1 | 7/2003 | Gonzalez |
| 2003/0133918 A1 | 7/2003 | Sherley |
| 2003/0138950 A1 | 7/2003 | McAllister et al. |
| 2003/0143727 A1 | 7/2003 | Chang |
| 2003/0148152 A1 | 8/2003 | Morrisey |
| 2003/0149011 A1 | 8/2003 | Ackerman et al. |
| 2003/0152558 A1 | 8/2003 | Luft et al. |
| 2003/0157078 A1 | 8/2003 | Hall et al. |
| 2003/0157709 A1 | 8/2003 | DiMilla et al. |
| 2003/0161817 A1 | 8/2003 | Young et al. |
| 2003/0166272 A1 | 9/2003 | Abuljadayel |
| 2003/0170214 A1 | 9/2003 | Bader |
| 2003/0180296 A1 | 9/2003 | Salcedo et al. |
| 2003/0185817 A1 | 10/2003 | Thomas et al. |
| 2003/0202938 A1 | 10/2003 | Rameshwar |
| 2003/0203483 A1 | 10/2003 | Seshi |
| 2003/0204323 A1 | 10/2003 | Morrisey |
| 2003/0211602 A1 | 11/2003 | Atala |
| 2003/0211603 A1 | 11/2003 | Earp et al. |
| 2003/0216718 A1 | 11/2003 | Hamblin et al. |
| 2003/0219898 A1 | 11/2003 | Sugaya et al. |
| 2003/0223968 A1 | 12/2003 | Yang |
| 2003/0224420 A1 | 12/2003 | Hellerstein et al. |
| 2003/0224510 A1 | 12/2003 | Yamaguchi et al. |
| 2003/0225010 A1 | 12/2003 | Rameshwar |
| 2003/0232432 A1 | 12/2003 | Bhat |
| 2003/0232752 A1 | 12/2003 | Freeman et al. |
| 2003/0235909 A1 | 12/2003 | Hariri et al. |
| 2004/0009158 A1 | 1/2004 | Sands et al. |
| 2004/0009589 A1 | 1/2004 | Levenberg et al. |
| 2004/0010231 A1 | 1/2004 | Leonhardt et al. |
| 2004/0014209 A1 | 1/2004 | Lassar et al. |
| 2004/0018174 A1 | 1/2004 | Palasis |
| 2004/0018617 A1 | 1/2004 | Hwang |
| 2004/0023324 A1 | 2/2004 | Sakano et al. |
| 2004/0023370 A1 | 2/2004 | Yu et al. |
| 2004/0027914 A1 | 2/2004 | Vrane |
| 2004/0032430 A1 | 2/2004 | Yung et al. |
| 2004/0033214 A1 | 2/2004 | Young et al. |
| 2004/0033599 A1 | 2/2004 | Rosenberg |
| 2004/0037811 A1 | 2/2004 | Penn et al. |
| 2004/0037815 A1 | 2/2004 | Clarke et al. |
| 2004/0038316 A1 | 2/2004 | Kaiser et al. |
| 2004/0053869 A1 | 3/2004 | Andrews et al. |
| 2004/0062753 A1 | 4/2004 | Rezania et al. |
| 2004/0063205 A1 | 4/2004 | Xu |
| 2004/0067585 A1 | 4/2004 | Wang et al. |
| 2004/0071668 A1 | 4/2004 | Bays et al. |
| 2004/0072259 A1 | 4/2004 | Scadden et al. |
| 2004/0077079 A1 | 4/2004 | Storgaard et al. |
| 2004/0079248 A1 | 4/2004 | Mayer et al. |
| 2004/0087016 A1 | 5/2004 | Keating et al. |
| 2004/0091936 A1 | 5/2004 | West |
| 2004/0096476 A1 | 5/2004 | Uhrich et al. |
| 2004/0097408 A1 | 5/2004 | Leder et al. |
| 2004/0101959 A1 | 5/2004 | Marko et al. |
| 2004/0107453 A1 | 6/2004 | Furcht et al. |
| 2004/0110286 A1 | 6/2004 | Bhatia |
| 2004/0115804 A1 | 6/2004 | Fu et al. |
| 2004/0115806 A1 | 6/2004 | Fu |
| 2004/0120932 A1 | 6/2004 | Zahner |
| 2004/0121461 A1 | 6/2004 | Honmou et al. |
| 2004/0121464 A1 | 6/2004 | Rathjen et al. |
| 2004/0126405 A1 | 7/2004 | Sahatjian et al. |
| 2004/0128077 A1 | 7/2004 | Koebler et al. |
| 2004/0131601 A1 | 7/2004 | Epstein et al. |
| 2004/0132184 A1 | 7/2004 | Dennis et al. |
| 2004/0136967 A1 | 7/2004 | Weiss et al. |
| 2004/0137612 A1 | 7/2004 | Baksh |
| 2004/0137613 A1 | 7/2004 | Vacanti et al. |
| 2004/0143174 A1 | 7/2004 | Brubaker |
| 2004/0143863 A1 | 7/2004 | Li et al. |
| 2004/0151700 A1 | 8/2004 | Harlan et al. |
| 2004/0151701 A1 | 8/2004 | Kim et al. |
| 2004/0151706 A1 | 8/2004 | Shakhov et al. |
| 2004/0151729 A1 | 8/2004 | Michalopoulos et al. |
| 2004/0152190 A1 | 8/2004 | Sumita |
| 2004/0161419 A1 | 8/2004 | Strom et al. |
| 2004/0171533 A1 | 9/2004 | Zehentner et al. |
| 2004/0180347 A1 | 9/2004 | Stanton et al. |
| 2004/0191902 A1 | 9/2004 | Hambor et al. |
| 2004/0197310 A1 | 10/2004 | Sanberg et al. |
| 2004/0197375 A1 | 10/2004 | Rezania et al. |
| 2004/0208786 A1 | 10/2004 | Kevy et al. |
| 2004/0214275 A1 | 10/2004 | Soejima et al. |
| 2004/0219134 A1 | 11/2004 | Naughton et al. |
| 2004/0219136 A1 | 11/2004 | Hariri |
| 2004/0219563 A1 | 11/2004 | West et al. |
| 2004/0224403 A1 | 11/2004 | Bhatia |
| 2004/0229351 A1 | 11/2004 | Rodriguez et al. |
| 2004/0234972 A1 | 11/2004 | Owens et al. |
| 2004/0235158 A1 | 11/2004 | Bartlett et al. |
| 2004/0235160 A1 | 11/2004 | Nishikawa et al. |
| 2004/0235166 A1 | 11/2004 | Prockop et al. |
| 2004/0242469 A1 | 12/2004 | Lee et al. |
| 2004/0258669 A1 | 12/2004 | Dzau et al. |
| 2004/0259242 A1 | 12/2004 | Malinge et al. |
| 2004/0259254 A1 | 12/2004 | Honmou et al. |
| 2004/0260058 A1 | 12/2004 | Scheek et al. |
| 2004/0260318 A1 | 12/2004 | Hunter et al. |
| 2004/0265996 A1 | 12/2004 | Schwarz et al. |
| 2005/0002914 A1 | 1/2005 | Rosen et al. |
| 2005/0003460 A1 | 1/2005 | Nilsson et al. |
| 2005/0003527 A1 | 1/2005 | Lang et al. |
| 2005/0003534 A1 | 1/2005 | Huberman et al. |
| 2005/0008624 A1 | 1/2005 | Peled et al. |
| 2005/0008626 A1 | 1/2005 | Fraser et al. |
| 2005/0009178 A1 | 1/2005 | Yost et al. |
| 2005/0009179 A1 | 1/2005 | Gemmiti et al. |
| 2005/0009181 A1 | 1/2005 | Black et al. |
| 2005/0013804 A1 | 1/2005 | Kato et al. |
| 2005/0014252 A1 | 1/2005 | Chu et al. |
| 2005/0014253 A1 | 1/2005 | Ehmann et al. |
| 2005/0014254 A1 | 1/2005 | Kruse |
| 2005/0014255 A1 | 1/2005 | Tang et al. |
| 2005/0019801 A1 | 1/2005 | Rubin et al. |
| 2005/0019908 A1 | 1/2005 | Hariri |
| 2005/0019910 A1 | 1/2005 | Takagi et al. |
| 2005/0019911 A1 | 1/2005 | Gronthos et al. |
| 2005/0026836 A1 | 2/2005 | Dack et al. |
| 2005/0031587 A1 | 2/2005 | Tsutsui et al. |
| 2005/0031595 A1 | 2/2005 | Peled et al. |
| 2005/0031598 A1 | 2/2005 | Levenberg et al. |
| 2005/0032122 A1 | 2/2005 | Hwang et al. |
| 2005/0032207 A1 | 2/2005 | Wobus et al. |
| 2005/0032209 A1 | 2/2005 | Messina et al. |
| 2005/0032218 A1 | 2/2005 | Gerlach |
| 2005/0036980 A1 | 2/2005 | Chaney et al. |
| 2005/0037488 A1 | 2/2005 | Mitalipova et al. |
| 2005/0037490 A1 | 2/2005 | Rosenberg et al. |
| 2005/0037492 A1 | 2/2005 | Xu et al. |

(56) References Cited

U.S. PATENT DOCUMENTS

| | | |
|---|---|---|
| 2005/0037493 A1 | 2/2005 | Mandalam et al. |
| 2005/0037949 A1 | 2/2005 | O'Brien et al. |
| 2005/0106119 A1 | 5/2005 | Brandom et al. |
| 2005/0106127 A1 | 5/2005 | Kraus et al. |
| 2005/0112447 A1 | 5/2005 | Fletcher et al. |
| 2005/0112762 A1 | 5/2005 | Hart et al. |
| 2005/0118712 A1 | 6/2005 | Tsai et al. |
| 2005/0130297 A1 | 6/2005 | Sarem et al. |
| 2005/0136093 A1 | 6/2005 | Denk |
| 2005/0137517 A1 | 6/2005 | Blickhan et al. |
| 2005/0142162 A1 | 6/2005 | Hunter et al. |
| 2005/0149157 A1 | 7/2005 | Hunter et al. |
| 2005/0152946 A1 | 7/2005 | Hunter et al. |
| 2005/0158289 A1 | 7/2005 | Simmons et al. |
| 2005/0172340 A1 | 8/2005 | Logvinov et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0180957 A1 | 8/2005 | Scharp et al. |
| 2005/0181502 A1 | 8/2005 | Furcht et al. |
| 2005/0182463 A1 | 8/2005 | Hunter et al. |
| 2005/0183731 A1 | 8/2005 | Hunter et al. |
| 2005/0186244 A1 | 8/2005 | Hunter et al. |
| 2005/0186671 A1 | 8/2005 | Cannon et al. |
| 2005/0187140 A1 | 8/2005 | Hunter et al. |
| 2005/0196421 A1 | 9/2005 | Hunter et al. |
| 2005/0208095 A1 | 9/2005 | Hunter et al. |
| 2005/0244963 A1 | 11/2005 | Teplyashin |
| 2005/0249731 A1 | 11/2005 | Aslan et al. |
| 2005/0255118 A1 | 11/2005 | Wehner |
| 2005/0261674 A1 | 11/2005 | Nobis et al. |
| 2005/0277577 A1 | 12/2005 | Hunter et al. |
| 2005/0281790 A1 | 12/2005 | Simmons et al. |
| 2005/0282733 A1 | 12/2005 | Prins et al. |
| 2005/0283844 A1 | 12/2005 | Furcht et al. |
| 2006/0002900 A1 | 1/2006 | Binder et al. |
| 2006/0008452 A1 | 1/2006 | Simmons et al. |
| 2006/0019388 A1 | 1/2006 | Hutmacher et al. |
| 2006/0019389 A1 | 1/2006 | Yayon et al. |
| 2006/0054941 A1 | 3/2006 | Lu et al. |
| 2006/0083720 A1 | 4/2006 | Fraser et al. |
| 2006/0099198 A1 | 5/2006 | Thomson et al. |
| 2006/0166364 A1 | 7/2006 | Senesac |
| 2006/0172008 A1 | 8/2006 | Yayon et al. |
| 2006/0193840 A1 | 8/2006 | Gronthos et al. |
| 2006/0228798 A1 | 10/2006 | Verfaillie et al. |
| 2006/0233834 A1 | 10/2006 | Guehenneux et al. |
| 2006/0239909 A1 | 10/2006 | Anderson et al. |
| 2006/0258586 A1 | 11/2006 | Sheppard et al. |
| 2006/0258933 A1 | 11/2006 | Ellis et al. |
| 2006/0259998 A1 | 11/2006 | Brumbley et al. |
| 2006/0280748 A1 | 12/2006 | Buckheit |
| 2006/0286077 A1 | 12/2006 | Gronthos et al. |
| 2007/0005148 A1 | 1/2007 | Barofsky et al. |
| 2007/0011752 A1 | 1/2007 | Paleyanda |
| 2007/0042462 A1 | 2/2007 | Hildinger |
| 2007/0065938 A1 | 3/2007 | Gronthos et al. |
| 2007/0105222 A1 | 5/2007 | Wolfinbarger et al. |
| 2007/0116612 A1 | 5/2007 | Williamson |
| 2007/0117180 A1 | 5/2007 | Morikawa et al. |
| 2007/0122904 A1 | 5/2007 | Nordon |
| 2007/0123996 A1 | 5/2007 | Sugaya et al. |
| 2007/0160583 A1 | 7/2007 | Lange et al. |
| 2007/0166834 A1 | 7/2007 | Williamson et al. |
| 2007/0178071 A1 | 8/2007 | Westenfelder |
| 2007/0192715 A1 | 8/2007 | Kataria et al. |
| 2007/0196421 A1 | 8/2007 | Hunter et al. |
| 2007/0197957 A1 | 8/2007 | Hunter et al. |
| 2007/0198063 A1 | 8/2007 | Hunter et al. |
| 2007/0202485 A1 | 8/2007 | Nees et al. |
| 2007/0203330 A1 | 8/2007 | Kretschmar et al. |
| 2007/0208134 A1 | 9/2007 | Hunter et al. |
| 2007/0231305 A1 | 10/2007 | Noll et al. |
| 2007/0258943 A1 | 11/2007 | Penn et al. |
| 2007/0274970 A1 | 11/2007 | Gordon et al. |
| 2007/0275457 A1 | 11/2007 | Granchelli et al. |
| 2007/0295651 A1 | 12/2007 | Martinez et al. |
| 2007/0298015 A1 | 12/2007 | Beer et al. |
| 2007/0298497 A1 | 12/2007 | Antwiler |
| 2008/0003663 A1 | 1/2008 | Bryhan et al. |
| 2008/0009458 A1 | 1/2008 | Dornan et al. |
| 2008/0032398 A1 | 2/2008 | Cannon et al. |
| 2008/0050770 A1 | 2/2008 | Zhang et al. |
| 2008/0063600 A1 | 3/2008 | Aguzzi et al. |
| 2008/0064649 A1 | 3/2008 | Rameshwar |
| 2008/0069807 A1 | 3/2008 | Jy et al. |
| 2008/0095676 A1 | 4/2008 | Andretta |
| 2008/0095690 A1 | 4/2008 | Liu |
| 2008/0103412 A1 | 5/2008 | Chin |
| 2008/0110827 A1 | 5/2008 | Cote et al. |
| 2008/0113426 A1 | 5/2008 | Smith et al. |
| 2008/0113440 A1 | 5/2008 | Gurney et al. |
| 2008/0153077 A1 | 6/2008 | Henry |
| 2008/0160597 A1 | 7/2008 | van der Heiden et al. |
| 2008/0166808 A1 | 7/2008 | Nyberg |
| 2008/0181879 A1 | 7/2008 | Catelas et al. |
| 2008/0190857 A1 | 8/2008 | Beretta et al. |
| 2008/0194017 A1 | 8/2008 | Esser et al. |
| 2008/0206831 A1 | 8/2008 | Coffey et al. |
| 2008/0220522 A1 | 9/2008 | Antwiler |
| 2008/0220523 A1 | 9/2008 | Antwiler |
| 2008/0220524 A1 | 9/2008 | Noll et al. |
| 2008/0220526 A1 | 9/2008 | Ellison et al. |
| 2008/0221443 A1 | 9/2008 | Ritchie et al. |
| 2008/0227189 A1 | 9/2008 | Bader |
| 2008/0227190 A1 | 9/2008 | Antwiler |
| 2008/0248572 A1 | 10/2008 | Antwiler |
| 2008/0254533 A1 | 10/2008 | Antwiler |
| 2008/0268165 A1 | 10/2008 | Fekety et al. |
| 2008/0268538 A1 | 10/2008 | Nordon et al. |
| 2008/0306095 A1 | 12/2008 | Crawford |
| 2009/0004738 A1 | 1/2009 | Merchav et al. |
| 2009/0011399 A1 | 1/2009 | Fischer |
| 2009/0047289 A1 | 2/2009 | Denhardt et al. |
| 2009/0074728 A1 | 3/2009 | Gronthos et al. |
| 2009/0075881 A1 | 3/2009 | Catelas et al. |
| 2009/0076481 A1 | 3/2009 | Stegmann et al. |
| 2009/0081770 A1 | 3/2009 | Srienc et al. |
| 2009/0081797 A1 | 3/2009 | Fadeev et al. |
| 2009/0092608 A1 | 4/2009 | Ni et al. |
| 2009/0098103 A1 | 4/2009 | Madison et al. |
| 2009/0098645 A1 | 4/2009 | Fang et al. |
| 2009/0100944 A1 | 4/2009 | Newby |
| 2009/0104163 A1 | 4/2009 | Deans et al. |
| 2009/0104653 A1 | 4/2009 | Paldus et al. |
| 2009/0104692 A1 | 4/2009 | Bartfeld et al. |
| 2009/0104699 A1 | 4/2009 | Newby et al. |
| 2009/0118161 A1 | 5/2009 | Cruz |
| 2009/0181087 A1 | 7/2009 | Kraus et al. |
| 2009/0183581 A1 | 7/2009 | Wilkinson et al. |
| 2009/0191627 A1 | 7/2009 | Fadeev et al. |
| 2009/0191632 A1 | 7/2009 | Fadeev et al. |
| 2009/0191634 A1 | 7/2009 | Martin et al. |
| 2009/0203065 A1 | 8/2009 | Gehman et al. |
| 2009/0203129 A1 | 8/2009 | Furcht et al. |
| 2009/0203130 A1 | 8/2009 | Furcht et al. |
| 2009/0214382 A1 | 8/2009 | Burgess et al. |
| 2009/0214481 A1 | 8/2009 | Muhs et al. |
| 2009/0214652 A1 | 8/2009 | Hunter et al. |
| 2009/0215022 A1 | 8/2009 | Page et al. |
| 2009/0227024 A1 | 9/2009 | Baker et al. |
| 2009/0227027 A1 | 9/2009 | Baker et al. |
| 2009/0233334 A1 | 9/2009 | Hildinger et al. |
| 2009/0233353 A1 | 9/2009 | Furcht et al. |
| 2009/0233354 A1 | 9/2009 | Furcht et al. |
| 2009/0258379 A1 | 10/2009 | Klein et al. |
| 2009/0269841 A1 | 10/2009 | Wojciechowski et al. |
| 2009/0270725 A1 | 10/2009 | Leimbach et al. |
| 2009/0280153 A1 | 11/2009 | Hunter et al. |
| 2009/0280565 A1 | 11/2009 | Jolicoeur et al. |
| 2009/0291890 A1 | 11/2009 | Madison et al. |
| 2010/0009409 A1 | 1/2010 | Hubbell et al. |
| 2010/0021954 A1 | 1/2010 | Deshayes et al. |

(56) References Cited

U.S. PATENT DOCUMENTS

| | | |
|---|---|---|
| 2010/0021990 A1 | 1/2010 | Edwards et al. |
| 2010/0028311 A1 | 2/2010 | Motlagh et al. |
| 2010/0042260 A1 | 2/2010 | Antwiler |
| 2010/0075410 A1 | 3/2010 | Desai et al. |
| 2010/0086481 A1 | 4/2010 | Baird et al. |
| 2010/0090971 A1 | 4/2010 | Choi et al. |
| 2010/0092536 A1 | 4/2010 | Hunter et al. |
| 2010/0093607 A1 | 4/2010 | Dickneite |
| 2010/0105138 A1 | 4/2010 | Dodd et al. |
| 2010/0111910 A1 | 5/2010 | Rakoczy |
| 2010/0129376 A1 | 5/2010 | Denhardt et al. |
| 2010/0129912 A1 | 5/2010 | Su et al. |
| 2010/0136091 A1 | 6/2010 | Moghe et al. |
| 2010/0144037 A1 | 6/2010 | Antwiler |
| 2010/0144634 A1 | 6/2010 | Zheng et al. |
| 2010/0183561 A1 | 7/2010 | Sakthivel et al. |
| 2010/0183585 A1 | 7/2010 | Van Zant et al. |
| 2010/0203020 A1 | 8/2010 | Ghosh |
| 2010/0230203 A1 | 9/2010 | Karayianni |
| 2010/0248366 A1 | 9/2010 | Fadeev et al. |
| 2010/0278933 A1 | 11/2010 | Sayeski et al. |
| 2010/0285453 A1 | 11/2010 | Goodrich |
| 2010/0285590 A1 | 11/2010 | Verfaillie et al. |
| 2010/0291180 A1 | 11/2010 | Uhrich |
| 2010/0291181 A1 | 11/2010 | Uhrich et al. |
| 2010/0297234 A1 | 11/2010 | Sugino et al. |
| 2010/0304427 A1 | 12/2010 | Faris et al. |
| 2010/0304482 A1 | 12/2010 | Deshayes et al. |
| 2010/0310524 A1 | 12/2010 | Bechor et al. |
| 2010/0316446 A1 | 12/2010 | Runyon |
| 2011/0060463 A1 | 3/2011 | Selker et al. |
| 2011/0085746 A1 | 4/2011 | Wong et al. |
| 2011/0111498 A1 | 5/2011 | Oh et al. |
| 2011/0129447 A1 | 6/2011 | Meretzki et al. |
| 2011/0129486 A1 | 6/2011 | Meiron |
| 2011/0143433 A1 | 6/2011 | Oh et al. |
| 2011/0159584 A1 | 6/2011 | Gibbons et al. |
| 2011/0171182 A1 | 7/2011 | Abelman |
| 2011/0171659 A1 | 7/2011 | Furcht et al. |
| 2011/0177595 A1 | 7/2011 | Furcht et al. |
| 2011/0212493 A1 | 9/2011 | Hirschel et al. |
| 2011/0256108 A1 | 10/2011 | Meiron et al. |
| 2011/0256160 A1 | 10/2011 | Meiron et al. |
| 2011/0293583 A1 | 12/2011 | Aberman |
| 2012/0028352 A1 | 2/2012 | Oh et al. |
| 2012/0051976 A1 | 3/2012 | Lu et al. |
| 2012/0058554 A1 | 3/2012 | Deshayes et al. |
| 2012/0064047 A1 | 3/2012 | Verfaillie et al. |
| 2012/0064583 A1 | 3/2012 | Edwards et al. |
| 2012/0086657 A1 | 4/2012 | Stanton, IV et al. |
| 2012/0089930 A1 | 4/2012 | Stanton, IV et al. |
| 2012/0118919 A1 | 5/2012 | Cianciolo |
| 2012/0122220 A1 | 5/2012 | Merchav et al. |
| 2012/0135043 A1 | 5/2012 | Maziarz et al. |
| 2012/0145580 A1 | 6/2012 | Paruit et al. |
| 2012/0156779 A1 | 6/2012 | Anneren et al. |
| 2012/0178885 A1 | 7/2012 | Kohn et al. |
| 2012/0189713 A1 | 7/2012 | Kohn et al. |
| 2012/0208039 A1 | 8/2012 | Barbaroux et al. |
| 2012/0219531 A1 | 8/2012 | Oh et al. |
| 2012/0219737 A1 | 8/2012 | Sugino et al. |
| 2012/0226013 A1 | 9/2012 | Kohn et al. |
| 2012/0231519 A1 | 9/2012 | Bushman et al. |
| 2012/0237557 A1 | 9/2012 | Lewitus et al. |
| 2012/0295352 A1 | 11/2012 | Antwiler |
| 2012/0308531 A1 | 12/2012 | Pinxteren et al. |
| 2012/0315696 A1 | 12/2012 | Luitjens et al. |
| 2013/0004465 A1 | 1/2013 | Aberman |
| 2013/0039892 A1 | 2/2013 | Aberman |
| 2013/0058907 A1 | 3/2013 | Wojciechowski et al. |
| 2013/0059383 A1 | 3/2013 | Dijkhuizen Borgart et al. |
| 2013/0101561 A1 | 4/2013 | Sabaawy |
| 2013/0143313 A1 | 6/2013 | Niazi |
| 2013/0157353 A1 | 6/2013 | Dijkhuizen Borgart et al. |
| 2013/0259843 A1 | 10/2013 | Duda et al. |
| 2013/0319575 A1 | 12/2013 | Mendyk |
| 2013/0323213 A1 | 12/2013 | Meiron et al. |
| 2013/0337558 A1 | 12/2013 | Meiron et al. |
| 2014/0004553 A1 | 1/2014 | Parker et al. |
| 2014/0017209 A1 | 1/2014 | Aberman et al. |
| 2014/0030805 A1 | 1/2014 | Kasuto et al. |
| 2014/0051162 A1 | 2/2014 | Nankervis |
| 2014/0051167 A1 | 2/2014 | Nankervis et al. |
| 2014/0112893 A1 | 4/2014 | Tom et al. |
| 2014/0186937 A1 | 7/2014 | Smith et al. |
| 2014/0193895 A1 | 7/2014 | Smith et al. |
| 2014/0193911 A1 | 7/2014 | Newby et al. |
| 2014/0242039 A1 | 8/2014 | Meiron et al. |
| 2014/0248244 A1 | 9/2014 | Danilkovitch et al. |
| 2014/0315300 A1 | 10/2014 | Oh et al. |
| 2014/0342448 A1 | 11/2014 | Nagels |
| 2015/0004693 A1 | 1/2015 | Danilkovitch et al. |
| 2015/0024492 A1 | 1/2015 | Antwiler |
| 2015/0104431 A1 | 4/2015 | Pittenger et al. |
| 2015/0111252 A1 | 4/2015 | Hirschel et al. |
| 2015/0125138 A1 | 5/2015 | Karnieli et al. |
| 2015/0140654 A1* | 5/2015 | Nankervis ............ C12N 5/0775 435/366 |
| 2015/0175950 A1 | 6/2015 | Hirschel et al. |
| 2015/0225685 A1 | 8/2015 | Hirschel et al. |
| 2015/0247122 A1 | 9/2015 | Tom et al. |
| 2015/0259749 A1 | 9/2015 | Santos et al. |
| 2016/0362650 A1 | 12/2016 | Wojciechowski et al. |
| 2016/0362652 A1 | 12/2016 | Page et al. |
| 2017/0267966 A1 | 9/2017 | Stanton, IV et al. |
| 2017/0335270 A1 | 11/2017 | Stanton, IV et al. |
| 2018/0010082 A1 | 1/2018 | Jaques et al. |
| 2018/0030398 A1 | 2/2018 | Castillo |
| 2018/0155668 A1 | 6/2018 | Hirschel et al. |
| 2019/0194628 A1 | 6/2019 | Rao et al. |

FOREIGN PATENT DOCUMENTS

| | | |
|---|---|---|
| DE | 3833925 A1 | 9/1989 |
| DE | 4007703 A1 | 9/1991 |
| DE | 10244859 A1 | 4/2004 |
| DE | 10327988 A1 | 7/2004 |
| DE | 102012200939 A1 | 7/2013 |
| EP | 0220650 A2 | 5/1987 |
| EP | 0201086 B1 | 1/1992 |
| EP | 0224734 B1 | 3/1992 |
| EP | 750938 A1 | 1/1997 |
| EP | 906415 A1 | 4/1999 |
| EP | 959980 A1 | 12/1999 |
| EP | 1007631 A1 | 6/2000 |
| EP | 1028737 A1 | 8/2000 |
| EP | 1028991 A1 | 8/2000 |
| EP | 1066052 A2 | 1/2001 |
| EP | 1066060 A2 | 1/2001 |
| EP | 1084230 A2 | 3/2001 |
| EP | 1147176 A1 | 10/2001 |
| EP | 1220611 A1 | 7/2002 |
| EP | 1223956 A1 | 7/2002 |
| EP | 1325953 A1 | 7/2003 |
| EP | 1437404 A1 | 7/2004 |
| EP | 1437406 A2 | 7/2004 |
| EP | 1447443 A1 | 8/2004 |
| EP | 1452594 A1 | 9/2004 |
| EP | 1062321 B1 | 12/2004 |
| EP | 1484080 A1 | 12/2004 |
| EP | 1498478 A1 | 1/2005 |
| EP | 1036057 B1 | 10/2005 |
| EP | 1605044 A2 | 12/2005 |
| EP | 1756262 A1 | 2/2007 |
| EP | 1771737 A1 | 4/2007 |
| EP | 1882030 A1 | 1/2008 |
| EP | 1908490 A1 | 4/2008 |
| EP | 1971679 A2 | 9/2008 |
| EP | 1991668 A2 | 11/2008 |
| EP | 2200622 A1 | 6/2010 |
| EP | 2208782 A2 | 7/2010 |
| EP | 2264145 A1 | 12/2010 |
| EP | 2027247 B1 | 1/2011 |
| EP | 2303293 A1 | 4/2011 |

(56) References Cited

FOREIGN PATENT DOCUMENTS

| | | |
|---|---|---|
| EP | 2311938 A1 | 4/2011 |
| EP | 2331957 A1 | 6/2011 |
| EP | 2334310 A2 | 6/2011 |
| EP | 2334783 A2 | 6/2011 |
| EP | 2361968 A1 | 8/2011 |
| EP | 2366775 A1 | 9/2011 |
| EP | 2465922 A2 | 6/2012 |
| EP | 2481819 A1 | 8/2012 |
| EP | 2548951 A1 | 1/2013 |
| EP | 2561066 A1 | 2/2013 |
| EP | 2575831 A1 | 4/2013 |
| EP | 2591789 A2 | 5/2013 |
| EP | 2624845 A2 | 8/2013 |
| EP | 2626417 A1 | 8/2013 |
| EP | 2641606 A1 | 9/2013 |
| EP | 2689008 A1 | 1/2014 |
| EP | 2694639 A1 | 2/2014 |
| EP | 2697362 A2 | 2/2014 |
| EP | 2739720 A1 | 6/2014 |
| EP | 2807246 A1 | 12/2014 |
| GB | 1414671 A | 11/1975 |
| GB | 2297980 A | 8/1996 |
| GB | 2360789 A | 10/2001 |
| HU | 3285 U | 5/2007 |
| JP | H02245177 A | 9/1990 |
| JP | H03047074 A | 2/1991 |
| JP | 2002-535981 | 10/2002 |
| JP | 2003/052360 A | 2/2003 |
| JP | 2003510068 A | 3/2003 |
| JP | 2005-508393 | 3/2005 |
| JP | 2005278564 A | 10/2005 |
| JP | 2007000038 A | 1/2007 |
| JP | 2010-523118 | 7/2010 |
| JP | 2012506257 A | 3/2012 |
| JP | 5548207 B2 | 7/2014 |
| JP | 5548207 B2 | 7/2014 |
| JP | 2019516029 A | 6/2019 |
| JP | 2019525765 A | 9/2019 |
| KR | 101228026 B1 | 1/2013 |
| KR | 20150002762 A | 1/2015 |
| KR | 101504392 B1 | 3/2015 |
| KR | 101548790 B1 | 8/2015 |
| KR | 101553040 B1 | 9/2015 |
| KR | 20170076679 A | 7/2017 |
| KR | 20180027501 A | 3/2018 |
| KR | 102027596 B1 | 10/2019 |
| KR | 20200034790 A | 3/2020 |
| KR | 20200058433 A | 5/2020 |
| MY | 115206 A | 4/2003 |
| WO | 86/02379 A1 | 4/1986 |
| WO | 88/01643 A1 | 3/1988 |
| WO | 89/12676 A1 | 12/1989 |
| WO | 90/02171 A1 | 3/1990 |
| WO | WO-9013306 A2 | 11/1990 |
| WO | WO-9105238 A1 | 4/1991 |
| WO | 91/07485 A1 | 5/1991 |
| WO | WO-9106641 A1 | 5/1991 |
| WO | WO-9109194 A1 | 6/1991 |
| WO | 91/10425 A1 | 7/1991 |
| WO | 92/10564 A1 | 6/1992 |
| WO | WO-94/25571 A1 | 11/1994 |
| WO | 95/04813 A1 | 2/1995 |
| WO | 95/21911 A1 | 8/1995 |
| WO | 95/24468 A1 | 9/1995 |
| WO | 95/27041 A1 | 10/1995 |
| WO | WO-96/29395 A1 | 9/1996 |
| WO | WO-96/39035 A1 | 12/1996 |
| WO | WO-97/05826 A1 | 2/1997 |
| WO | 97/16527 A1 | 5/1997 |
| WO | WO-97/29792 A1 | 8/1997 |
| WO | WO-97/39104 A1 | 10/1997 |
| WO | WO-1997-040137 A1 | 10/1997 |
| WO | 98/22588 A2 | 5/1998 |
| WO | WO-98/31403 A1 | 7/1998 |
| WO | 98/53046 A2 | 11/1998 |
| WO | WO-98/51317 A1 | 11/1998 |
| WO | WO-98/51785 A1 | 11/1998 |
| WO | WO-99/05180 A1 | 2/1999 |
| WO | WO-99/24391 A1 | 5/1999 |
| WO | WO-99/24490 A1 | 5/1999 |
| WO | WO-99/27167 A1 | 6/1999 |
| WO | WO-99/49015 A2 | 9/1999 |
| WO | WO-00/06704 A2 | 2/2000 |
| WO | WO-0009018 A1 | 2/2000 |
| WO | WO-00/16420 A1 | 3/2000 |
| WO | WO-00/17326 A1 | 3/2000 |
| WO | WO-00/29002 A2 | 5/2000 |
| WO | WO-0032225 A1 | 6/2000 |
| WO | WO-00/44058 A2 | 7/2000 |
| WO | 00/46354 A1 | 8/2000 |
| WO | WO-0054651 A2 | 9/2000 |
| WO | WO-0056405 A2 | 9/2000 |
| WO | WO-00/59933 A2 | 10/2000 |
| WO | WO-00/69449 A2 | 11/2000 |
| WO | 00/75275 A1 | 12/2000 |
| WO | WO-00/75196 A1 | 12/2000 |
| WO | WO 00/75275 | 12/2000 |
| WO | WO-00/77236 A2 | 12/2000 |
| WO | WO-2001/000783 A2 | 1/2001 |
| WO | WO-2001/011011 A2 | 2/2001 |
| WO | WO-2001/018174 A2 | 3/2001 |
| WO | WO-2001/021766 A2 | 3/2001 |
| WO | 01/23520 A1 | 4/2001 |
| WO | WO 01/23520 | 4/2001 |
| WO | WO-2001/025402 A1 | 4/2001 |
| WO | WO-2001/029189 A2 | 4/2001 |
| WO | WO-0122810 A2 | 4/2001 |
| WO | WO-2001/034167 A1 | 5/2001 |
| WO | WO-2001/049851 A1 | 7/2001 |
| WO | WO-2001/054706 A2 | 8/2001 |
| WO | WO-2001-094541 A2 | 12/2001 |
| WO | 02/28996 A1 | 4/2002 |
| WO | WO 02/28996 | 4/2002 |
| WO | WO-2002/042422 A2 | 5/2002 |
| WO | WO-2002/057430 A2 | 7/2002 |
| WO | WO-2002/092794 A2 | 11/2002 |
| WO | WO-2002/101385 A1 | 12/2002 |
| WO | WO-2003/010303 A1 | 2/2003 |
| WO | WO-2003/014313 A2 | 2/2003 |
| WO | WO-2003/016916 A1 | 2/2003 |
| WO | 03/024587 A1 | 3/2003 |
| WO | WO-2003/023018 A2 | 3/2003 |
| WO | WO-2003/023019 A1 | 3/2003 |
| WO | WO-2003/025167 A2 | 3/2003 |
| WO | WO-2003/029402 A2 | 4/2003 |
| WO | 03/039459 A2 | 5/2003 |
| WO | WO-2003/040336 A2 | 5/2003 |
| WO | WO-2003/042405 A2 | 5/2003 |
| WO | WO-2003/046161 A2 | 6/2003 |
| WO | WO-2003/055989 A2 | 7/2003 |
| WO | WO-2003/061685 A1 | 7/2003 |
| WO | WO-2003/061686 A1 | 7/2003 |
| WO | WO-2003/068961 A2 | 8/2003 |
| WO | WO-2003/072064 A2 | 9/2003 |
| WO | WO-2003/078609 A1 | 9/2003 |
| WO | WO-2003/078967 A2 | 9/2003 |
| WO | WO-2003/080816 A1 | 10/2003 |
| WO | WO-2003/082145 A2 | 10/2003 |
| WO | WO-2003/085099 A2 | 10/2003 |
| WO | WO-2003/089631 A1 | 10/2003 |
| WO | WO-2003/091398 A2 | 11/2003 |
| WO | WO-2003/095631 A1 | 11/2003 |
| WO | 03/105663 A2 | 12/2003 |
| WO | WO 03/105663 | 12/2003 |
| WO | WO-2004/001697 A1 | 12/2003 |
| WO | WO-2004/012226 A2 | 2/2004 |
| WO | WO-2004/016779 A1 | 2/2004 |
| WO | WO-2004/018526 A1 | 3/2004 |
| WO | WO-2004/018655 A2 | 3/2004 |
| WO | WO-2004/026115 A2 | 4/2004 |
| WO | WO-2004/029231 A1 | 4/2004 |
| WO | WO-2004/042023 A2 | 5/2004 |
| WO | WO-2004/042033 A2 | 5/2004 |
| WO | WO-2004/042040 A1 | 5/2004 |

(56) References Cited

FOREIGN PATENT DOCUMENTS

| | | |
|---|---|---|
| WO | WO-2004/044127 A2 | 5/2004 |
| WO | WO-2004/044158 A2 | 5/2004 |
| WO | WO-2004/046304 A1 | 6/2004 |
| WO | WO-2004/050826 A2 | 6/2004 |
| WO | WO-2004/053096 A2 | 6/2004 |
| WO | WO-2004/055155 A2 | 7/2004 |
| WO | WO-2004/056186 A1 | 7/2004 |
| WO | WO-2004/065616 A2 | 8/2004 |
| WO | WO-2004/069172 A2 | 8/2004 |
| WO | WO-2004/070013 A2 | 8/2004 |
| WO | WO-2004/072264 A2 | 8/2004 |
| WO | WO-2004/073633 A2 | 9/2004 |
| WO | WO-2004/074464 A1 | 9/2004 |
| WO | WO-2004/076642 A2 | 9/2004 |
| WO | WO-2004/076653 A1 | 9/2004 |
| WO | 2004/090112 A2 | 10/2004 |
| WO | WO-2004/087870 A2 | 10/2004 |
| WO | WO-2004/094588 A2 | 11/2004 |
| WO | WO-2004/096975 A2 | 11/2004 |
| WO | WO-2004/104166 A2 | 12/2004 |
| WO | WO-2004/106499 A1 | 12/2004 |
| WO | WO-2004/113513 A2 | 12/2004 |
| WO | WO-2005/001033 A2 | 1/2005 |
| WO | WO-2005/001081 A1 | 1/2005 |
| WO | WO-2005/003320 A2 | 1/2005 |
| WO | WO-2005/007799 A2 | 1/2005 |
| WO | WO-2005/010172 A2 | 2/2005 |
| WO | WO-2005/011524 A1 | 2/2005 |
| WO | WO-2005/012480 A2 | 2/2005 |
| WO | WO-2005/012510 A1 | 2/2005 |
| WO | WO-2005/012512 A1 | 2/2005 |
| WO | WO-05014775 A2 | 2/2005 |
| WO | WO-2005/028433 A2 | 3/2005 |
| WO | WO-05044972 A2 | 5/2005 |
| WO | WO-2005/056747 A2 | 6/2005 |
| WO | WO-05051316 A2 | 6/2005 |
| WO | WO-2005/063303 A1 | 7/2005 |
| WO | WO-2005/075636 A1 | 8/2005 |
| WO | 2005/087915 A2 | 9/2005 |
| WO | 2005/104755 A2 | 11/2005 |
| WO | WO-2005/107760 A1 | 11/2005 |
| WO | WO-2006/009291 A1 | 1/2006 |
| WO | 2006/026835 A1 | 3/2006 |
| WO | WO-2006/032075 A1 | 3/2006 |
| WO | WO-2006/032092 A1 | 3/2006 |
| WO | 2006/037022 A2 | 4/2006 |
| WO | WO-2006/108229 A1 | 10/2006 |
| WO | WO-2006/113881 A2 | 10/2006 |
| WO | WO-2006/121445 A2 | 11/2006 |
| WO | WO-06124021 A1 | 11/2006 |
| WO | WO-06129312 A2 | 12/2006 |
| WO | 2007/038572 A2 | 4/2007 |
| WO | 2007/059473 A2 | 5/2007 |
| WO | 2007/117765 A2 | 10/2007 |
| WO | WO-2007/115367 A1 | 10/2007 |
| WO | WO-2007/115368 A1 | 10/2007 |
| WO | 2007/136821 A1 | 11/2007 |
| WO | 2007/139742 A1 | 12/2007 |
| WO | 2007/139746 A1 | 12/2007 |
| WO | 2007/139747 A1 | 12/2007 |
| WO | 2007/139748 A1 | 12/2007 |
| WO | WO-2008/006168 A1 | 1/2008 |
| WO | WO-2008/011664 A1 | 1/2008 |
| WO | WO-2008/017128 A1 | 2/2008 |
| WO | WO-2008/028241 A1 | 3/2008 |
| WO | WO-08040812 A1 | 4/2008 |
| WO | 2008/073635 A2 | 6/2008 |
| WO | WO 2008/109674 | 9/2008 |
| WO | WO-2008/116261 A1 | 10/2008 |
| WO | WO-2008/149129 A1 | 12/2008 |
| WO | WO-2009/026635 A1 | 3/2009 |
| WO | WO 2009/034186 | 3/2009 |
| WO | WO-09058146 A1 | 5/2009 |
| WO | WO-09080054 A1 | 7/2009 |
| WO | WO-09081408 A2 | 7/2009 |
| WO | WO-2009/140452 A2 | 11/2009 |
| WO | WO-09132457 A1 | 11/2009 |
| WO | WO-2009/144720 A1 | 12/2009 |
| WO | WO-10005527 A1 | 1/2010 |
| WO | WO-2010/019886 A1 | 2/2010 |
| WO | WO-10014253 A2 | 2/2010 |
| WO | WO-10019997 A1 | 2/2010 |
| WO | WO-2010/026573 A1 | 3/2010 |
| WO | WO-2010/026574 A2 | 3/2010 |
| WO | WO-2010/026575 A2 | 3/2010 |
| WO | 2010/036760 A1 | 4/2010 |
| WO | WO-2010/059487 A1 | 5/2010 |
| WO | WO-10061377 A2 | 6/2010 |
| WO | WO-10068710 A2 | 6/2010 |
| WO | WO-10071826 A2 | 6/2010 |
| WO | WO-10083385 A2 | 7/2010 |
| WO | WO-10111255 A1 | 9/2010 |
| WO | WO-10119036 A1 | 10/2010 |
| WO | WO-10123594 A2 | 10/2010 |
| WO | WO-2011/025445 A1 | 3/2011 |
| WO | 2011/098592 A1 | 8/2011 |
| WO | 2011/130617 A2 | 10/2011 |
| WO | WO-2011/132087 A1 | 10/2011 |
| WO | WO-2011/147967 A1 | 12/2011 |
| WO | WO-2012/072924 A1 | 6/2012 |
| WO | WO-2012/127320 A1 | 9/2012 |
| WO | WO-2012/138968 A1 | 10/2012 |
| WO | WO-2012/140519 A2 | 10/2012 |
| WO | 2012/171026 A2 | 12/2012 |
| WO | 2012/171030 A2 | 12/2012 |
| WO | 2013/085682 A1 | 6/2013 |
| WO | WO-2013/110651 A1 | 8/2013 |
| WO | WO-2014/037862 A1 | 3/2014 |
| WO | WO-2014/037863 A1 | 3/2014 |
| WO | WO-2014/068508 A2 | 5/2014 |
| WO | WO-2014/128306 A1 | 8/2014 |
| WO | WO-2014/128634 A1 | 8/2014 |
| WO | WO-2014/131846 A1 | 9/2014 |
| WO | WO-2014/141111 A1 | 9/2014 |
| WO | WO-2015/004609 A2 | 1/2015 |
| WO | 2015/059714 A1 | 4/2015 |
| WO | 2015/069943 A1 | 5/2015 |
| WO | WO 2015/073913 | 5/2015 |
| WO | WO 2015/073918 | 5/2015 |
| WO | 2015/118148 A1 | 8/2015 |
| WO | 2015/118149 A1 | 8/2015 |
| WO | WO-2015/131143 A1 | 9/2015 |
| WO | 2016/130940 A1 | 8/2016 |
| WO | 2017/072201 A2 | 5/2017 |
| WO | 2017/158611 A1 | 9/2017 |
| WO | 2017/207822 A1 | 12/2017 |
| WO | 2018/183426 A1 | 10/2018 |
| WO | 2019/155032 A1 | 8/2019 |
| WO | 2019/238919 A1 | 12/2019 |
| WO | 2020/020569 A1 | 1/2020 |
| WO | 2020/079274 A1 | 4/2020 |

OTHER PUBLICATIONS

Cao et al. "The hollow fiber bioreactor as a stroma-supported, serum-free ex vivo expansion platform for human umbilical cord blood cells", Biotechnology Journal, 9:7 980-989 (Year: 2014).*

Smith et al., Expansion of CD34+KDR+ cells in cord blood after culture with TPO, FLT-3L, SCF, and VEGF, Abstracts/Experimental Hematology, 28, p. 94 (Year: 2000).*

Mandalam et al., Ex vivo expansion of bone marrow and cord blood cells to produce stem and progenitor cells for hematopoietic reconstruction, Military Medicine, 167, pp. 78-81 (Year: 2002).*

Alakel, et al. Direct contact with mesenchymal stromal cells affects migratory behavior and gene expression profile of CD133+ hematopoietic stem cells during ex vivo expansion, Experimental Hematology, 37, pp. 504-513, (Year: 2009).*

Lu et al., Galactosylated poly(vinylidene difluoride) hollow fiber bioreactor for hepatocyte culture, Tissue Engineering, 11(11/12): 1667-1677. (Year: 2005).*

Godara et al., Mini-review Design of bioreactors for mesenchymal stem cell tissue engineering, Journal of Chemical Technology and Biotechnology, 83:408-420. (Year: 2008).*

(56) References Cited

OTHER PUBLICATIONS

Shen et al., Residues 39-56 of stem cell factor protein sequence are capable of stimulating the expansion of cod blood CD34+ cells, PLOS One, 1-14. (Year: 2015).*
Cao et al., The hollow fiber bioreactor as a stroma-supported, serum-free ex vivo expansion platform for human umbilical cord blood cells, Biotechnology Journal, 9: 980-989. (Year: 2014).*
Yao et al., A systematic strategy to optimize ex vivo expansion medium for human hematopoietic stem cells derived from umbilical cord blood mononuclear cells, Experimental Hematology, 32: 720-727. (Year: 2004).*
Stemcell2max, media fact sheet. (Year: 2015).*
Abumiya et al., "Shear Stress Induces Expression of Vascular Endothelial Growth Factor Receptor Flk-1/KDR Through the CT-Rich Sp1 Binding Site," Ateriosclerosis, Thrombosis, and Vascular Biology, vol. 22, Jun. 2002, pp. 907-913.
Akiyama et al., "Ultrathin Poly(N-isopropylacrylamide) Grafted Layer on Polystyrene Surfaces for Cell Adhesion/Detachment Control," Langmuir, vol. 20, No. 13, May 26, 2004, pp. 5506-5511.
Akram et al., "Mesenchymal Stem Cells Promote Alveolar Epithelial Cell Wound Repair in vitro through Distinct Migratory and Paracrine Mechanisms," Respiratory Research, vol. 14, No. 9, 2013, pp. 1-16.
Anamelechi et al., "Streptavidin Binding and Endothelial Cell Adhesion to Biotinylated Fibronectin," Langmuir, vol. 23, No. 25, Dec. 4, 2007, pp. 12583-12588.
Azar et al., "Heart Rates of Male and Female Sprague-Dawley and Spontaneously Hypertensive Rats Housed Singly or in Groups," Journal of the American Association for Laboratory Animal Science, vol. 50, No. 2, Mar. 2011, pp. 175-184.
Baecher-Allan et al., "CD4+CD25high Regulatory Cells in Human Peripheral Blood," The Journal of Immunology, vol. 167, 2001, pp. 1245-1253.
Boitano et al., "Aryl Hydrocarbon Receptor Antagonists Promote the Expansion of Human Hematopoietic Stem Cells," Science, vol. 329, No. 5997, published Sep. 10, 2010. corrected May 6, 2011, pp. 1345-1348.
Brunstein et al., "Infusion of ex vivo Expanded T Regulatory Cells in Adults Transplanted with Umbilical Cord Blood: Safety Profile and Detection Kinetics," Blood, vol. 117, No. 3, Jan. 20, 2011, pp. 1061-1070.
Bryce et al., "In vitro Micronucleus Assay Scored by Flow Cytometry Provides a Comprehensive Evaluation of Cytogenetic Damage and Cytotoxicity," Mutation Research, vol. 630, Mar. 19, 2007, pp. 78-91.
Bryce et al., "Interlaboratory Evaluation of a Flow Cytometric, High Content in vitro Micronucleus Assay," Mutation Research, vol. 650, Jan. 7, 2008, pp. 181-195.
Camacho Villa et al., "CD133+CD34+ and CD133+CD38+ Blood Progenitor Cells as Predictors of Platelet Engraftment in Patients Undergoing Autologous Peripheral Blood Stem Cell Transplantation," Transfusion and Apheresis Science, vol. 46, 2012, pp. 239-244.
Cano et al., "Immobilization of endo-1,4-β-xylanase on Polysulfone Acrylate Membranes: Synthesis and Characterization," Journal of Membrane Science, vol. 280, Feb. 28, 2006, pp. 383-388.
Carvell et al., "Monitoring Live Biomass in Disposable Bioreactors," BioProcess International, vol. 14, No. 3, Mar. 2016, pp. 40-48.
Carvell et al., "On-line Measurements and Control of Viable Cell Density in Cell Culture Manufacturing Processes Using Radio Frequency Impedance," Cytotechnology, 2006, vol. 50, pp. 35-48.
Cuchiara et al., "Covalent Immobilization of SCF and SDF1α for in vitro Culture of Hematopoietic Progenitor Cells," Acta Biomaterials, vol. 9, No. 12, Dec. 2013, pp. 9258-9269.
Da Silva et al., "Smart Thermoresponsive Coatings and Surfaces for Tissue Engineering; Switching Cell-Material Boundaries," Trends in Biotechnology, vol. 15, No. 12, 2007, pp. 577-583.
Garlie et al., "T Cells Coactivated with Immobilized Anti-CD3 and Anti-CD28 as Potential Immunotherapy for Cancer," Journal of Immunotherapy, vol. 22, No. 4, 1999, pp. 336-345.

The Effect of Rocking Rate and Angle on T Cell Cultures Grown in XuriTM Cell Expansion Systems, GE Healthcare UK Limited, Cell therapy bioreactor systems, Application note 29-1166-55 AA, Aug. 2014, www.gelifesciences.com/xuri.
Hao et al., "A Functional Comparison of CD34+ CD38− Cells in Cord Blood and Bone Marrow," Blood, vol. 86, No. 10, Nov. 15, 1995, pp. 3745-3753.
Harimoto et al., "Novel Approach for Achieving Double-Layered Cell Sheets Co-Culture: Overlaying Endothelial Cell Sheets onto Monolayer Hepatocytes Utilizing Temperature-Responsive Culture Dishes," Journal of Biomedical Material Research, vol. 62, 2002, pp. 464-470.
Högstedt et al., "Frequency and Size Distribution of Micronuclei in Lymphocytes Stimulated with Phytohemagglutinin and Pokeweed Mitogen in Workers Exposed to Piperazine," Hereditas, vol. 109, 1998, pp. 139-142.
Infanger et al., "Simulated weightlessness changes the cytoskeleton and extracellular matrix proteins in papillary thyroid carcinoma cells", Cell and Tissue Research, vol. 324, No. 2, 2006, pp.
Itkin et al., "SDF-1 Keeps HSC Quiescent at Home," Blood, vol. 117, No. 2, Jan. 13, 2011, pp. 373-374.
Jang et al., "Syndecan-4 Proteoliposomes Enhance Fibroblast Growth Factor-2 (FGF-2)-Induced Proliferation, Migration, and Neovascularization of Ischemic Muscle," PNAS, vol. 109, No. 5, Jan. 31, 2012, pp. 1679-1684.
Johansson et al., "Pancreatic Islet Survival and Engraftment Is Promoted by Culture on Functionalized Spider Silk Matrices," PLoS One, Jun. 19, 2015, pp. 1-21.
Jones et al., "Genetic stability of bone marrow-derived human mesenchymal stromal cells in the Quantum System", Cytotherapy, 2013; 15: 1323-1339.
Klein et al., "Affinity Membranes Prepared from Hydrophilic Coatings on Microporous Polysulfone Hollow Fibers," Journal of Membrane Science, vol. 90, 1994, pp. 69-80.
Koestenbauer et al., "Protocols for Hematopoietic Stem Cell Expansion from Umbilical Cord Blood," Cell Transplantation, vol. 18, May 6, 2009, pp. 1059-1068.
Koller et al., "Clinical-scale Human Umbilical Cord Blood Cell Expansion in a Novel Automated Perfusion Culture System," Bone Marrow Transplantation, vol. 21, 1998, pp. 653-663.
Lang et al., "Generation of Hematopoietic Humanized Mice in the Newborn BALB/C-Rag2null Il2rynull Mouse Model: A Multivariable Optimization Approach," Clinical Immunology, vol. 140, Apr. 14, 2011, pp. 102-116.
Lataillade et al., "Chemokine SDF-1 Enhances Circulating CD341 Cell Proliferation in Synergy with Cytokines: Possible Role in Progenitor Survival," Blood, vol. 95, No. 3, Feb. 1, 2000, pp. 756-768.
Li et al., "Heparin-induced Conformation Changes of Fibronectin within the Extracellular Matrix Promote hMSC Osteogenic Differentiation," Biomaterials Science, vol. 3, 2015, pp. 73-84.
Liu et al., "Ex vivo Expansion of Hematopoietic Stem Cells Derived from Umbilical Cord Blood in Rotating Wall Vessel", Journal of Biotechnology, 2006, 124:592-601. Abstract only.
Malin et al., "Noninvasive Prediction of Glucose by Near-Infrared Diffuse Reflectance Spectroscopy," Clinical Chemistry, vol. 45, No. 9, 1999, pp. 1651-1658.
Marek-Trzonkowska et al., "Administration of CD4+ CD25high CD127-Regulatory T Cells Preserves β-Cell Function in Type 1 Diabetes in Children," Diabetes Care, vol. 35, No. 9, Sep. 2012, pp. 1817-1820.
Murugappan et al., "Human Hematopoietic Progenitor Cells Grow Faster under Rotational Laminar Flows," Biotechnology Progress—Cell Culture & Tissue Engineering, Online, Apr. 22, 2010.
Nankervis et al., "Shear Stress Conditions in the Quantum Cell Expansion System", Poster Session—TERMIS AM Annual Conference 2013, Nov. 12, 2013.
Nelson et al., "Emergent Patterns of Growth Controlled by Multicellular Form and Mechanics," PNAS, vol. 102, No. 33, Aug. 16, 2005, pp. 11594-11599.

(56) References Cited

OTHER PUBLICATIONS

Nguyen et al., "QUANTUM® Cell Expansion System: Automated Expansion of Human Mesenchymal Stem Cells from Precultured Cells Using the Quantum Cell Expansion System", Terumo BCT, Inc., 2012.
Nicolette et al., "In Vitro Micronucleus Screening of Pharmaceutical Candidates by Flow Cytometry in Chinese Hamster V79 Cells," Environmental and Molecular Mutagenesis, vol. 52, Oct. 20, 2010, pp. 355-362.
Nugent et al., "Adventitial Endothelial Implants Reduce Matrix Metalloproteinase-2 Expression and Increase Luminal Diameter in Porcine Arteriovenous Grafts," Journal of Vascular Surgery, vol. 46, No. 3, Sep. 2007, pp. 548-556.e2.
Okano et al., "Mechanism of Cell Detachment from Temperature-Modulated, Hydrophilic-Hydrophobic Polymer Surfaces," Biomaterials, vol. 16, No. 4, 1995, pp. 297-303.
Putnam et al., "Expansion of Human Regulatory T-Cells from Patients with Type 1 Diabetes," Diabetes, vol. 58, Mar. 2009, pp. 652-662.
Rodrigues et al., "Stem Cell Cultivation in Bioreactors," Biotechnology Advances, vol. 29, Jun. 25, 2011, pp. 815-829.
Ronco et al., "Blood and Dialysate Flow Distributions in Hollow-Fiber Hemodialyzers Analyzed by Computerized Helical Scanning Technique," Journal of the American Society of Nephrology, vol. 13, 2002, pp. S53-S61.
Ryu et al., "Near-infrared Light Responsive Synthetic c-di-GMP Module for Optogenetic Applications," ACS Synthetic Biology, vol. 3, Jan. 28, 2014, pp. 802-810.
Shimizu et al., "Fabrication of Pulsatile Cardiac Tissue Grafts Using a Novel 3-Dimensional Cell Sheet Manipulation Technique and Temperature-Responsive Cell Culture Surfaces," Circulation Research, vol. 90, Feb. 22, 2002, e40-e48, pp. 1-9.
Smith et al., "Expansion of Neutrophil Precursors and Progenitors in Suspension Cultures of CD34+ Cells Enriched from Human Bone Marrow," Experimental Hematology, vol. 21, 1993, pp. 870-877.
Takezawa et al., "Cell Culture on a Thermo-responsive Polymer Surface," Nature, Bio/Technology, vol. 8, Sep. 1990, pp. 854-856.
Tiziani et al., "Metabolomic Profiling of Drug Response in Acute Myeloid Leukaemia Cell lines," PLoS One, vol. 4, Issue 1, Jan. 22, 2009, e4251.
Ueda et al., "Interaction of Natural Killer Cells with Neutrophils Exerts a Significant Antitumor Immunity in Hematopoietic Stem Cell Transplantation Recipients," Cancer Medicine, vol. 5, No. 1, 2016 pp. 49-60.
Urbich et al., "Fluid Shear Stress-induced Transcriptional Activation of the Vascular Endothelial Growth Factor Receptor-2 Gene Requires Sp1-Dependent DNA Binding," FEBS Letters, 535, 2003, pp. 87-93.
Von Laer, "Loss of CD38 Antigen on CD34 CD38 Cells during Short-term Culture," Leukemia, Correspondence, 1999 pp. 947-948.
Wagner et al., "Phase I/II Trial of StemRegenin-1 Expanded Umbilical Cord Blood Hematopoietic Stem Cells Supports Testing as a Stand-alone Graft," Cell Stem Cell, Jan. 7, 2016, vol. 18, pp. 144-155.
Weaver et al., "An Analysis of Engraftment Kinetics as a Function of the CD34 Content of the Peripheral Blood Progenitor Cell Collections in 692 Patients after the Administration of Myeloblative Chemotherapy," Blood, vol. 86, No. 10, Nov. 15, 1995, pp. 3691-3969.
Yang et al., "Suspension Culture of Mammalian Cells Using Thermosensitive Microcarrier that Allows Cell Detachment without Proteolytic Enzyme Treatment," Cell Transplantation, vol. 19, Aug. 18, 2010, pp. 1123-1132.
Yi et al., "A Readily Modified Polyethersulfone with Amino-Substituted Groups: Its Amphiphilio Copolymer Synthesis and Membrane Application," Polymer, vol. 53, Dec. 2, 2011, pp. 350-358.
Zheng et al., "Differential Effects of Cyclic and Static Stretch on Coronary Microvascular Endothelial Cell Receptors and Vasculogenic/ Angiogenic Responses," American Journal of Physiology—Heart and Circulatory Physiology, vol. 295, Aug. 2008, H794-H800.
Biovest International, "AutovaxID(TM): advanced hollow fibre bioreactors with automated lactate control yield higher density monoclonal antibody production", VWRbioMarke, No. 21, Sep. 2008, pp. 10-11.
Chang et al., "Membrane Bioreactors: Present and Prospects", Advances in Biochemical Engineering, 1991, vol. 44, pp. 27-64.
Chang, Ho Nam, "Membrane Bioreactors: Engineering Aspects", Biotech. Adv., 1987, vol. 5, pp. 129-145.
Clausen et al., "Lactate as an Indicator of Terminating Time in Insect Cell Culture Baculovirus Expression Vector Systems", Biotechnology Techniques, vol. 10, No. 10, Oct. 1996, pp. 721-726.
Edgington, Stephen M., "New Horizons for Stem-Cell Bioreactors", Biotechnology, Oct. 1992, vol. 10, pp. 1099-1106.
Gastens et al., "Good Manufacturing Practice-Compliant Expansion of Marrow-Derived Stem and Progenitor Cells for Cell Therapy", Cell Transplantation, 2007, vol. 16, pp. 685-696.
Gerlach, J.C. et al., "Comparison of hollow fibre membranes for hepatocyte immobilization in bioreactors," The International Journal of Artificial Organs, 1996, vol. 19 No. 10, pp. 610-616.
Gloeckner et al., "New Miniaturized Hollow-Fiber Bioreacter for in Vivo Like Cell Culture, Cell Expansion, and Production of Cell-Derived Products", Biotechnol. Prog., Aug. 21, 2001, vol. 17, No. 5, pp. 828-831.
Gramer et al., "Screening Tool for Hollow-Fiber Bioreactor Process Development", Biotechnol. Prog., 1998, vol. 14, pp. 203-209.
Grayson et al., "Effects of Hypoxia on Human Mesenchymal Stem Cell Expansion and Plasticity in 3D Constructs", J. Cellular Physiology, 2006, 207:331-339.
Hirschel et al., "An Automated Hollow Fiber System for the Large Scale Manufacture of Mammalian Cell Secreted Product", Large Scale Cell Culture Technology, ed. Bjorn K. Lydersen, Hanser Publishers, 1987, pp. 113-144.
Lloyd, J.R. et al., "Hollow-Fibre bioreactors compared to batch and chemostat culture for the production of a recombinant toxoid by a marine Vibrio," Appl. Microbiol Biotechnol, Aug. 1997, vol. 48, pp. 155-161.
Neumann, Detlef et al., "Bioreaktorsteurung mit grafischer Bedienoberflache," ATP Automatisierungstechnische Praxis, Mar. 1995, pp. 16-23, vol. 37, No. 3, Munchen, DE. (English language translation included).
Nielsen, Lars Keld, "Bioreactors for Hematopoietic Cell Culture", Annu. Rev. Biomed. Eng., 1999, vol. 1, pp. 129-152.
Ozturk et al., "Real-Time Monitoring and Control of Glucose and Lactate Concentrations in a Mammalian Cell Perfusion Reactor", Biotechnology and Bioengineering, vol. 53, No. 4, Feb. 20, 1997, pp. 372-378.
Pörtner et al., "An Overview on Bioreactor Design, Prototyping and Process Control for Reproducible Three-Dimensional Tissue Culture", Drug Testing in Vitro: Breakthroughs and Trends in Cell Culture Technology, ed. Uwe Marx and Volker Sandig, 2007, Wiley-VCH, pp. 53-78.
Sauer, I. et al., "Extracorporeal liver support based on primary human liver cells and albumin dialysis—treatment of patient with primary graft non function," Journal of Hepatology, Oct. 2003, vol. 39 No. 4, pp. 649-653.
Wang et al., "Influence of Oxygen on the Proliferation and Metabolism of Adipose Derived Adult Stem Cells", J. Cellular Physiology, 2005, 204:184-161.
Zhao et al., "Effects of Oxygen Transport on 3-D Human Mesenchymal Stem Cell Metabolic Activity in Perfusion and Static Cultures: Experiments and Mathematical Model", Biotechnol. Prog., 2005, 21, 1269-1280.
Zhao et al., "Perfusion Bioreactor System for Human Mesenchymal Stem Cell Tissue Engineering: Dynamic Cell Seeding and Construct Development", Biotechnology and Bioengineering, Aug. 20, 2005, vol. 91, No. 4, pp. 482-493.
Official Action (with English translation) for Japan Patent Application No. 2018-561526, dated Dec. 22, 2022, 11 pages.
Afzali B, Edozie FC, Fazekasova H, Scotta C, Mitchell PJ, Canavan JB, Kordasti SY, Chana PS, Ellis R, Lord GM, John S, Hilton R, Lechler RI, Lombardi G. Comparison of regulatory T cells in

(56) References Cited

OTHER PUBLICATIONS hemodialysis patients and healthy controls: implications for cell therapy in transplantation. Clin J Am Soc Nephrol. 2013;8(8):1396-405.
Alberts B, Johnson A, Lewis J, et al. Molecular Biology of the Cell. 4th edition. New York: Garland Science; 2002. Fibroblasts and Their Transformations: The Connective-Tissue Cell Family. Available from: https://www.ncbi.nlm.nih.gov/books/NBK26889.
Alenazi, Noof A., et al. "Modified polyether-sulfone membrane: A mini review." Designed monomers and polymers 20.1 (2017): 532-546.
Almeida L, Lochner M, Berod L, Sparwasser T. Metabolic pathways in T cell activation and lineage differentiation. Semin Immunol. 2016;28(5):514-524.
Amy Putnam, Todd M. Brusko, Michael R. Lee, Weihong Liu, Gregory L. Szot, Taumoha Ghosh, Mark A. Atkinson, and Jeffrey A. Bluestone. Expansion of human regulatory T-Cells from patients with Type 1 Diabetes. Diabetes, 58: 652-662, 2009.
Anurathapan et al., "Engineered T cells for cancer treatment," Cytotherapy, vol. 16, pp. 713-733, 2014.
Aronowski J, Samways E, Strong R, Rhoades HM, Grotta JC. An alternative method for the quantitation of neuronal damage after experimental middle cerebral artery occlusion in rats: Analysis of behavioral deficit. Journal of cerebral blood flow and metabolism : official journal of the International Society of Cerebral Blood Flow and Metabolism. 1996; 16:705-713.
Arrigoni, Chiara, et al. "Rotating versus perfusion bioreactor for the culture of engineered vascular constructs based on hyaluronic acid." Biotechnology and bioengineering 100.5 (2008): 988-997.
Bai, Tao, et al. "Expansion of primitive human hematopoietic stem cells by culture in a zwitterionic hydrogel." Nature medicine 25.10 (2019): 1566-1575.
Bai/Delaney (Nohla Therapeutics) showed that expanding Cord Blood-derived CD34+CD38-CD45RA-HSPCs in a biodegradable zwitterionic hydrogel with a rNotch ligand cocktail for 24 days mitigated HSPC differentiation and promoted self-renewal of lymphoid and myeloid cell phenotypes in an NSG mouse model (Nature Medicine, 2019).
Ballas CB, Zielske SP, Gerson SL (2002) Adult bone marrow stem cells for cell and gene therapies: implications for greater use. J Cell Biochem Suppl 38: 20-28.
Ballke C, Gran E, Baekkevold ES, Jahnsen FL. Characterization of Regulatory T-Cell Markers in CD4+ T Cells of the Upper Airway Mucosa. PLoS One. 2016;11(2):e0148826.
Baraniak PR, McDevitt TC (2010) Stem cell paracrine actions and tissue regeneration. Regen Med 5(1): 121-143.
Barckhausen C, Rice B, Baila S, et al. (2016) GMP-Compliant Expansion of Clinical-Grade Human Mesenchymal Stromal/Stem Cells Using a Closed Hollow Fiber Bioreactor. Methods Mol Biol 1416: 389-412.
Barker et al. "CD34+ Cell Content of 126 341 Cord Blood Units in the US Inventory: Implications for Transplantation and Banking," blood Advances, vol. 3, No. 8, pp. 1267-1271, Apr. 23, 2019.
Barker, Juliet N., et al. "CD34+ cell content of 126 341 cord blood units in the US inventory: implications for transplantation and banking." Blood advances 3.8 (2019): 1267-1271.
Bazarian JJ, Cernak I, Noble-Haeusslein L, Potolicchio S, Temkin N. Long-term neurologic outcomes after traumatic brain injury. The Journal of head trauma rehabilitation. 2009;24:439-451.
Bending D, Pesenacker AM, Ursu S, Wu Q, Lom H, Thirugnanabalan B, Wedderburn LR. Hypomethylation at the regulatory T cell-specific demethylated region in CD25hi T cells is decoupled from FOXP3 expression at the inflamed site in childhood arthritis. J Immunol. 2014;193(6):2699-708.
Berendse M, Grounds MD, Lloyd CM (2003) Myoblast structure affects subsequent skeletal myotube morphology and sarcomere assembly. Exp Cell Res 291(2): 435-450.
Bernard, A., Payton, Mar. 1995. "Fermentation and Growth of Escherichia coli for Optimal Protein Production".
Berney SM, Schaan T, Wolf RE, van der Heyde H, Atkinson TP. CD2 (OKT11) augments CD3-mediated intracellular signaling events in human T lymphocytes. J Investig Med. 2000;48(2):102-9.
Bioheart Clinical Trial Clinica 1302 Apr. 18, 2008.
Biomolecular and Cellular Interactions with the Hollow Fiber Membrane Currently Used in the Quantum® Cell Expansion System. 12th NJ Symposium on Biomaterials Science, Oct. 6-7, 2014, New Brunswick, NJ.
Blache C, Chauvin JM, Marie-Cardine A, Contentin N, Pommier P, Dedreux I, Francois S, Jacquot S, Bastit D, Boyer O. Reduced frequency of regulatory T cells in peripheral blood stem cell compared to bone marrow transplantations. Biol Blood Marrow Transplant. 2010;16(3):430-4.
Bluestone et al. Type 1 diabetes immunotherapy using polyclonal regulatory T cells. Science Translational Medicine 7(315):1-34, 2015.
Bluestone JA, Tang Q. Treg cells-the next frontier of cell therapy. Science. 2018;362(6411):154-155.
Bluestone, Jeffrey A., et al. "Type 1 diabetes immunotherapy using polyclonal regulatory T cells." Science translational medicine 7.315 (2015): 315ra189-315ra189.
Blum S, Moore AN, Adams F, Dash Pk. A mitogen-activated protein kinase cascade in the ca1/ca2 subfield of the dorsal hippocampus is essential for long-term spatial memory. The Journal of neuroscience : the official journal of the Society for Neuroscience. 1999;19:3535-3544.
Bojun Li et al. Heparin-induced conformation changes of fibronectin within the extracellular matrix promote hMSC osteogenic differentiation. Biomaterials Science 3: 73-84, 2015.
Boquest AC, Shahdadfar A, Brinchmann JE, Collas P. Isolation of Stromal Stem Cells from Human Adipose Tissue. Methods Mol Biol. 2006;325:35-46. doi: 10.1385/1-59745-005-7:35. PMID: 16761717.
Borden, M. and Longo, M., "Dissolution Behavior of Lipid Monolayer-Coated, Air-Filled Microbubbles: Effect of Lipid Hydrophobic Chain Length," Langmuir, vol. 18, pp. 9225-9233, 2002.
Bourke, Sharon L., and Joachim Kohn. "Polymers derived from the amino acid L-tyrosine: polycarbonates, polyarylates and copolymers with poly (ethylene glycol)." Advanced drug delivery reviews 55.4 (2003): 447-466.
Brand, K. and Hermfisse, U., "Aerobic Glycolysis by Proliferating Cells: a Protective Strategy against Reactive Oxygen Species," The FASEB Journal, vol. 11, pp. 388-395, Apr. 1997.
Brentjens et al., "CD19-Targeted T Cells Rapidly Induce Molecular Remission in Adults with Chemotherapy-Refractory Acute Lympohblastic Leukemia," Science Translational Medicine, vol. 5, Issue 177, pp. 1-9, Mar. 20, 2013.
Brentjens et al., "Safety and Persistance of Adoptively Transferred Autologous CD19-Target T Cells in Patients with Relapsed or Chemotherapy Refractory B-Cell Leukemias," Blood, vol. 118, No. 18, pp. 4817-4828, Nov. 3, 2011.
C. H. Weaver, et al. An Analysis of Engraftment Kinetics as a function of the CD34 Content of the Peripheral Blood Progenitor Cell Collections in 692 Patients After the Administration of Myeloblative Chemotherapy. Blood 86(10): 3691-3969, 1995.
Carswell, K. and Papoutsakis, E. "Culture of Human T Cells in Stirred Bioreactors for Cellular Immunotherapy Applications: Shear, Proliferation, and the IL-2 Receptor," Biotechnology and Bioengineering, vol. 68, No. 3, pp. 329-338, May 5, 2000.
Celeste Nelson et al., Emergent patterns of growth controlled by multicellular form and mechanics, (in Christopher Chen's Lab demonstrated, in separate experiments, that curved surfaces with a radius of curvature (200 ?m) that is greater than the cell diameter and surfaces that have undulating special patterning (depressions) increase the patterned growth of ECs [PNAS 102(33): 11594-11599, 2005].
Chapman NM, Chi H. mTOR signaling, Tregs and immune modulation. Immunotherapy. 2014;6(12):1295-311.
Chaudhry A, Samstein RM, Treuting P, Liang Y, Pils MC, Heinrich JM, Jack RS, Wunderlich FT, Bruning JC, Muller W, Rudensky AY. Interleukin-10 signaling in regulatory T cells is required for suppression of Th17 cell-mediated inflammation. Immunity. 2011;34(4):566-78.

(56) References Cited

OTHER PUBLICATIONS

Chen, C. and Broden, M., "The Role of Poly(theylene glycol) Brush Architecture in Complement Activation on Targeted Microbubble Surfaces," Biomaterials, vol. 32, No. 27, pp. 6579-6587, Jun. 17, 2011.

Choi W, Kwon SJ, Jin HJ, et al. (2017) Optimization of culture conditions for rapid clinical-scale expansion of human umbilical cord blood-derived mesenchymal stem cells. Clin Transl Med 6(1): 38.

Chullikana A, Majumdar AS, Gottipamula S, et al. (2015) Randomized, double-blind, phase I/II study of intravenous allogeneic mesenchymal stromal cells in acute myocardial infarction. Cytotherapy 17(3): 250-261.

Claudio G. Brunstein, Jeffrey S. Miller, Qing Cao, Daivd H. Mckenna, Keli L. Hippen, Julie Curtsinger, Todd Defor, Bruce L. Levine, Carl H. June, Pablo Rubinstein, Philip B. McGlave, Bruce R. Blazar, and John E. Wagner. Infusion of ex vivo expanded T regulatory cells in adults transplanted with umbilical cord blood: safety profile and detection kinetics. Blood, 117(3): 1061-1070, 2010.

Coeshott C, Vang B, Jones M, Nankervis B. Large-scale expansion and characterization of CD3(+) T-cells in the Quantum((R)) Cell Expansion System. J Transl Med. 2019;17(1):258.

Coombes JL, Robinson NJ, Maloy KJ, Uhlig HH, Powrie F. Regulatory T cells and intestinal homeostasis. Immunol Rev. 2005;204:184-94.

Coquillard C. mTOR Signaling in Regulatory T cell Differentiation and Expansion. SOJ Immunology. 2015;3(1):1-10.

Creed JA, DiLeonardi AM, Fox DP, Tessler AR, Raghupathi R. Concussive brain trauma in the mouse results in acute cognitive deficits and sustained impairment of axonal function. Journal of neurotrauma. 2011;28:547-563.

Dash PK, Hochner B, Kandel ER. Injection of the camp-responsive element into the nucleus of aplysia sensory neurons blocks long-term facilitation. Nature. 1990;345:718-721.

Dash PK, Johnson D, Clark J, Orsi SA, Zhang M, Zhao J, Grill RJ, Moore AN, Pati S. Involvement of the glycogen synthase kinase-3 signaling pathway in tbi pathology and neurocognitive outcome. PloS one. 2011;6:e24648.

Dash PK, Mach SA, Blum S, Moore AN. Intrahippocampal wortmannin infusion enhances long-term spatial and contextual memories. Learn Mem. 2002;9:167-177.

Dash PK, Orsi SA, Zhang M, Grill RJ, Pati S, Zhao J, Moore AN. Valproate administered after traumatic brain injury provides neuroprotection and improves cognitive function in rats. PloS one. 2010;5:e11383.

Dash PK, Zhao J, Orsi SA, Zhang M, Moore AN. Sulforaphane improves cognitive function administered following traumatic brain injury. Neuroscience letters. 2009;460:103-107.

Davila et al., "Efficacy and Toxicity Management of 19-28z CAR T Cell Therapy in B cell Acute Lymphoblastic Leukemia," Science Translational Medicine, vol. 6, No. 224, pp. 1-10, Feb. 19, 2014.

Dejana E, Orsenigo F, Lampugnani MG. The role of adherens junctions and ve-cadherin in the control of vascular permeability. Journal of cell science. 2008;121:2115-2122.

Dejana E, Spagnuolo R, Bazzoni G. Interendothelial junctions and their role in the control of angiogenesis, vascular permeability and leukocyte transmigration. Thrombosis and haemostasis. 2001;86:308-315.

Dejana E, Tournier-Lasserve E, Weinstein BM. The control of vascular integrity by endothelial cell junctions: Molecular basis and pathological implications. Developmental cell. 2009;16:209-221.

Del Pino A, Ligero G, Lopez MB, et al. (2015) Morphology, cell viability, karyotype, expression of surface markers and plasticity of three primary cell line cultures before and after the cryostorage in LN2 and GN2. Cryobiology 70(1): 1-8.

Delaney, Colleen, et al. "Notch-mediated expansion of human cord blood progenitor cells capable of rapid myeloid reconstitution." Nature medicine 16.2 (2010): 232-236.

Ding, Zhongli, Guohua Chen, and Allan S. Hoffman. "Synthesis and purification of thermally sensitive oligomer? enzyme conjugates of poly (N-isopropylacrylamide)? trypsin." Bioconjugate chemistry 7.1 (1996): 121-125.

Dixon CE, Clifton GL, Lighthall JW, Yaghmai AA, Hayes RL. A controlled cortical impact model of traumatic brain injury in the rat. Journal of neuroscience methods. 1991;39:253-262.

Dominici M, Le Blanc K, Mueller I, et al. (2006) Minimal criteria for defining multipotent mesenchymal stromal cells. The International Society for Cellular Therapy position statement. Cytotherapy 8(4): 315-317.

Durrani S, Konoplyannikov M, Ashraf M, Haider KH (2010) Skeletal myoblasts for cardiac repair. Regen Med 5(6): 919-932.

Esensten JH, Muller YD, Bluestone JA, Tang Q. Regulatory T-cell therapy for autoimmune and autoinflammatory diseases: The next frontier. J Allergy Clin Immunol. 2018;142(6):1710-1718.

Fakin R, Hamacher J, Gugger M, Gazdhar A, Moser H, Schmid RA. Prolonged amelioration of acute lung allograft rejection by sequential overexpression of human interleukin-10 and hepatocyte growth factor in rats. Exp Lung Res. 2011;37(9):555-62.

Fedorov et al., "PD-1- and CTLA-4-Based Inhibitory Chimeric Antigen Receptors (iCARs) Divert Off-Target Immunotherapy Responses," Science Translational Medicine, vol. 5, No. 215, pp. 1-12, Dec. 11, 2013.

Ferreira LMR, Muller YD, Bluestone JA, Tang Q. Next-generation regulatory T cell therapy. Nat Rev Drug Discov. 2019;18(10):749-769.

Fischbach, Michael A., Jeffrey A. Bluestone, and Wendell A. Lim. "Cell-based therapeutics: the next pillar of medicine." Science translational medicine 5.179 (2013): 179ps7-179ps7.

Fisk, Nicholas M., et al. "Can routine commercial cord blood banking be scientifically and ethically justified?." PLoS medicine 2.2 (2005): e44.

Forbes Jun. 23, 2014 article "Will this man cure cancer?".

Fowler DH. Rapamycin-resistant effector T-cell therapy. Immunol Rev. 2014;257(1):210-25.

Fraser H, Safinia N, Grageda N, Thirkell S, Lowe K, Fry LJ, Scotta C, Hope A, Fisher C, Hilton R, Game D, Harden P, Bushell A, Wood K, Lechler RI, Lombardi G. A Rapamycin-Based GMP-Compatible Process for the Isolation and Expansion of Regulatory T Cells for Clinical Trials. Mol Ther Methods Clin Dev. 2018;8:198-209.

Frauwirth KA, Riley JL, Harris MH, Parry RV, Rathmell JC, Plas DR, Elstrom RL, June CH, Thompson CB. The CD28 signaling pathway regulates glucose metabolism. Immunity. 2002;16(6):769-77.

Fuchs A, Gliwinski M, Grageda N, Spiering R, Abbas AK, Appel S, Bacchetta R, Battaglia M, Berglund D, Blazar B, Bluestone JA, Bornhauser M, Ten Brinke A, Brusko TM, Cools N, Cuturi MC, Geissler E, Giannoukakis N, Golab K, Hafler DA, van Ham SM, Hester J et al. Minimum Information about T Regulatory Cells: A Step toward Reproducibility and Standardization. Front Immunol. 2017;8:1844.

G0211: Study for Gamma Irradiation of Bioreactor Membranes, undated, author unknown, 3 pages.

Galgani M, De Rosa V, La Cava A, Matarese G. Role of Metabolism in the Immunobiology of Regulatory T Cells. J Immunol. 2016;197(7):2567-75.

Gedaly R, De Stefano F, Turcios L, Hill M, Hidalgo G, Mitov MI, Alstott MC, Butterfield DA, Mitchell HC, Hart J, Al-Attar A, Jennings CD, Marti F. mTOR Inhibitor Everolimus in Regulatory T Cell Expansion for Clinical Application in Transplantation. Transplantation. 2019;103(4):705-715.

Gimble, Jeffrey M., Adam J. Katz, and Bruce A. Bunnell. "Adipose-derived stem cells for regenerative medicine." Circulation research 100.9 (2007): 1249-1260.

Gingras AC, Raught B, Sonenberg N. Regulation of translation initiation by FRAP/mTOR. Genes Dev. 2001; 15(7):807-26.

Godin, Michel, et al. "Measuring the mass, density, and size of particles and cells using a suspended microchannel resonator." Applied physics letters 91.12 (2007): 123121.

Goh, Celeste, Sowmya Narayanan, and Young S. Hahn. "Myeloid-derived suppressor cells: the dark knight or the joker in viral infections?." *Immunological reviews* 255.1 (2013): 210-221.

(56) References Cited

OTHER PUBLICATIONS

Golab K, Leveson-Gower D, Wang XJ, Grzanka J, Marek-Trzonkowska N, Krzystyniak A, Millis JM, Trzonkowski P, Witkowski P. Challenges in cryopreservation of regulatory T cells (Tregs) for clinical therapeutic applications. Int Immunopharmacol. 2013;16(3):371-5.

Goldring CE, Duffy PA, Benvenisty N, Andrews PW, Ben-David U, Eakins R, French N, Hanley NA, Kelly L, Kitteringham NR, Kurth J, Ladenheim D, Laverty H, McBlane J, Narayanan G, Patel S, Reinhardt J, Rossi A, Sharpe M, Park BK. Assessing the safety of stem cell therapeutics. Cell stem cell. 2011;8:618-628.

Griesche, Nadine, et al. "A simple modification of the separation method reduces heterogeneity of adipose-derived stem cells." cells tissues organs 192.2 (2010): 106-115.

Gutcher I, Donkor MK, Ma Q, Rudensky AY, Flavell RA, Li MO. Autocrine transforming growth factor-beta1 promotes in vivo Th17 cell differentiation. Immunity. 2011;34(3):396-408.

Haack-Sorensen M, Follin B, Juhl M, et al. (2016) Culture expansion of adipose derived stromal cells. A closed automated Quantum Cell Expansion System compared with manual flask-based culture. J Transl Med 14(1): 319.

Hall ED, Sullivan PG, Gibson TR, Pavel KM, Thompson BM, Scheff SW. Spatial and temporal characteristics of neurodegeneration after controlled cortical impact in mice: More than a focal brain injury. Journal of neurotrauma. 2005;22:252-265.

Hami et al., "GMP Production and Testing of Xcellerated T Cells for the Treatment of Patients with CLL," Cytotherapy, pp. 554-562, 2004.

Hamm RJ, Dixon CE, Gbadebo DM, Singha AK, Jenkins LW, Lyeth BG, Hayes RL. Cognitive deficits following traumatic brain injury produced by controlled cortical impact. Journal of neurotrauma. 1992;9:11-20.

Hanley PJ, Mei Z, Durett AG, et al. (2014) Efficient manufacturing of therapeutic mesenchymal stromal cells with the use of the Quantum Cell Expansion System. Cytotherapy 16(8): 1048-1058.

He N, Fan W, Henriquez B, Yu RT, Atkins AR, Liddle C, Zheng Y, Downes M, Evans RM. Metabolic control of regulatory T cell (Treg) survival and function by Lkb1. Proc Natl Acad Sci U S A. 2017;114(47):12542-12547.

He X, Landman S, Bauland SC, van den Dolder J, Koenen HJ, Joosten I. A TNFR2-Agonist Facilitates High Purity Expansion of Human Low Purity Treg Cells. PLoS One. 2016;11(5):e0156311.

Heskins, Michael, and James E. Guillet. "Solution properties of poly (N-isopropylacrylamide)." Journal of Macromolecular Science—Chemistry 2.8 (1968): 1441-1455.

Hill JA, Feuerer M, Tash K, Haxhinasto S, Perez J, Melamed R, Mathis D, Benoist C. Foxp3 transcription-factor-dependent and -independent regulation of the regulatory T cell transcriptional signature. Immunity. 2007;27(5):786-800.

Hollyman et al., "Manufacturing Validation of Biologicall Functional T Cells Targeted to CD19 Antigen for Autologous Adoptive Cell Therapy," J Immunother, vol. 32, No. 2, pp. 169-180, Feb.-Mar. 2009.

Horwitz, Mitchell E., et al. "Phase I/II study of stem-cell transplantation using a single cord blood unit expanded ex vivo with nicotinamide." *Journal of Clinical Oncology* 37.5 (2019): 367-373. http://www.ucdenver.edu/academics/colleges/medicalschool/centers/cancercenter/Research/sharedresources/AnimalImaging/smallanimalimaging/Pages/MRI.aspx.

ISCT Webinar "Volume Reduction technology for Large Scale Harvest or Post-thaw Manipulation of Cellular Therapeutics".

Iwashima, Shigejiro, et al. "Novel culture system of mesenchymal stromal cells from human subcutaneous adipose tissue." Stem cells and development 18.4 (2009): 533-544.

Jarocha D, Stangel-Wojcikiewicz K, Basta A, Majka M (2014) Efficient myoblast expansion for regenerative medicine use. Int J Mol Med 34(1): 83-91.

Jin, H., and J. Bae. "Neuropeptide Y regulates the hematopoietic stem cell microenvironment and prevents nerve injury in the bone marrow." *22nd Annual ISCT Meeting* (2016): S29.

Jo CH, Lee YG, Shin WH, et al. (2014) Intra-articular injection of mesenchymal stem cells for the treatment of osteoarthritis of the knee: a proof-of-concept clinical trial. Stem Cells 32(5): 1254-1266.

John Nicolette, et al (Abbott Laboratories). In Vitro Micronucleus Screening of Pharmaceutical Candidates by Flow Cyto9metry in Chinese Hamster V79 Cells, Environmental and Molecular Mutagenesis 00:000-000, 2010.

Johnson, Patrick A., et al. "Interplay of anionic charge, poly (ethylene glycol), and iodinated tyrosine incorporation within tyrosine? derived polycarbonates: Effects on vascular smooth muscle cell adhesion, proliferation, and motility." Journal of Biomedical Materials Research Part A: An Official Journal of The Society for Biomaterials, The Japanese Society for Biomaterials, and The Australian Society for Biomaterials and the Korean Society for Biomaterials 93.2 (2010): 505-514.

Johnston LC, Su X, Maguire-Zeiss K, Horovitz K, Ankoudinova I, Guschin D, Hadaczek P, Federoff HJ, Bankiewicz K, Forsayeth J. Human interleukin-10 gene transfer is protective in a rat model of Parkinson's disease. Mol Ther. 2008;16(8):1392-9.

Jones2016ISCT 2016 Poster 69.

Joy, Abraham, et al. "Control of surface chemistry, substrate stiffness, and cell function in a novel terpolymer methacrylate library." Langmuir 27.5 (2011): 1891-1899.

Kalamasz et al., "Optimization of Human T-Cell Expansion Ex Vivo Using Magnetic Beads Conjugated with Anti-CD3 and Anti-CD28 Antibodies," J Immunother, vol. 27, No. 5, pp. 405-418, Sep.-Oct. 2004.

Kim, Do-Hyung, et al. "mTOR interacts with raptor to form a nutrient-sensitive complex that signals to the cell growth machinery." *Cell* 110.2 (2002): 163-175.

Kishore M, Cheung KCP, Fu H, Bonacina F, Wang G, Coe D, Ward EJ, Colamatteo A, Jangani M, Baragetti A, Matarese G, Smith DM, Haas R, Mauro C, Wraith DC, Okkenhaug K, Catapano AL, De Rosa V, Norata GD, Marelli-Berg FM. Regulatory T Cell Migration Is Dependent on Glucokinase-Mediated Glycolysis. Immunity. 2017;47(5):875-889 e10.

Klapper et al., "Single-Pass, Closed-System Rapid Expansion of Lymphocyte Cultures for Adoptive Cell Therapy," Journal of Immunological Methods, 345, pp. 90-99, Apr. 21, 2009.

Klysz D, Tai X, Robert PA, Craveiro M, Cretenet G, Oburoglu L, Mongellaz C, Floess S, Fritz V, Matias MI, Yong C, Surh N, Marie JC, Huehn J, Zimmermann V, Kinet S, Dardalhon V, Taylor N. Glutamine-dependent alpha-ketoglutarate production regulates the balance between T helper 1 cell and regulatory T cell generation. Sci Signal. 2015;8(396):ra97.

Korpanty et al., "Tageting Vascular Enothelium with Avidin Microbubbles," Ultrasound in Medicine and Biology, vol. 31, No. 9, pp. 1279-1283, May 24, 2005.

Krauss et al., "Signaling Takes a Breath—New Quantitative Perspectives on Bioenergetics and Signal Transduction," Immunity, vol. 15, pp. 497-502, Oct. 2001.

Kulikov, A. V., et al. "Application of multipotent mesenchymal stromal cells from human adipose tissue for compensation of neurological deficiency induced by 3-nitropropionic acid in rats." Bulletin of experimental biology and medicine 145.4 (2008): 514-519.

Kumar P, Marinelarena A, Raghunathan D, Ragothaman VK, Saini S, Bhattacharya P, Fan J, Epstein AL, Maker AV, Prabhakar BS. Critical role of OX40 signaling in the TCR-independent phase of human and murine thymic Treg generation. Cell Mol Immunol. 2019;16(2):138-153.

Kwan, J. and Borden, M., "Lipid Monolayer Collapse and Microbubble Stability," Advances in Colloid and Interface Science, vols. 183-184, pp. 82-99, Aug. 21, 2012.

Lampugnani MG, Caveda L, Breviario F, Del Maschio A, Dejana E. Endothelial cell-to-cell junctions. Structural characteristics and functional role in the regulation of vascular permeability and leukocyte extravasation. Bailliere's clinical haematology. 1993;6:539-558.

Lee et al., "Continued Antigen Stimulation Is Not Required During CD4+ T Cell Clonal Expansion," The Journal of Immunology, 168, pp. 1682-1689, 2002.

Lee III, Daniel W., et al. "Long-term outcomes following CD19 CAR T cell therapy for B-ALL are superior in patients receiving a

(56) References Cited

OTHER PUBLICATIONS fludarabine/cyclophosphamide preparative regimen and post-CAR hematopoietic stem cell transplantation." Blood 128.22 (2016): 218.
Lee, Jae W., et al. "Allogeneic human mesenchymal stem cells for treatment of E. coli endotoxin-induced acute lung injury in the ex vivo perfused human lung." Proceedings of the national academy of Sciences 106.38 (2009): 16357-16362.
Levine, B., "T Lymphocyte Engineering ex vivo for Cancer and Infectious Disease," Expert Opinion on Biological Therapy, vol. 4, No. 4, pp. 475-489, 2008.
Lindstein, Tullia, et al. "Regulation of lymphokine messenger RNA stability by a surface-mediated T cell activation pathway." Science 244.4902 (1989): 339-343.
Liotta, Francesco, et al. "Frequency of regulatory T cells in peripheral blood and in tumour-infiltrating lymphocytes correlates with poor prognosis in renal cell carcinoma." BJU international 107.9 (2011): 1500-1506.
Liu W, Putnam AL, Xu-Yu Z, Szot GL, Lee MR, Zhu S, Gottlieb PA, Kapranov P, Gingeras TR, Fazekas de St Groth B, Clayberger C, Soper DM, Ziegler SF, Bluestone JA. CD127 expression inversely correlates with FoxP3 and suppressive function of human CD4+ T reg cells. J Exp Med. 2006;203(7):1701-1711.
Lum et al., "Ultrasound Radiation Force Enables Targeted Deposition of Model Drug Carriers Loaded on Microbubbles," Journal of Controlled Release, 111, pp. 128-134, 2006.
Malone et al., "Characterization of Human Tumor-Infiltrating Lymphocytes Expanded in Hollow-Fiber Bioreactors for Immunotherapy of Cancer," Cancer Biotherapy & Radiopharmaceuticals, vol. 16, No. 5, pp. 381-390, 2001.
Mao AS, Mooney DJ (2015) Regenerative medicine: current therapies and future directions. Proc Natl Acad Sci USA 112(47): 14452-14459.
Maria Streltsova, Dean Lee (Nationwide Children's Hospital, OSU, Columbus, OH) et al (Int'l Journal of Molecular Sciences, 2019).
Markgraf CG, Clifton GL, Aguirre M, Chaney SF, Knox-Du Bois C, Kennon K, Verma N. Injury severity and sensitivity to treatment after controlled cortical impact in rats. Journal of neurotrauma. 2001;18:175-186.
Mathew et al. A Phase I Clinical Trials I with Ex Vivo Expanded Recipient Regulatory T cells in Living Donor Kidney Transplants. Nature, Scientific Reports 8:7428 (1-12), 2018.
Mathew, James M., et al. "A phase I clinical trial with ex vivo expanded recipient regulatory T cells in living donor kidney transplants." Scientific reports 8.1 (2018): 1-12.
Matthay, Michael A., et al. "Therapeutic potential of mesenchymal stem cells for severe acute lung injury." Chest 138.4 (2010): 965-972.
Maynard CL, Harrington LE, Janowski KM, Oliver JR, Zindl CL, Rudensky AY, Weaver CT. Regulatory T cells expressing interleukin 10 develop from Foxp3+ and Foxp3− precursor cells in the absence of interleukin 10. Nat Immunol. 2007;8(9):931-41.
McKenna DH, Jr., Sumstad D, Kadidlo DM, et al. Optimization of cGMP purification and expansion of umbilical cord blood-derived T-regulatory cells in support of first-in-human clinical trials. Cytotherapy 2017;19:250-62.
McLimans W, Kinetics of Gas Diffusion in Mammalian Cell Culture Systems. Biotechnology and Bioengineering 1968; 10:725-740.
McMurtrey, Richard J. "Analytic models of oxygen and nutrient diffusion, metabolism dynamics, and architecture optimization in three-dimensional tissue constructs with applications and insights in cerebral organoids." Tissue Engineering Part C: Methods 22.3 (2016): 221-249.
Menge, Tyler, et al. "Mesenchymal stem cells regulate blood-brain barrier integrity through TIMP3 release after traumatic brain injury." Science translational medicine 4.161 (2012): 161ra150-161ra150.
Miska J, Lee-Chang C, Rashidi A, Muroski ME, Chang AL, Lopez-Rosas A, Zhang P, Panek WK, Cordero A, Han Y, Ahmed AU, Chandel NS, Lesniak MS. HIF-1alpha Is a Metabolic Switch between Glycolytic-Driven Migration and Oxidative Phosphorylation-Driven Immunosuppression of Tregs in Glioblastoma. Cell Rep. 2019;27(1):226-237 e4.
Miyara M, Yoshioka Y, Kitoh A, Shima T, Wing K, Niwa A, Parizot C, Taflin C, Heike T, Valeyre D, Mathian A, Nakahata T, Yamaguchi T, Nomura T, Ono M, Amoura Z, Gorochov G, Sakaguchi S. Functional delineation and differentiation dynamics of human CD4+ T cells expressing the FoxP3 transcription factor. Immunity. 2009;30(6):899-911.
Nankervis B, Jones M, Vang B et al. (2018) Optimizing T Cell Expansion in a Hollow-Fiber Bioreactor. Curr Stem Cell Rep. Advanced online publication. https://doi.org/10.1007/s40778-018-0116-x.
Nankervis, Brian, et al. "Optimizing T cell expansion in a hollow-fiber bioreactor." Current Stem Cell Reports 4.1 (2018): 46-51.
Nedoszytko B, Lange M, Sokolowska-Wojdylo M, Renke J, Trzonkowski P, Sobjanek M, Szczerkowska-Dobosz A, Niedoszytko M, Gorska A, Romantowski J, Czarny J, Skokowski J, Kalinowski L, Nowicki R. The role of regulatory T cells and genes involved in their differentiation in pathogenesis of selected inflammatory and neoplastic skin diseases. Part II: The Treg role in skin diseases pathogenesis. Postepy Dermatol Alergol. 2017;34(5):405-417.
Nehlin JO, Just M, Rustan AC (2011) Human myotubes from myoblast cultures undergoing senescence exhibit defects in glucose and lipid metabolism. Biogerontology 12: 349-365.
New victories for adult Stem Cell Research New York Feb. 6, 2007.
Newton R, Priyadharshini B, Turka LA. Immunometabolism of regulatory T cells. Nat Immunol. 2016;17(6):618-25.
Ng TH, Britton GJ, Hill EV, Verhagen J, Burton BR, Wraith DC. Regulation of adaptive immunity; the role of interleukin-10. Front Immunol. 2013;4:129.
Nikolaychik, V. V., M. M. Samet, and P. I. Lelkes. "A New, Cryoprecipitate Based Coating For Improved Endothelial Cell Attachment And Growth On Medical Grade Artificial Surfaces." ASAIO Journal (American Society for Artificial Internal Organs: 1992) 40.3 (1994): M846-52.
Nish SA, Schenten D, Wunderlich FT, Pope SD, Gao Y, Hoshi N, Yu S, Yan X, Lee HK, Pasman L, Brodsky I, Yordy B, Zhao H, Bruning J, Medzhitov R. T cell-intrinsic role of IL-6 signaling in primary and memory responses. Elife. 2014;3:e01949.
Niwayama, Jun, et al. "Analysis of hemodynamics during blood purification therapy using a newly developed noninvasive continuous monitoring method." Therapeutic Apheresis and Dialysis 10.4 (2006): 380-386.
Okano et al (Tokyo Women's Medical College, Japan) demonstrated the recovery of endothelial cells and hepatocytes from plasma-treated polystyrene dishes grafted with PNIAAm (Journal of Biomedical Materials Research, 1993).
Onishi Y, Fehervari Z, Yamaguchi T, Sakaguchi S. Foxp3+ natural regulatory T cells preferentially form aggregates on dendritic cells in vitro and actively inhibit their maturation. Proc Natl Acad Sci U S A. 2008;105(29):10113-8.
Onyszchuk G, LeVine SM, Brooks WM, Berman NE. Post-acute pathological changes in the thalamus and internal capsule in aged mice following controlled cortical impact injury: A magnetic resonance imaging, iron histochemical, and glial immunohistochemical study. Neuroscience letters. 2009;452:204-208.
Pacella I, Procaccini C, Focaccetti C, Miacci S, Timperi E, Faicchia D, Severa M, Rizzo F, Coccia EM, Bonacina F, Mitro N, Norata GD, Rossetti G, Ranzani V, Pagani M, Giorda E, Wei Y, Matarese G, Barnaba V, Piconese S. Fatty acid metabolism complements glycolysis in the selective regulatory T cell expansion during tumor growth. Proc Natl Acad Sci U S A. 2018;115(28):E6546-E6555.
Parhi, Purnendu, Avantika Golas, and Erwin A. Vogler. "Role Of Proteins And Water In The Initial Attachment Of Mammalian Cells To Biomedical Surfaces: A Review." Journal of Adhesion Science and Technology 24.5 (2010): 853-888.
Pati S, Gerber MH, Menge TD, Wataha KA, Zhao Y, Baumgartner JA, Zhao J, Letourneau PA, Huby MP, Baer LA, Salsbury JR, Kozar RA, Wade CE, Walker PA, Dash PK, Cox CS, Jr., Doursout MF, Holcomb JB. Bone marrow derived mesenchymal stem cells inhibit inflammation and preserve vascular endothelial integrity in the lungs after hemorrhagic shock. PloS one. 2011;6:e25171.

(56) References Cited

OTHER PUBLICATIONS

Pati S, Khakoo AY, Zhao J, Jimenez F, Gerber MH, Harting M, Redell JB, Grill R, Matsuo Y, Guha S, Cox CS, Reitz MS, Holcomb JB, Dash PK. Human mesenchymal stem cells inhibit vascular permeability by modulating vascular endothelial cadherin/beta-catenin signaling. Stem cells and development. 2011;20:89-101.
Pati, Shibani, and Todd E. Rasmussen. "Cellular therapies in trauma and critical care medicine: Looking towards the future." PLoS Medicine 14.7 (2017): e1002343.
Pati, Shibani, et al. "Lyophilized plasma attenuates vascular permeability, inflammation and lung injury in hemorrhagic shock." PloS one 13.2 (2018): e0192363.
Peters JH, Preijers FW, Woestenenk R, Hilbrands LB, Koenen HJ, Joosten I. Clinical grade Treg: GMP isolation, improvement of purity by CD127 Depletion, Treg expansion, and Treg cryopreservation. PLoS One. 2008;3(9):e3161.
Peters, R.; Jones, M.; Brecheisen, M.; Startz, T.; Vang, B.; Nankervis, B.; Frank, N.; Nguyen, K. (2012) TerumoBCT. https://www.terumobct.com/location/north-america/products-and-services/Pages/Quantum-Materials.aspx.
Porter CM, Horvath-Arcidiacono JA, Singh AK, Horvath KA, Bloom ET, Mohiuddin MM. Characterization and expansion of baboon CD4+CD25+ Treg cells for potential use in a non-human primate xenotransplantation model. Xenotransplantation. 2007;14(4):298-308.
Povsic TJ, O'Connor CM, Henry T, et al. (2011) A double-blind, randomized, controlled, multicenter study to assess the safety and cardiovascular effects of skeletal myoblast implantation by catheter delivery in patients with chronic heart failure after myocardial infarction. Am Heart J 162(4): 654-662.
Prockop, Darwin J., Carl A. Gregory, and Jeffery L. Spees. "One strategy for cell and gene therapy: harnessing the power of adult stem cells to repair tissues." Proceedings of the National Academy of Sciences 100.suppl_1 (2003): 11917-11923.
Q. L. Hao, et al. A functional comparison of CD34+ CD38= cells in cord blood and bone marrow. Blood 86:3745-3753, 1995.
Rahmahwati, Nurlaela, Deana Wahyuningrum, and Anita Alni. "The Synthesis Of Polyethersulfone (PES) Derivatives For The Immobilization Of Lipase Enzyme." Key Engineering Materials. vol. 811. Trans Tech Publications Ltd, 2019.
Rey-Jurado, Emma, et al. "Assessing the importance of domestic vaccine manufacturing centers: an overview of immunization programs, vaccine manufacture, and distribution." Frontiers in immunology 9 (2018): 26.
Roballo KC, Dhungana S, Z. J, Oakey J, Bushman J. Localized delivery of immunosuppressive regulatory T cells to peripheral nerve allografts promotes regeneration of branched segmental defects. Biomaterials. 2019;209:1-9.
Ronco C1, Levin N, Brendolan A, Nalesso F, Cruz D, Ocampo C, Kuang D, Bonello M, De Cal M, Corradi V, Ricci Z. Flow distribution analysis by helical scanning in polysulfone hemodialyzers: effects of fiber structure and design on flow patterns and solute clearances. Hemodial Int. Oct. 2006; 10(4):380-8.
Rosenblum MD, Way SS, Abbas AK. Regulatory T cell memory. Nat Rev Immunol. 2016;16(2):90-101.
Rubtsov YP, Rasmussen JP, Chi EY, Fontenot J, Castelli L, Ye X, Treuting P, Siewe L, Roers A, Henderson WR, Jr., Muller W, Rudensky AY. Regulatory T cell-derived interleukin-10 limits inflammation at environmental interfaces. Immunity. 2008;28(4):546-58.
Rudensky, Alexander Y. "Regulatory T cells and Foxp3." Immunological reviews 241.1 (2011): 260-268.
S. Koestenbauer, et al. Protocols for Hematopoietic Stem Cell Expansion from Umbilical Cord Blood. Cell Transplantation 18: 1059-1068, 2009.
S. L. Smith, et al. Expansion of neutrophil precursors and progenitors in suspension cultures of CD34+ cells enriched from human bone marrow. Experimental Hematology 21:870-877, 1993.
Safinia N, Grageda N, Scotta C, Thirkell S, Fry LJ, Vaikunthanathan T, Lechler RI, Lombardi G. Cell Therapy in Organ Transplantation: Our Experience on the Clinical Translation of Regulatory T Cells. Front Immunol. 2018;9:354.
Sahay A, Scobie KN, Hill AS, O'Carroll CM, Kheirbek MA, Burghardt NS, Fenton AA, Dranovsky A, Hen R. Increasing adult hippocampal neurogenesis is sufficient to improve pattern separation. Nature. 2011;472:466-470.
Sakaguchi S, Sakaguchi N, Asano M, Itoh M, Toda M. Immunologic self-tolerance maintained by activated T cells expressing IL-2 receptor alpha-chains (CD25). Breakdown of a single mechanism of self-tolerance causes various autoimmune diseases. J Immunol. 1995;155(3):1151-64.
Sakaguchi S, Sakaguchi N, Shimizu J, Yamazaki S, Sakihama T, Itoh M, Kuniyasu Y, Nomura T, Toda M, Takahashi T. Immunologic tolerance maintained by CD25+ CD4+ regulatory T cells: their common role in controlling autoimmunity, tumor immunity, and transplantation tolerance. Immunol Rev. 2001;182:18-32.
Schild, Howard G. "Poly (N-isopropylacrylamide): experiment, theory and application." Progress in polymer science 17.2 (1992): 163-249.
Schmitz R, Alessio A, Kina P. The Physics of PET/CT scanners. Imaging Research Laboratory, Department of Radiology, University of Washington http://depts.washington.edu/imreslab/education/Physics%20of%20PET.pdf.
Schwartz RH. T cell anergy. Annu Rev Immunol. 2003;21:305-34.
Shevkoplyas et al., "The Force Acting on a Superparamagnetic Bead due to an Applied Magnetic Field," Lab on a Chip , 7, pp. 1294-1302, 2007.
Shimazu Y, Shimazu Y, Hishizawa M, Hamaguchi M, Nagai Y, Sugino N, Fujii S, Kawahara M, Kadowaki N, Nishikawa H, Sakaguchi S, Takaori-Kondo A. Hypomethylation of the Treg-Specific Demethylated Region in FOXP3 Is a Hallmark of the Regulatory T-cell Subtype in Adult T-cell Leukemia. Cancer Immunol Res. 2016;4(2):136-45.
Sigma-Aldrich Cheimcals Mitomycin C (M4287) MSDS, v4.4, Jul. 7, 2011.
Sirsi, S. and Borden, M., "Microbubble Composition, Properties, and Biomedical Applications," Bubble Science, Engineering & Technolology, vol. 1, No. 1-2, pp. 3-17, 2009.
Smith C, Okern G, Rehan S, et al. Ex vivo expansion of human T cells for adoptive immunotherapy using the novel Xeno-free CTS Immune Cell Serum Replacement. Clinical & Translational Immunology 2015;4:e31.
Somerville et al., "Clinical Scale Rapid Expansion of Lymphocytes for Adoptive Cell Transfer Therapy in the WAVE® Bioreactor," Journal of Translational Medicine, vol. 10, No. 69, pp. 1-11, 2012.
Somerville, R. and Dudley, M., "Bioreactors Get Personal," Oncolmmunology, vol. 1, No. 8, pp. 1435-1437, Nov. 2012.
Spectrum Labs KrosFlo Research Ili TFF System, undated, Spectrum Laboratories, Inc., 4 pages.
Stafano Tiziani, et al. Metabolomic Profiling of Drug Response in Acute Myeloid Leukaemia Cell lines. PLOSone 4(1): e4251 (Jan. 22, 2009).
StAR_Abstract, undated, author unknown, 1 page.
Startz et al.May 2016 TBCT T-cell White Paper.
Startz, T., et al. "Maturation of dendritic cells from CD14+ monocytes in an automated functionally closed hollow fiber bioreactor system." Cytotherapy 16.4 (2014): S29.
Steven M. Bryce, et al (Litron Laboratories). In vitro micronucleus assay scored by flow cytometry provides a comprehensive evaluation of cytogenetic damage and cytotoxicity. Mutation Research 630(1-2): 78-91, 2007.
Steven M. Bryce, et al (Novartis Pharma AG, Johnson & Johnson Pharmaceutical Research, GlaxoSmithKline). Interlaboratory evaluation of a flow cytometric, high content in vitro micronucleus assay. Genetic Toxicology and Environmental Mutagenesis 650: 181-195, 2008.
Stuart, Martien A. Cohen, et al. "Emerging applications of stimuli-responsive polymer materials." Nature materials 9.2 (2010): 101-113.
Su LF, Del Alcazar D, Stelekati E, Wherry EJ, Davis MM. Antigen exposure shapes the ratio between antigen-specific Tregs and con-

(56) References Cited

OTHER PUBLICATIONS ventional T cells in human peripheral blood. Proc Natl Acad Sci U S A. 2016;113(41):E6192-E6198.
Trzonkowski et al., "Ex Vivo Expansion of CD4+ CD25+ T Regulatory Cells for Immunosuppressive Therapy," Cytometry Part A, 75A, pp. 175-188, 2009.
Trzonkowski, Piotr, et al. "First-in-man clinical results of the treatment of patients with graft versus host disease with human ex vivo expanded CD4+ CD25+ CD127? T regulatory cells." Clinical immunology 133.1 (2009): 22-26.
Tsvetkov, Ts, et al. "Isolation and cryopreservation of human peripheral blood monocytes." Cryobiology 23.6 (1986): 531-536.
Underwood, P. Anne, et al. "Effects of base material, plasma proteins and FGF2 on endothelial cell adhesion and growth." Journal of Biomaterials Science, Polymer Edition 13.8 (2002): 845-862.
Van der Net JB, Bushell A, Wood KJ, Harden PN. Regulatory T cells: first steps of clinical application in solid organ transplantation. Transpl Int. 2016;29(1):3-11.
Van der Windt GJ, Pearce EL. Metabolic switching and fuel choice during T-cell differentiation and memory development. Immunol Rev. 2012;249(1):27-42.
Vera et al., "Accelerated Production of Antigen-Specific T-Cells for Pre-Clinical and Clinical Applications Using Gas-Permeable Rapid Expansion Cultureware (G-Rex)," J Immunother, vol. 33, No. 3, pp. 305-315, Apr. 2010.
Villa, Alma Y. Camacho, et al. "CD133+ CD34+ and CD133+ CD38+ blood progenitor cells as predictors of platelet engraftment in patients undergoing autologous peripheral blood stem cell transplantation." Transfusion and Apheresis Science 46.3 (2012): 239-244.
Visser EP1, Disselhorst JA, Brom M, Laverman P, Gotthardt M, Oyen WJ, Boerman OC. Spatial resolution and sensitivity of the Inveon small-animal PET scanner. J Nucl Med. Jan. 2009;50(1):139-47.
Wagner Jr, John E., et al. "Phase I/II trial of StemRegenin-1 expanded umbilical cord blood hematopoietic stem cells supports testing as a stand-alone graft." Cell stem cell 18.1 (2016): 144-155.
Walker, Peter A., et al. "Direct intrathecal implantation of mesenchymal stromal cells leads to enhanced neuroprotection via an NF?B-mediated increase in interleukin-6 production." Stem cells and development 19.6 (2010): 867-876.
Wang R, Dillon CP, Shi LZ, Milasta S, Carter R, Finkelstein D, McCormick LL, Fitzgerald P, Chi H, Munger J, Green DR. The transcription factor Myc controls metabolic reprogramming upon T lymphocyte activation. Immunity. 2011;35(6):871-82.
Wang, Jiamian, John A. Jansen, and Fang Yang. "Electrospraying: possibilities and challenges of engineering carriers for biomedical applications—a mini review." Frontiers in Chemistry 7 (2019): 258.
Ward H, Vigues S, Poole S, Bristow AF. The rat interleukin 10 receptor: cloning and sequencing of cDNA coding for the alpha-chain protein sequence, and demonstration by western blotting of expression in the rat brain. Cytokine. 2001;15(5):237-40.
Wawman, Rebecca Ellen, Helen Bartlett, and Ye Htun Oo. "Regulatory T cell metabolism in the hepatic microenvironment." Frontiers in immunology 8 (2018): 1889.
Weber et al., "White Paper on Adoptive Cell Therapy for Cancer with Tumor-Infiltrating Lymphocytes: A Report of the CTEP Subcommittee on Adoptive Cell Therapy," Clinical Cancer Research, vol. 17, No. 7, pp. 1664-1673, Apr. 1, 2011.
Weiss RA, Weiss MA, Beasley KL, Munavalli G (2007) Autologous cultured fibroblast injection for facial contour deformities: a prospective, placebo-controlled, Phase III clinical trial. Dermatol Surg 33(3): 263-268.
Widdel, F. 2010. "Theory and measurement of bacterial growth" http://www.mpi-bremen.de/Binaries/Binary13037/Wachstumsversuch.pdf.
Yamada, Noriko, et al. "Thermo?responsive polymeric surfaces; control of attachment and detachment of cultured cells." Die Makromolekulare Chemie, Rapid Communications 11.11 (1990): 571-576.
Yoshinari, Masao, et al. "Effect of cold plasma-surface modification on surface wettability and initial cell attachment." International Journal of Biomedical and Biological Engineering 3.10 (2009): 507-511.
Zappasodi et al., "The Effect Of Artificial Antigen-Presenting Cells with Preclustered Anit-CD28/-CD3/LFA-1 Monoclonal Antibodies on the Induction of ex vivo Expansion of Functional Human Antitumor T Cells," Haematologica, vol. 93, No. 10, pp. 1523-1534, 2008.
Zemmour D, Zilionis R, Kiner E, Klein AM, Mathis D, Benoist C. Publisher Correction: Single-cell gene expression reveals a landscape of regulatory T cell phenotypes shaped by the TCR. Nat Immunol. 2018;19(6):645.
Zeng B, Kwak-Kim J, Liu Y, Liao AH. Treg cells are negatively correlated with increased memory B cells in pre-eclampsia while maintaining suppressive function on autologous B-cell proliferation. Am J Reprod Immunol. 2013;70(6):454-63.
Examination Report for related European Patent Application No. 17803614.1; dated Mar. 10, 2023; 5 pages.
Doran, M., Cell Transplantation, Cognizant Comm. Corp., vol. 21 (6), pp. 1235-1244, Jun. 2012.
Chinese Office Action for related Chinese Application No. 201780040488.2; dated May 12, 2023; 8 pages.
Pankaj Godara et al., Design of Bioreactors for Mesenchymal Stem Cell Tissue Engineering, Journal of Chemical Technology and Biotechnology, vol. 83, pp. 408-420, Feb. 2008.

\* cited by examiner

CELL EXPANSION

BACKGROUND

Cell Expansion Systems (CES's) may be used to expand and differentiate a variety of cell types that may be used for both research and therapeutic purposes. As one example, CD34+ progenitor cells hematological progenitor stem cells (HSC's) have been identified as possible treatments in diseases such as cancers (e.g., lymphoma, leukemia, myeloma, etc.). HSC's may be collected from bone marrow, cord blood, and or peripheral blood. It has been suggested that a minimum number of HSC's should be given as an effective dose. Accordingly, the HSC's may be grown from an initial amount to at least an amount that may be considered an effective dose.

Embodiments have been made in light of these and other considerations. However, the relatively specific problems discussed above do not limit the applicability of the embodiments of the present disclosure.

SUMMARY

The summary is provided to introduce aspects of some embodiments in a simplified form, and is not intended to identify key or essential elements, nor is it intended to limit the scope of the claims.

Embodiments relate to cell expansion systems (CES's) and methods of growing cells in a bioreactor of a cell expansion system. Embodiments provide methods for expanding cells in a bioreactor, such as a hollow fiber bioreactor. Embodiments may provide for introducing cells, e.g., hematopoietic stem cells (HSC's) (for example, CD34+ cells) into a hollow fiber bioreactor, wherein the hollow fiber bioreactor includes a plurality of hollow fibers. Embodiments may provide for exposing the first plurality of cells to growth conditions. The growth conditions may include exposing the first plurality of cells to a combination of growth factors in the hollow fiber bioreactor. In embodiments, the growth conditions may include, but are not limited to, co-cultured cells and a combination of growth factors. After exposing the cells to the growth conditions, the cells may be expanded to generate a second plurality of expanded cells. The second plurality of expanded cells may then be removed from the bioreactor.

BRIEF DESCRIPTION OF THE DRAWINGS

Non-limiting and non-exhaustive embodiments are described with reference to the following figures.

DETAILED DESCRIPTION

Figure 1:
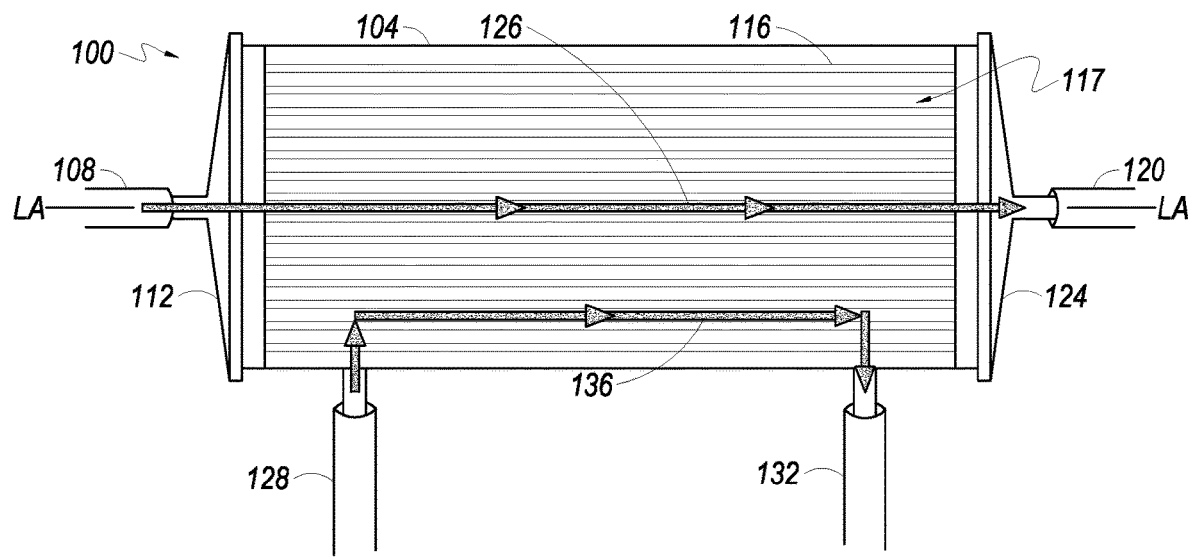
FIG. 1 depicts a perspective view of a hollow fiber bioreactor, in accordance with embodiments.

The principles of the present disclosure may be further understood by reference to the following detailed description and the embodiments depicted in the accompanying drawings. It should be understood that although specific features are shown and described below with respect to detailed embodiments, the present disclosure is not limited to the embodiments described below.

Reference will now be made in detail to the embodiments illustrated in the accompanying drawings and described below. Wherever possible, the same reference numerals are used in the drawings and the description to refer to the same or like parts.

Referring to FIG. 1, an example of a hollow fiber bioreactor 100, which may be used with the present disclosure is shown in front side elevation view. Hollow fiber bioreactor 100 has a longitudinal axis LA-LA and includes chamber housing 104. In at least one embodiment, chamber housing 104 includes four openings or ports: intracapillary (IC) inlet port 108, IC outlet port 120, extracapillary (EC) inlet port 128, and EC outlet port 132.

According to embodiments of the present disclosure, fluid in a first circulation path enters hollow fiber bioreactor 100 through IC inlet port 108 at a first longitudinal end 112 of the hollow fiber bioreactor 100, passes into and through the intracapillary side (referred to in various embodiments as the intracapillary ("IC") side or "IC space" of a hollow fiber membrane) of a plurality of hollow fibers 116, and out of hollow fiber bioreactor 100 through IC outlet port 120 located at a second longitudinal end 124 of the hollow fiber bioreactor 100. The fluid path between the IC inlet port 108 and the IC outlet port 120 defines the IC portion 126 of the hollow fiber bioreactor 100. Fluid in a second circulation path flows in the hollow fiber bioreactor 100 through EC inlet port 128, comes in contact with the extracapillary side or outside (referred to as the "EC side" or "EC space" of the membrane) of the hollow fibers 116, and exits hollow fiber bioreactor 100 via EC outlet port 132. The fluid path between the EC inlet port 128 and the EC outlet port 132 comprises the EC portion 136 of the hollow fiber bioreactor 100. Fluid entering hollow fiber bioreactor 100 via the EC inlet port 128 may be in contact with the outside of the hollow fibers 116. Small molecules (e.g., ions, water, oxygen, lactate, etc.) may diffuse through the hollow fibers 116 from the interior or IC space of the hollow fiber to the exterior or EC space, or from the EC space to the IC space. Large molecular weight molecules, such as growth factors, may be too large to pass through the hollow fiber membrane, and remain in the IC space of the hollow fibers 116. The media may be replaced as needed, in embodiments. Media may also be circulated through an oxygenator or gas transfer module to exchange gasses as needed (see e.g., cell expansion systems 500 (FIG. 5) and 600 (FIG. 6)). Cells may be contained within a first circulation path and/or a second circulation path, as described below, and may be on either the IC side and/or EC side of the membrane, according to embodiments.

The material used to make the hollow fiber membrane may be any biocompatible polymeric material which is capable of being made into hollow fibers. One material which may be used is a synthetic polysulfone-based material, according to an embodiment of the present disclosure. In order for the cells to adhere to the surface of the hollow fibers, the surface may be modified in some way, either by coating at least the cell growth surface with a protein, e.g., a glycoprotein such as fibronectin or collagen, or by exposing the surface to radiation. Gamma treating the membrane surface may allow for attachment of adherent cells without additionally coating the membrane with fibronectin or the like. Bioreactors made of gamma treated membranes may be reused. Other coatings and/or treatments for cell attachment may be used in accordance with embodiments of the present disclosure.

Figure 2:
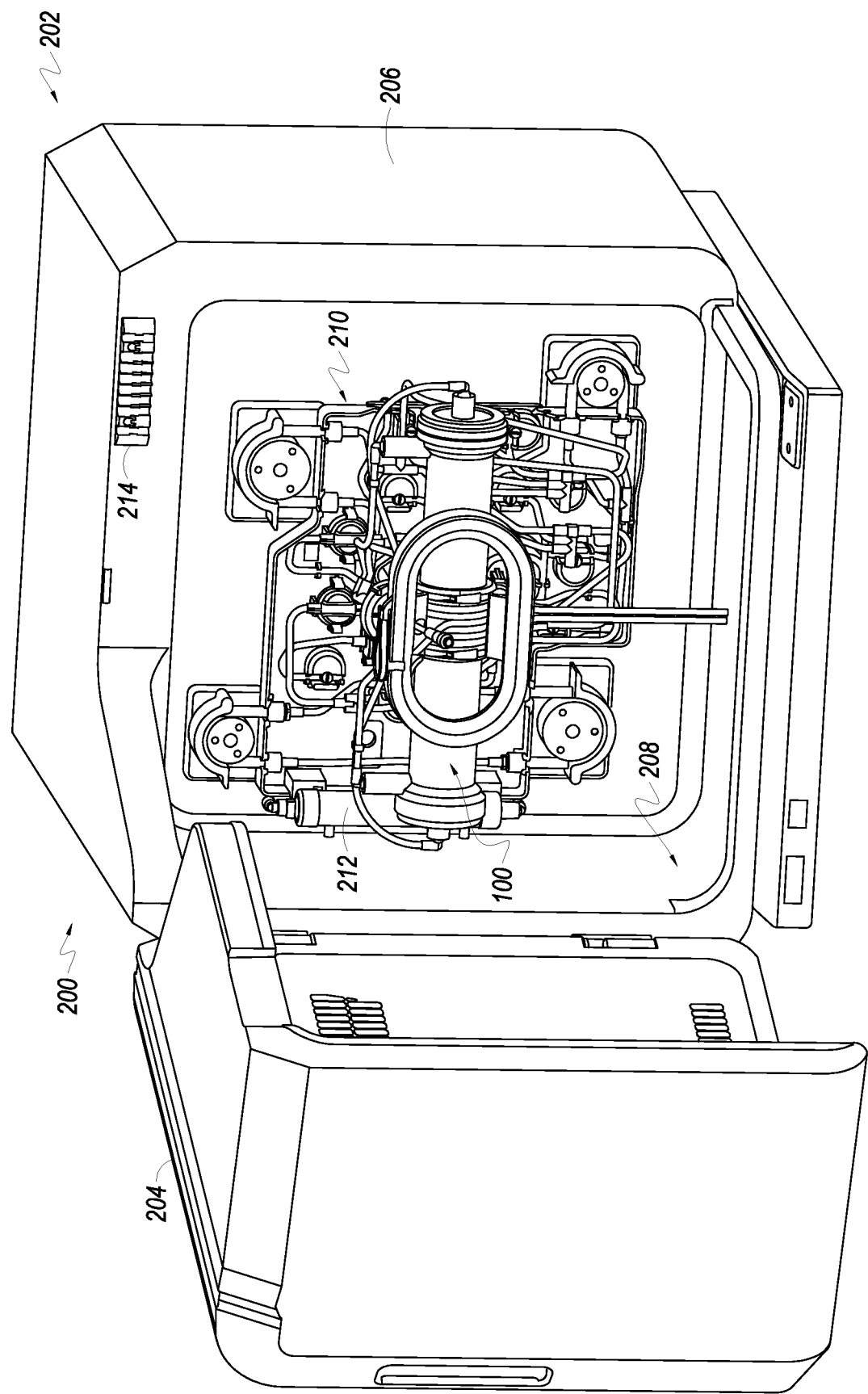
FIG. 2 illustrates a perspective view of a cell expansion system with a premounted fluid conveyance device, in accordance with embodiments.

Turning to FIG. 2, an embodiment of a cell expansion system 200 with a premounted fluid conveyance assembly is shown in accordance with embodiments of the present disclosure. The CES 200 includes a cell expansion machine 202 that comprises a hatch or closable door 204 for engagement with a back portion 206 of the cell expansion machine 202. An interior space 208 within the cell expansion machine 202 includes features adapted for receiving and engaging a premounted fluid conveyance assembly 210 that includes a bioreactor 100. The premounted fluid conveyance assembly 210 may be detachably-attachable to the cell expansion machine 202 to facilitate relatively quick exchange of a new or unused premounted fluid conveyance assembly 210 at a cell expansion machine 202 for a used premounted fluid conveyance assembly 210 at the same cell expansion machine 202. A single cell expansion machine 202 may be operated to grow or expand a first set of cells using a first premounted fluid conveyance assembly 210 and, thereafter, may be used to grow or expand a second set of cells using a second premounted fluid conveyance assembly 210 without needing to be sanitized between interchanging the first premounted fluid conveyance assembly 210 for the second premounted fluid conveyance assembly 210. The premounted fluid conveyance assembly includes a bioreactor 100 and an oxygenator or gas transfer module 212. Tubing guide slots are shown as 214 for receiving various media tubing connected to premounted fluid conveyance assembly 210, according to embodiments.

Figure 3:
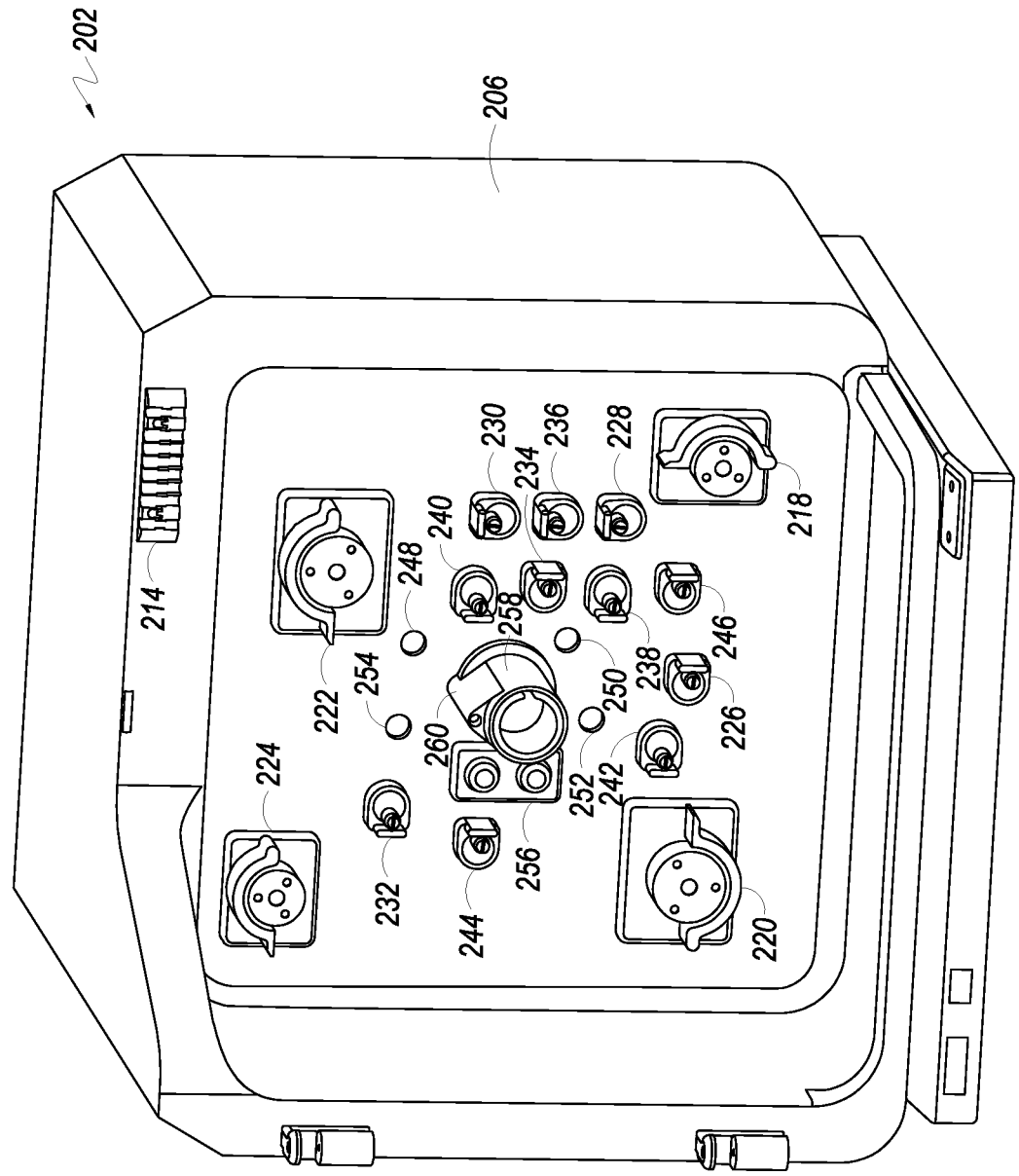
FIG. 3 depicts a perspective view of a housing of a cell expansion system, in accordance with embodiments.

Next, FIG. 3 illustrates the back portion 206 of cell expansion machine 202 prior to detachably-attaching a premounted fluid conveyance assembly 210 (FIG. 2), in accordance with embodiments of the present disclosure. The closable door 204 (shown in FIG. 2) is omitted from FIG. 3. The back portion 206 of the cell expansion machine 202 includes a number of different structures for working in combination with elements of a premounted fluid conveyance assembly 210. More particularly, the back portion 206 of the cell expansion machine 202 includes a plurality of peristaltic pumps for cooperating with pump loops on the premounted fluid conveyance assembly 210, including the IC circulation pump 218, the EC circulation pump 220, the IC inlet pump 222, and the EC inlet pump 224. In addition, the back portion 206 of the cell expansion machine 202 includes a plurality of valves, including the IC circulation valve 226, the reagent valve 228, the IC media valve 230, the air removal valve 232, the cell inlet valve 234, the wash valve 236, the distribution valve 238, the EC media valve 240, the IC waste valve 242, the EC waste valve 244, and the harvest valve 246. Several sensors are also associated with the back portion 206 of the cell expansion machine 202, including the IC outlet pressure sensor 248, the combination IC inlet pressure and temperature sensors 250, the combination EC inlet pressure and temperature sensors 252, and the EC outlet pressure sensor 254. Also shown is an optical sensor 256 for an air removal chamber.

In accordance with embodiments, a shaft or rocker control 258 for rotating the bioreactor 100 is shown in FIG. 3. Shaft fitting 260 associated with the shaft or rocker control 258 allows for proper alignment of a shaft access aperture, see e.g., 424 (FIG. 4) of a tubing-organizer, see e.g., 300 (FIG. 4) of a premounted conveyance assembly 210 or 400 with the back portion 206 of the cell expansion machine 202. Rotation of shaft or rocker control 258 imparts rotational movement to shaft fitting 260 and bioreactor 100. Thus, when an operator or user of the CES 200 attaches a new or unused premounted fluid conveyance assembly 400 (FIG. 4) to the cell expansion machine 202, the alignment is a relatively simple matter of properly orienting the shaft access aperture 424 (FIG. 4) of the premounted fluid conveyance assembly 210 or 400 with the shaft fitting 260.

Figure 4:
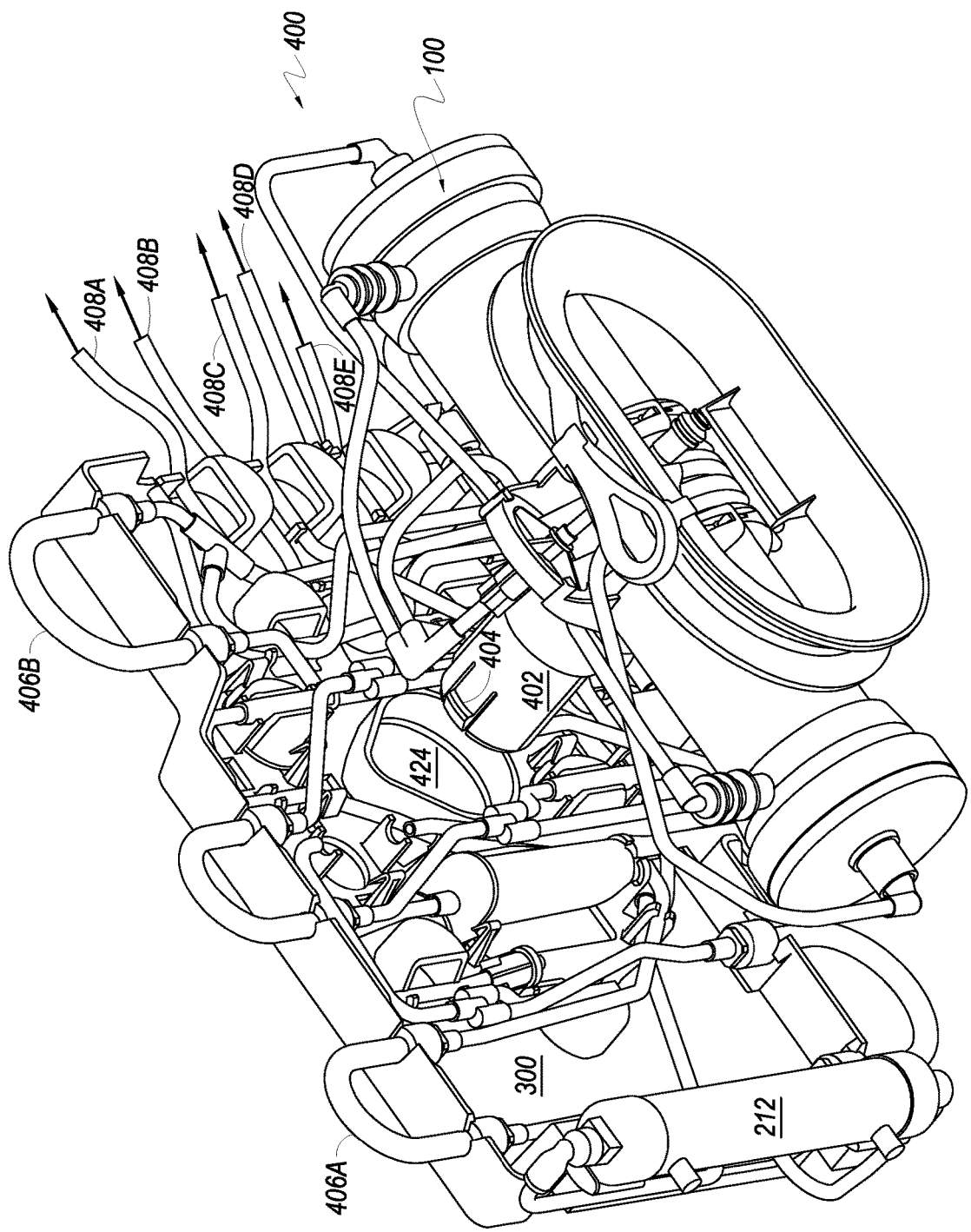
FIG. 4 illustrates a perspective view of a premounted fluid conveyance device, in accordance with embodiments.

Turning to FIG. 4, a perspective view of a detachably-attachable premounted fluid conveyance assembly 400 is shown. The premounted fluid conveyance assembly 400 may be detachably-attachable to the cell expansion machine 202 to facilitate relatively quick exchange of a new or unused premounted fluid conveyance assembly 400 at a cell expansion machine 202 for a used premounted fluid conveyance assembly 400 at the same cell expansion machine 202. As shown in FIG. 4, the bioreactor 100 may be attached to a bioreactor coupling that includes a shaft fitting 402. The shaft fitting 402 includes one or more shaft fastening mechanisms, such as a biased arm or spring member 404 for engaging a shaft, e.g., 258 (shown in FIG. 3), of the cell expansion machine 202.

In embodiments, the shaft fitting 402 and the spring member 404 connect to mechanisms of a cell expansion system that rotate the bioreactor 100. For example, in some embodiments, the cell expansion system may be part of a QUANTUM® Cell Expansion System (CES), manufactured by Terumo BCT, Inc. of Lakewood, CO, which provides for rotation of a bioreactor. Examples of cell expansion systems that provide for rotation of the bioreactor are described in at least: U.S. Pat. No. 8,399,245, issued Mar. 19, 2013, entitled "ROTATION SYSTEM FOR CELL GROWTH CHAMBER OF A CELL EXPANSION SYSTEM AND METHOD OF USE THEREFOR;" U.S. Pat. No. 8,809,043, issued Feb. 13, 2013, entitled "ROTATION SYSTEM FOR CELL GROWTH CHAMBER OF A CELL EXPANSION SYSTEM AND METHOD OF USE THEREFOR;" and U.S. Pat. No. 9,057,045, issued Jun. 16, 2015, entitled "METHOD OF LOADING AND DISTRIBUTING CELLS IN A BIOREACTOR OF A CELL EXPANSION SYSTEM;" all three of which are hereby incorporated by reference in their entirety as if set forth herein in full.

According to embodiments, the premounted fluid conveyance assembly 400 includes tubing 408A, 408B, 408C, 408D, 408E, etc., and various tubing fittings to provide the fluid paths shown in FIGS. 5 and 6, as discussed below. Pump loops 406A, 406B, and 406C are also provided for the pump(s). In embodiments, although the various media may be provided at the site where the cell expansion machine 202 is located, the premounted fluid conveyance assembly 400 may include sufficient tubing length to extend to the exterior of the cell expansion machine 202 and to enable welded connections to tubing associated with the media bags, according to embodiments.

Figure 5:
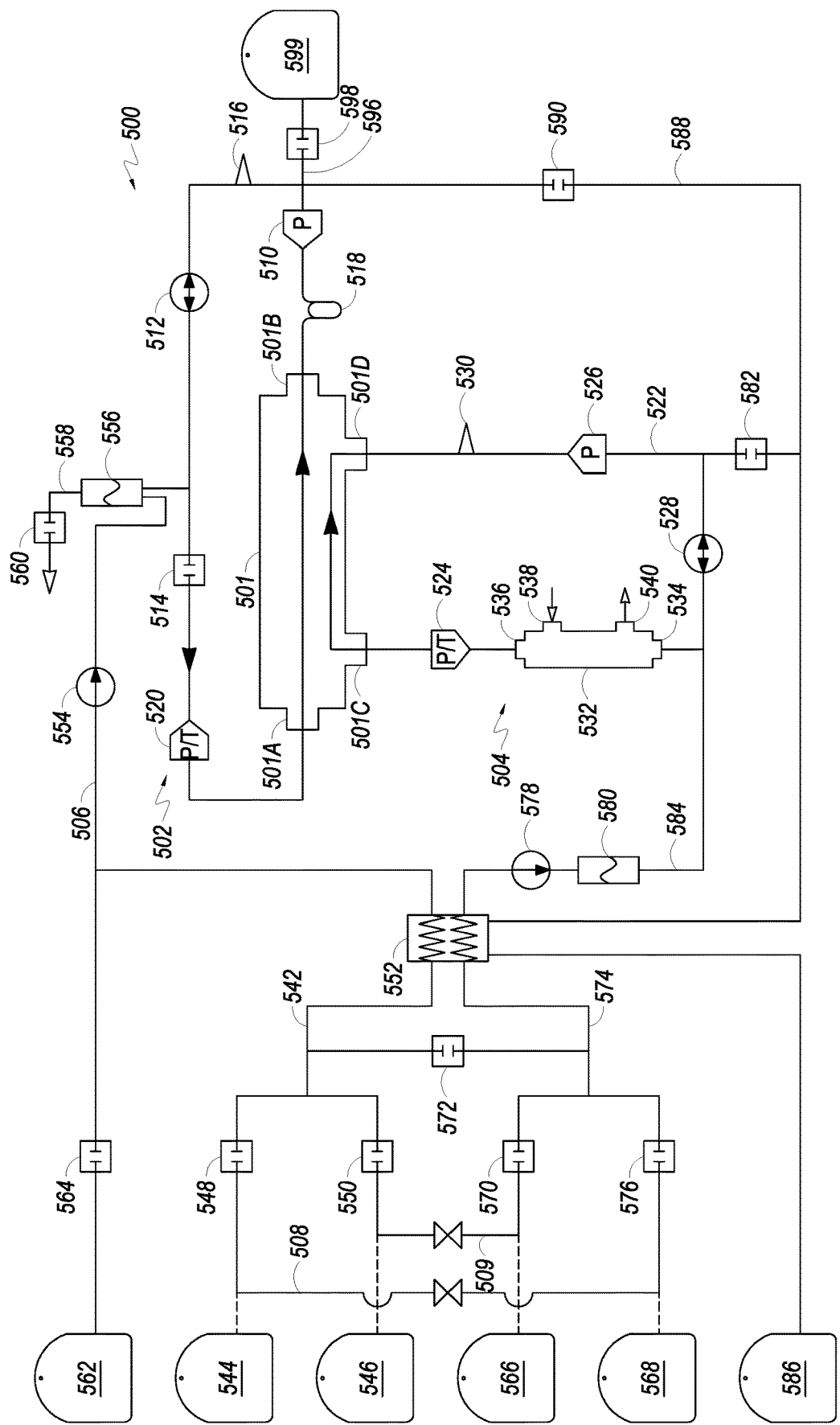
FIG. 5 depicts a schematic of a cell expansion system, in accordance with embodiments.
Figure 6:
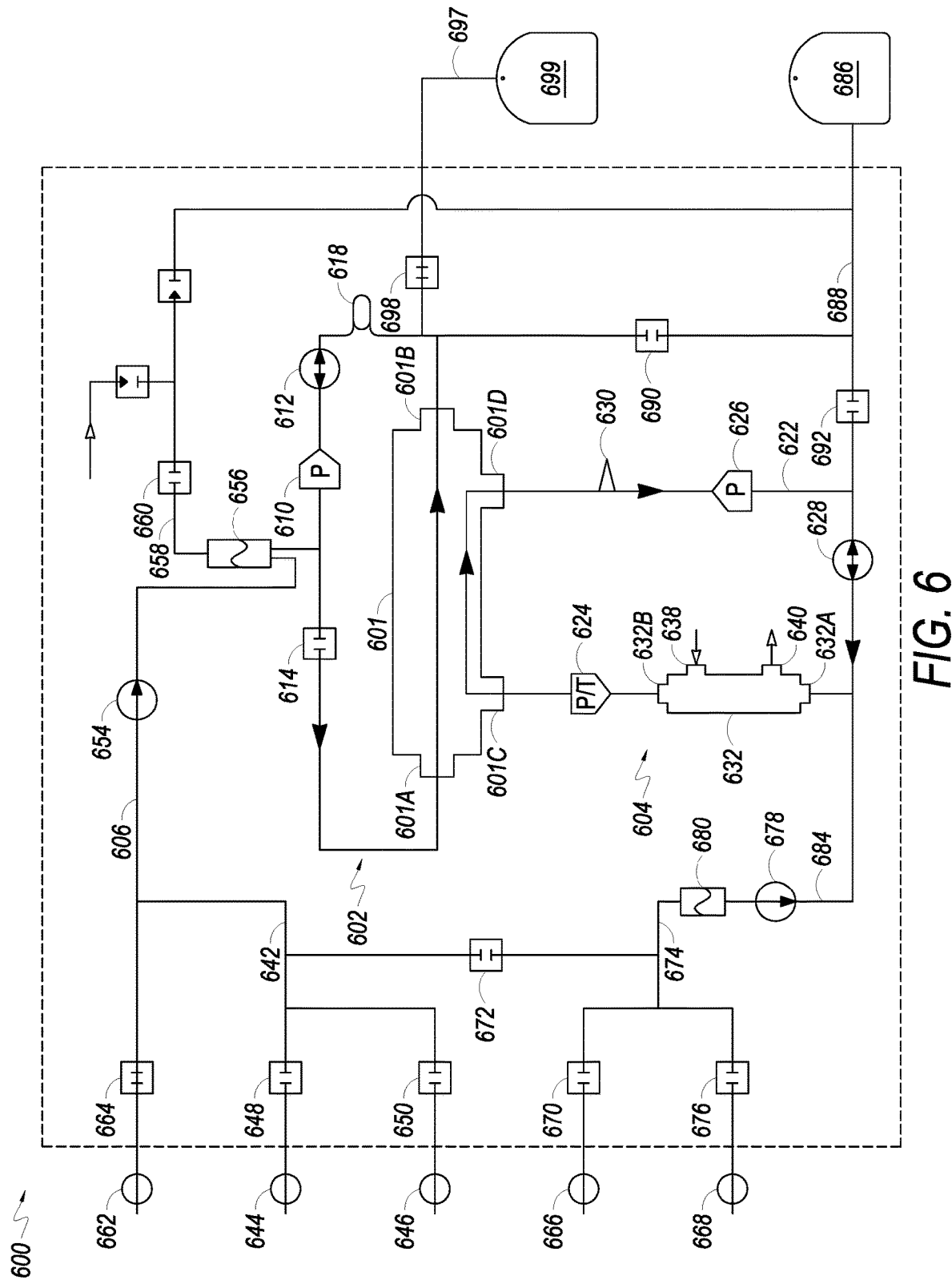
FIG. 6 illustrates a schematic of another embodiment of a cell expansion system, in accordance with embodiments.

FIG. 5 illustrates a schematic of an embodiment of a cell expansion system 500, and FIG. 6 illustrates a schematic of another embodiment of a cell expansion system 600. In the embodiments shown in FIGS. 5 and 6, and as described below, the cells are grown in the IC space. However, the disclosure is not limited to such examples and may in other embodiments provide for cells to be grown in the EC space. In yet other embodiments, such as when co-culturing cells, first cells may be grown in the EC space, while second cells may be grown in the IC space. Co-culturing of cells may also be performed by growing first cells and second cells in the EC space, or growing first cells and second cells in the IC space.

FIG. 5 illustrates a CES 500, which includes first fluid circulation path 502 (also referred to as the "intracapillary loop" or "IC loop") and second fluid circulation path 504 (also referred to as the "extracapillary loop" or "EC loop"), according to embodiments. First fluid flow path 506 may be fluidly associated with hollow fiber bioreactor 501 to form, at least in part, first fluid circulation path 502. Fluid flows into hollow fiber bioreactor 501 through IC inlet port 501A, through hollow fibers in hollow fiber bioreactor 501, and exits via IC outlet port 501B. Pressure gauge 510 measures the pressure of media leaving hollow fiber bioreactor 501. Media flows through IC circulation pump 512 which may be used to control the rate of media flow/rate of fluid circulation. IC circulation pump 512 may pump the fluid in a first direction (e.g., clockwise) or second direction opposite the first direction (e.g., counter clockwise). Exit port 501B may be used as an inlet in the reverse direction. Media entering the IC loop 502 may then enter through valve 514. As those skilled in the art will appreciate, additional valves and/or other devices may be placed at various locations to isolate and/or measure characteristics of the media along portions of the fluid paths. Accordingly, it is to be understood that the schematic shown represents one possible configuration for various elements of the CES 500, and modifications to the schematic shown are within the scope of the one or more present embodiments.

With regard to the IC loop 502, samples of media may be obtained from sample port 516 or sample coil 518 during operation. Pressure/temperature gauge 520 disposed in first fluid circulation path 502 allows detection of media pressure and temperature during operation. Media then returns to IC inlet port 501A to complete fluid circulation path 502. Cells grown/expanded in hollow fiber bioreactor 501 may be flushed out of hollow fiber bioreactor 501 into harvest bag 599 through valve 598 or redistributed within the hollow fibers for further growth.

Fluid in second fluid circulation path 504 enters hollow fiber bioreactor 501 via EC inlet port 501C, and leaves hollow fiber bioreactor 501 via EC outlet port 501D. Media in the EC loop 504 may be in contact with the outside of the hollow fibers in the hollow fiber bioreactor 501, thereby allowing diffusion of small molecules into and out of the hollow fibers.

Pressure/temperature gauge 524 disposed in the second fluid circulation path 504 allows the pressure and temperature of media to be measured before the media enters the EC space of hollow fiber bioreactor 501. Pressure gauge 526 allows the pressure of media in the second fluid circulation path 504 to be measured after it leaves hollow fiber bioreactor 501. With regard to the EC loop, samples of media may be obtained from sample port 530 or a sample coil during operation.

In embodiments, after leaving EC outlet port 501D of hollow fiber bioreactor 501, fluid in second fluid circulation path 504 passes through EC circulation pump 528 to oxygenator or gas transfer module 532. EC circulation pump 528 may also pump the fluid in opposing directions. Second fluid flow path 522 may be fluidly associated with oxygenator or gas transfer module 532 via oxygenator inlet port 534 and oxygenator outlet port 536. In operation, fluid media flows into oxygenator or gas transfer module 532 via oxygenator inlet port 534, and exits oxygenator or gas transfer module 532 via oxygenator outlet port 536. Oxygenator or gas transfer module 532 adds oxygen to and removes bubbles from media in the CES 500. In various embodiments, media in second fluid circulation path 504 may be in equilibrium with gas entering oxygenator or gas transfer module 532. The oxygenator or gas transfer module 532 may be any appropriately sized oxygenator or gas transfer device. Air or gas flows into oxygenator or gas transfer module 532 via filter 538 and out of oxygenator or gas transfer device 532 through filter 540. Filters 538 and 540 reduce or prevent contamination of oxygenator or gas transfer module 532 and associated media. Air or gas purged from the CES 500 during portions of a priming sequence may vent to the atmosphere via the oxygenator or gas transfer module 532.

In the configuration depicted for CES 500, fluid media in first fluid circulation path 502 and second fluid circulation path 504 flows through hollow fiber bioreactor 501 in the same direction (a co-current configuration). The CES 500 may also be configured to flow in a counter-current configuration.

In accordance with at least one embodiment, media, including cells (from bag 562), and fluid media from bag 546 may be introduced to first fluid circulation path 502 via first fluid flow path 506. Fluid container 562 (e.g., Cell Inlet Bag or Saline Priming Fluid for priming air out of the system) may be fluidly associated with the first fluid flow path 506 and the first fluid circulation path 502 via valve 564.

Fluid containers, or media bags, 544 (e.g., Reagent) and 546 (e.g., IC Media) may be fluidly associated with either first fluid inlet path 542 via valves 548 and 550, respectively, or second fluid inlet path 574 via valves 548, 550, and 570. First and second sterile sealable input priming paths 508 and 509 are also provided. An air removal chamber (ARC) 556 may be fluidly associated with first circulation path 502. The air removal chamber 556 may include one or more ultrasonic sensors including an upper sensor and lower sensor to detect air, a lack of fluid, and/or a gas/fluid interface, e.g., an air/fluid interface, at certain measuring positions within the air removal chamber 556. For example, ultrasonic sensors may be used near the bottom and/or near the top of the air removal chamber 556 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 500 during portions of the priming sequence or other protocols may vent to the atmosphere out air valve 560 via line 558 that may be fluidly associated with air removal chamber 556.

EC media (from bag 568) or wash solution (from bag 566) may be added to either the first or second fluid flow paths. Fluid container 566 may be fluidly associated with valve 570 that may be fluidly associated with first fluid circulation path 502 via distribution valve 572 and first fluid inlet path 542. Alternatively, fluid container 566 may be fluidly associated with second fluid circulation path 504 via second fluid inlet path 574 and EC inlet path 584 by opening valve 570 and closing distribution valve 572. Likewise, fluid container 568 may be fluidly associated with valve 576 that may be fluidly associated with first fluid circulation path 502 via first fluid inlet path 542 and distribution valve 572. Alternatively, fluid container 568 may be fluidly associated with second fluid inlet path 574 by opening valve 576 and closing valve distribution 572. An optional heat exchanger 552 may be provided for media reagent or wash solution introduction.

In the IC loop, fluid may be initially advanced by the IC inlet pump 554. In the EC loop, fluid may be initially advanced by the EC inlet pump 578. An air detector 580, such as an ultrasonic sensor, may also be associated with the EC inlet path 584.

In at least one embodiment, first and second fluid circulation paths 502 and 504 are connected to waste line 588. When valve 590 is opened, IC media may flow through waste line 588 and to waste or outlet bag 586. Likewise, when valve 582 is opened, EC media may flow through waste line 588 to waste or outlet bag 586.

In embodiments, cells may be harvested via cell harvest path 596. Here, cells from hollow fiber bioreactor 501 may be harvested by pumping the IC media containing the cells through cell harvest path 596 and valve 598 to cell harvest bag 599.

Various components of the CES 500 may be contained or housed within a machine or housing, such as cell expansion machine 202 (FIGS. 2 and 3), wherein the machine maintains cells and media at a predetermined temperature.

Turning to FIG. 6, a schematic of another embodiment of a cell expansion system 600 is shown. CES 600 includes a first fluid circulation path 602 (also referred to as the "intracapillary loop" or "IC loop") and second fluid circulation path 604 (also referred to as the "extracapillary loop" or "EC loop"). First fluid flow path 606 may be fluidly associated with hollow fiber bioreactor 601 to form first fluid circulation path 602. Fluid flows into hollow fiber bioreactor 601 through IC inlet port 601A, through hollow fibers in hollow fiber bioreactor 601, and exits via IC outlet port 601B. Pressure sensor 610 measures the pressure of media leaving hollow fiber bioreactor 601. In addition to pressure, sensor 610 may, in embodiments, also be a temperature sensor that detects the media pressure and temperature during operation.

Media flows through IC circulation pump 612 which may be used to control the rate of media flow or rate of circulation. IC circulation pump 612 may pump the fluid in a first direction (e.g. counter clockwise) or second direction opposite the first direction (e.g., clockwise). Exit port 601B may be used as an inlet in the reverse direction. Media entering the IC loop may flow through valve 614. As those skilled in the art will appreciate, additional valves and/or other devices may be placed at various locations to isolate and/or measure characteristics of the media along portions of the fluid paths. Samples of media may be obtained from sample coil 618 during operation. Media then returns to IC inlet port 601A to complete fluid circulation path 602.

Cells grown/expanded in hollow fiber bioreactor 601 may be flushed out of hollow fiber bioreactor 601 into harvest bag 699 through valve 698 and line 697. Alternatively, when valve 698 is closed, the cells may be redistributed within hollow fiber bioreactor 601 for further growth. It is to be understood that the schematic shown represents one possible configuration for various elements of the CES 600, and modifications to the schematic shown are within the scope of the one or more present embodiments.

Fluid in second fluid circulation path 604 enters hollow fiber bioreactor 601 via EC inlet port 601C and leaves hollow fiber bioreactor 601 via EC outlet port 601D. Media in the EC loop may be in contact with the outside of the hollow fibers in the hollow fiber bioreactor 601, thereby allowing diffusion of small molecules into and out of the hollow fibers that may be within chamber 601, according to an embodiment.

Pressure/temperature sensor 624 disposed in the second fluid circulation path 604 allows the pressure and temperature of media to be measured before the media enters the EC space of the hollow fiber bioreactor 601. Sensor 626 allows the pressure and/or temperature of media in the second fluid circulation path 604 to be measured after it leaves the hollow fiber bioreactor 601. With regard to the EC loop, samples of media may be obtained from sample port 630 or a sample coil during operation.

After leaving EC outlet port 601D of hollow fiber bioreactor 601, fluid in second fluid circulation path 604 passes through EC circulation pump 628 to oxygenator or gas transfer module 632. EC circulation pump 628 may also pump the fluid in opposing directions, according to embodiments. Second fluid flow path 622 may be fluidly associated with oxygenator or gas transfer module 632 via an inlet port 632A and an outlet port 632B of oxygenator or gas transfer module 632. In operation, fluid media flows into oxygenator or gas transfer module 632 via inlet port 632A, and exits oxygenator or gas transfer module 632 via outlet port 632B. Oxygenator or gas transfer module 632 adds oxygen to and removes bubbles from media in the CES 600.

In various embodiments, media in second fluid circulation path 604 may be in equilibrium with gas entering oxygenator or gas transfer module 632. The oxygenator or gas transfer module 632 may be any appropriately sized device useful for oxygenation or gas transfer. Air or gas flows into oxygenator or gas transfer module 632 via filter 638 and out of oxygenator or gas transfer device 632 through filter 640. Filters 638 and 640 reduce or prevent contamination of oxygenator or gas transfer module 632 and associated media. Air or gas purged from the CES 600 during portions of a priming sequence may vent to the atmosphere via the oxygenator or gas transfer module 632.

In the configuration depicted for CES 600, fluid media in first fluid circulation path 602 and second fluid circulation path 604 flows through hollow fiber bioreactor 601 in the same direction (a co-current configuration). The CES 600 may also be configured to flow in a counter-current configuration.

In accordance with at least one embodiment, media, including cells (from a source such as a cell container, e.g. a bag) may be attached at attachment point 662, and fluid media from a media source may be attached at attachment point 646. The cells and media may be introduced into first fluid circulation path 602 via first fluid flow path 606.

Attachment point 662 may be fluidly associated with the first fluid flow path 606 via valve 664, and attachment point 646 may be fluidly associated with the first fluid flow path 606 via valve 650. A reagent source may be fluidly connected to point 644 and be associated with fluid inlet path 642 via valve 648, or second fluid inlet path 674 via valves 648 and 672.

Air removal chamber (ARC) 656 may be fluidly associated with first circulation path 602. The air removal chamber 656 may include one or more sensors including an upper sensor and lower sensor to detect air, a lack of fluid, and/or a gas/fluid interface, e.g., an air/fluid interface, at certain measuring positions within the air removal chamber 656. For example, ultrasonic sensors may be used near the bottom and/or near the top of the air removal chamber 656 to detect air, fluid, and/or an air/fluid interface at these locations. Embodiments provide for the use of numerous other types of sensors without departing from the spirit and scope of the present disclosure. For example, optical sensors may be used in accordance with embodiments of the present disclosure. Air or gas purged from the CES 600 during portions of a priming sequence or other protocol(s) may vent to the atmosphere out air valve 660 via line 658 that may be fluidly associated with air removal chamber 656.

An EC media source may be attached to EC media attachment point 668 and a wash solution source may be attached to wash solution attachment point 666, to add EC media and/or wash solution to either the first or second fluid flow path. Attachment point 666 may be fluidly associated with valve 670 that may be fluidly associated with first fluid circulation path 602 via valve 672 and first fluid inlet path 642. Alternatively, attachment point 666 may be fluidly associated with second fluid circulation path 604 via second fluid inlet path 674 and second fluid flow path 684 by opening valve 670 and closing valve 672. Likewise, attachment point 668 may be fluidly associated with valve 676 that may be fluidly associated with first fluid circulation path 602 via first fluid inlet path 642 and valve 672. Alternatively, fluid container 668 may be fluidly associated with second fluid inlet path 674 by opening valve 676 and closing valve distribution 672.

In the IC loop, fluid may be initially advanced by the IC inlet pump 654. In the EC loop, fluid may be initially advanced by the EC inlet pump 678. An air detector 680, such as an ultrasonic sensor, may also be associated with the EC inlet path 684.

In at least one embodiment, first and second fluid circulation paths 602 and 604 are connected to waste line 688. When valve 690 is opened, IC media may flow through waste line 688 and to waste or outlet bag 686. Likewise, when valve 692 is opened, EC media may flow to waste or outlet bag 686.

After cells have been grown in hollow fiber bioreactor 601, they may be harvested via cell harvest path 697. Here, cells from hollow fiber bioreactor 601 may be harvested by pumping the IC media containing the cells through cell harvest path 697, with valve 698 open, into cell harvest bag 699.

Various components of the CES 600 may be contained or housed within a machine or housing, such as cell expansion machine 202 (FIGS. 2 and 3), wherein the machine maintains cells and media at a predetermined temperature. It is further noted that, in embodiments, components of CES 600 and CES 500 (FIG. 5) may be combined. In other embodiments, a CES may include fewer or additional components than those shown in FIGS. 5 and 6 and still be within the scope of the present disclosure. In embodiments, portions of CES 500 and 600 may be implemented by one or more features of the QUANTUM® Cell Expansion System (CES), manufactured by Terumo BCT, Inc. of Lakewood, CO.

In one specific embodiment of using CES 600, hematopoietic stem cells (HSC's), e.g., CD34+ cells, may be expanded in an embodiment of CES 600. In this embodiment, HSC's (including CD34+ cells), which may be collected using a leukapheresis process or a manual process (e.g., umbilical cords), may be introduced into the bioreactor 601. The HSC's (including CD34+ cells) may be introduced into the bioreactor 601 through path 602.

In some embodiments, the HSC's (including CD34+ cells) may be subjected to a selection process (e.g., a purification process) before introduction into bioreactor 601. The process may involve the use of a centrifuge, purification column, magnetic selection, chemical selection, etc. Some examples of cell selection/purification procedures include use of isolation columns from, for example, Miltenyi Biotec of Bergisch Gladbach, Germany. In one example, cord blood is first subjected to a cell selection process that selects for HSC's (including CD34+ cells) before the cells are introduced into the bioreactor 601. Other examples may utilize apheresis machines to deplete other cells that may be included with the HSC's (including CD34+ cells) when originally collected. For example, the HSC's may be sourced from cord blood, bone marrow, or peripheral blood. After initial collection, but before being introduced into the bioreactor 601, a volume of HSC's including CD34+ cells may be processed to deplete red blood cells, specific leukocytes, granulocytes, and/or other cells from the volume. These are merely some examples, and embodiments of the present invention are not limited thereto.

In other embodiments, the HSC's (including CD34+ cells) may be added directly to the bioreactor 601 after collection without any additional purification. For example, cord blood (with HSC's) may be added to the bioreactor. In addition to a number of proteins and other bioactive molecules, the cord blood may include HSC's (including CD34+ cells), red blood cells, platelets, granulocytes, and/or leukocytes.

It is noted that in some embodiments, the HSC's may be added to bioreactor 601, after a priming step. As may be appreciated, the cells being expanded may not be adherent and therefore it may not be required that they adhere to the hollow fiber walls of bioreactor 601 for expansion/proliferation. In these embodiments, it may be unnecessary to coat the inside of the hollow fibers with a coating to promote adhesion, e.g., fibronectin. In these embodiments, the HSC's (including CD34+ cells) (purified or unpurified) may be introduced into the bioreactor 601 after a priming step and without a bioreactor coating step. If the cells were adherent cells, a coating step may be performed after the priming step and before introduction of the HSC's.

Once in the bioreactor 601, the cells may be exposed to growth factors, activators, hormones, reagents, proteins, and/or other bioactive molecules that may aid in the expansion of the cells. In one example, a co-culture cell line may have been previously grown/introduced, in the bioreactor 601, to optimize the conditions for growing the HSC's (including CD34+ cells). In one specific embodiment, human mesenchymal stem cells (hMSC's) may be co-cultured with the HSC's (including CD34+ cells) to promote growth of CD34+ cells. Without being bound by theory, it is believed that MSC's may emit factors (e.g., SDF-1 factors) that interact with HSC's (e.g., CD34+ cells) and promote proliferation of these cells. In some embodiments, use of the co-cultured hMSC's may involve a growing process that is performed initially, under conditions optimized for proliferating the hMSC's, before the HSC's (including CD34+ cells) are introduced into the bioreactor 601. The hMSC's may be derived in embodiments from bone marrow, peripheral blood, cord cells, adipose tissue, and/or molar tissue.

In addition to co-culture cells, a supplement including one or more growth factors, activators, hormones, reagents, proteins, and/or other bioactive molecules may be added to bioreactor 601 to grow and expand the HSC's. The supplement may be added as a single volume addition or over a period of time (e.g., continuously, intermittently, or on a regular schedule). In one embodiment, a combination of cytokines and/or other proteins, e.g., recombinant cytokines, hormones, etc., may be included as part of the supplement. As one example, a supplement may include one or more of: recombinant human Flt3 ligand (rhFlt-3L), recombinant human stem cell factor (rhSCF), recombinant human thrombopoietin (rhTPO), recombinant human (rh) Glial-derived neurotrophic factors and/or combinations thereof. One example of a supplement that may be used with embodiments is STEMCELL2MAX™ supplement (stemcell2MAX, Cantanhede, Portugal).

It is noted that in some embodiments, the combination of factors may be included in the media in which the cells are suspended. For example, the HSC's may be suspended in media and introduced into the bioreactor in the media. In embodiments, the media may include a combination of growth factors that aid in proliferation of the HSC's.

After the cells have been introduced into the bioreactor with the supplement, co-culture cells, and/or other material for expanding the cells, the cells are allowed to expand in bioreactor 601. During the expansion, there may be a number of materials that may be added or removed from bioreactor 601. As one example, additional proteins (e.g., cytokines) may be may be added to bioreactor 601. In some embodiments, more than one protein or other bioactive agent may be used. The additional material may be added individually, at the same time, at different times, or may be combined and added in combination.

It is noted that some embodiments may provide for adding material more directly into the bioreactor 601, such as through port 618. In other embodiments, however, the materials may be added in a location, e.g., through path 606, so that the materials may be perfused more slowly into bioreactor 601.

In addition to materials for aiding in growing the HSC's (including CD34+ cells), the HSC's may also be fed, such as by addition of a media that may include a number of nutrients. In some embodiments, the media may be commercially available media that may include serum. In other embodiments, the media may be serum free and include other additives. The media may be modified by the addition of other materials, some non-limiting examples including salts, serum, proteins, reagents, bioactive molecules, nutrients, etc. One example of media that may be used to feed the HSC's (including CD34+ cells) includes CELLGRO® serum free media (CellGenix, Freiburg, Germany).

In some embodiments, while the co-culture cells are located in the IC space, feeding may occur in the EC space. Feeding through the EC space may, in embodiments, reduce the amount of force that may be felt by the cells from circulating fluid in the IC space. Circulation of media in the EC space may, in embodiments, provide sufficient nutrients for the expansion of the HSC's (including CD34+ cells).

As part of the expansion of the HSC's (including CD34+ cells), other conditions such as temperature, pH, oxygen concentration, carbon dioxide concentration, waste concentration, metabolite concentration etc. may also be controlled in bioreactor 601. In some embodiments, the flow rates of the EC side, e.g., path 604 may be used to control various parameters. For example, if it is desired to reduce waste or metabolite concentrations on the IC side, where the cells are growing, flow rate on the EC side may be increased to ensure that the waste and/or metabolites are removed from the IC side by migration through the hollow fibers from the IC side to the EC side.

After the CD34+ cells have been expanded, the cells may be removed from the bioreactor 601. The CD34+ cells may be collected in container 699. In embodiments, the collected CD34+ cells may be administered to a patient to reestablish hematopoiesis. Some non-limiting examples including patients undergoing treatment for various cancers, e.g., leukemia, myelodysplasia, non-Hodgkin lymphoma, etc., which may effect hematopoiesis. The cells may be administered with other compounds or molecules.

In some embodiments, use of CES 600 may provide advantages in growing HSC's (including CD34+ cells) over conventional processes. For example, the use of hollow fibers allows close cell to cell communication, which may enhance the growth of the CD34+ cells to start and continue to proliferate. Also, the use of a hollow fiber bioreactor, such as bioreactor 601, may provide a large surface area for cell growth, which may yield a higher concentration or higher volume of CD34+ cells.

Further, the conditions in bioreactor 601 may be controlled using a number of different components of the CES 600, including IC flow rates and EC flow rates. Also, CES 600 provides various locations for the addition of materials, which allows more direct, or indirect, e.g., perfusion, of cytokines into bioreactor 601.

Additionally, CES 600 provides a closed system. That is, the steps for growing the CD34+ cells may be performed without direct exposure to the ambient environment, which may contaminate the cells, or be contaminated by the cells or materials used in growing the cells. It is also believed that some embodiments may provide for using a smaller starting concentration of CD34+ cells for expansion, compared to other methods/systems. In these embodiments, CD34+ cells may also be expanded to yield larger amounts than from other methods/systems. It is also believed that some embodiments may provide for shortening the time for growing an effective dose of CD34+ cells.

Figure 7:
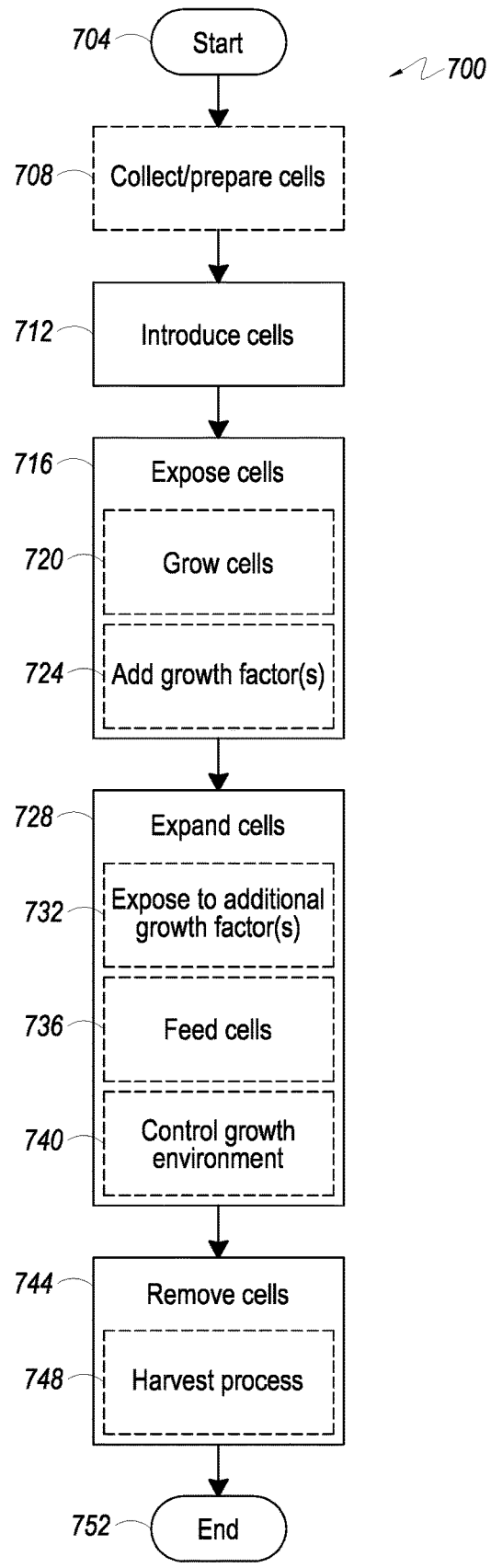
FIG. 7 illustrates a flow of a process for expanding cells according to embodiments.
Figure 8:
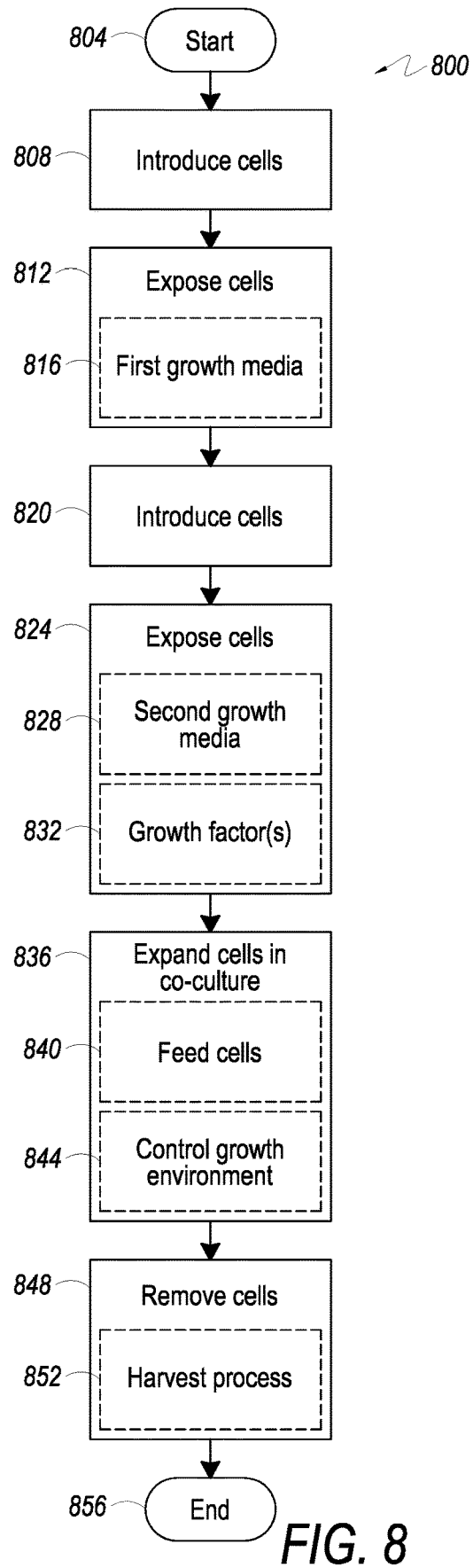
FIG. 8 illustrates a flow of a process for expanding cells according to another embodiment.
Figure 9:
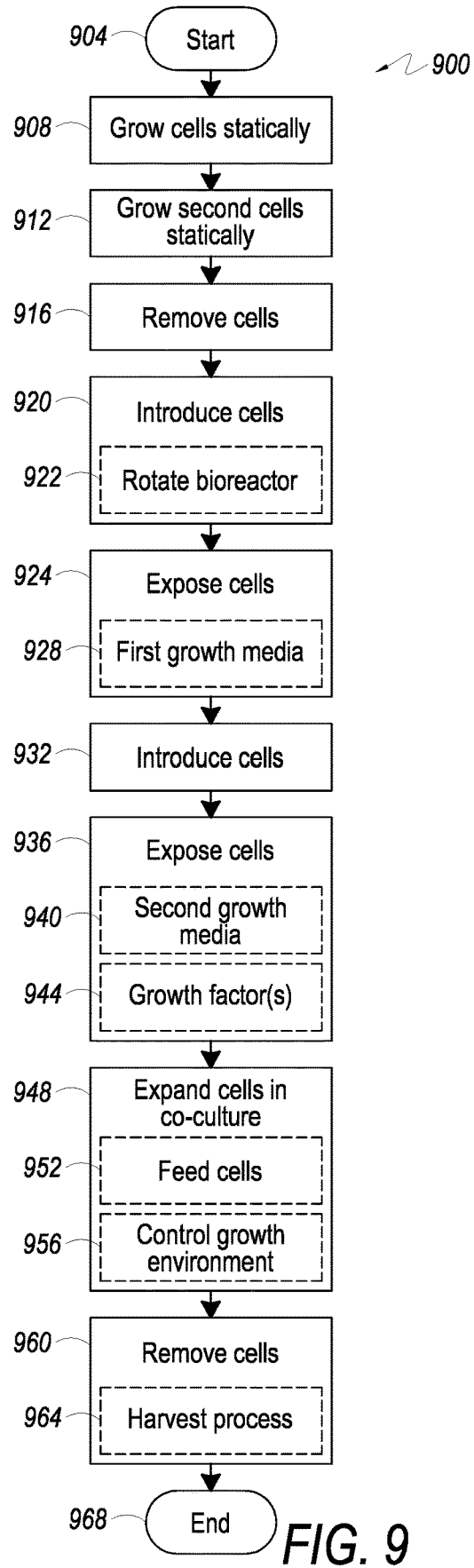
FIG. 9 illustrates a flow of a process for expanding cells according to yet another embodiment.

FIGS. 7-9 illustrate flows 700, 800, and 900 that may be performed in embodiments to grow cells, e.g., HSC. Although specific devices may be described below for performing steps in flows 700, 800, and 900, embodiments are not limited thereto. For example, some steps may be described as performed by parts of a cell expansion system (e.g., CES's 500 or 600) or a processor (1100 (FIG. 11)), which may execute steps based on software provided as processor executable instructions. This is done merely for illustrative purposes, and flows 700, 800, and 900 are not limited to being performed by any specific device.

Flow 700 starts at step 704 and proceeds to optional step 708 where cells (e.g., HSC's including CD34+ cells) may be collected/prepared. As one example, step 708 may involve an apheresis process, e.g., a leukapheresis process. In one specific embodiment, an apheresis process is performed as part of step 708. Devices capable of collecting the cells include in an apheresis process include the SPECTRA OPTIA® apheresis system, COBE® spectra apheresis system, and the TRIMA ACCEL® automated blood collection system, all manufactured by Terumo BCT, of Lakewood, Colorado.

In other embodiments, optional step 708 may involve thawing or otherwise preparing cells (e.g., from cord blood). In some embodiments, the preparation of the cord blood cells may involve processing the cord blood cells through a selection process that selects CD34+ cells. The process may be either a positive or a negative selection process. The process may involve the use of purification columns, magnetic columns, functionalized magnetic beads, reagents, or other materials that separate CD34+ cells from other cells. As one example, the selection process may involve the use of magnetic beads, functionalized with antigens, and devices such as the CLINIMACS PRODIGY® system (Miltenyi Biotec, Bergisch Gladbach, Germany) that utilizes a magnetic column to complete the separation.

In other embodiments, apheresis machines may be used to deplete other cells that may be included with the cells when originally collected. For example, the cells may be sourced from cord blood, bone marrow, or peripheral blood. After initial collection, but before being introduced into a bioreactor, a volume of target cells may be processed to deplete red blood cells, specific leukocytes, granulocytes, and/or other cells from the volume before introduction into a bioreactor. This is merely one example and embodiments may utilize other materials and systems to effect the separation.

Flow 700 passes from step 708 to step 712, where cells may be introduced into a cell expansion system, in particular, a bioreactor of a cell expansion system. As noted above, in some embodiments, flow 700 may begin at step 712. In embodiments, the bioreactor may be a hollow fiber bioreactor such as bioreactor 100 (FIG. 1). In these embodiments, step 712 may involve flowing cells into one or more individual hollow fibers. Step 712 may involve the use of a processor, pumps, valves, fluid conduit, etc. to introduce cells into a bioreactor. In one embodiment, step 712 may involve opening valves (e.g., 564, 514, 664, and/or 614) and activating pumps (e.g., 554 and 654).

After step 712, flow 700 passes to step 716 where the cells are exposed to one or more growth conditions. As may be appreciated, certain cell types require specific growth conditions to expand. The growth conditions may for example include exposure to certain proteins. One example of this type of cell includes CD34+ cells. Step 716 provides for exposing cells to any necessary growth factors, proteins, reagents, nutrients, etc. that may promote cell expansion and growth.

Step 716 may involve a number of steps that may be performed as part of step 716, or precede step 716. For example, in some embodiments, step 720 may be performed to grow co-culture cells that may generate material that promotes growth of the target cell line. In one embodiment, step 720 may be performed prior to step 716, or even prior to step 708. In one specific example, human mesenchymal stem cells (hMSC's) may be grown in the bioreactor. In these embodiments, step 720 may involve a number of steps (e.g., collecting hMSC's from bone marrow, peripheral blood, cord cells, adipose tissue, and/or molar tissue) that result in co-culture cells being present in the bioreactor during step 716. As may be appreciated, these steps may be performed prior to step 712.

With respect to growing the co-culture cells, several steps for conditioning the bioreactor for growing the co-culture cells may be performed. In embodiments, the steps may include priming the bioreactor, coating the bioreactor with materials that promote the attachment of the co-culture cells (e.g., when the co-culture cells are adherent cells), washing to remove materials prior to introduction of the co-culture cells into the bioreactor, attaching the co-culture cells, and expanding the co-culture cells.

In other embodiments, step 716 may involve step 724, where growth factors may be added to the bioreactor. As may be appreciated, in some embodiments, one or more growth factors, e.g., cytokines, may be added to promote the proliferation of cells. As one example, when growing CD34+ cells, the growth factor(s) may include one or more of: recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. This is merely one example and in other embodiments, different growth factors, combination of growth factors, or other proteins may be used as part of step 724.

In one embodiment, at least a portion of the growth factors may be introduced with the cells at step 712. For example, the media in which the cells are in when introduced into the bioreactor may be conditioned with a combination of growth factors including one or more of recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. In these embodiments, step 716, and optional step 724, may involve supplementing growth factors that may have already been added to the bioreactor with the cells.

After step 716, flow may pass to step 728, where cells are expanded, i.e., proliferated. Step 728 may involve a number of sub-steps. For example, at sub-step 732, the cells may be exposed to additional growth factors, proteins, bioactive molecules, etc. The exposure may provide for the cells to continue to proliferate.

In embodiments, step 728 may occur during a period of time of several hours, several days, or even several weeks. During this period of time, the various sub-steps (e.g., 732, 736, and/or 740) may be performed at various times during this period. For example, during the period, additional substances such as growth factors may be perfused or directly injected into the bioreactor to supplement and continue to expose the cells and promote proliferation.

Step 728 may also involve a feeding cells step 736. Step 736 may involve adding various nutrients, including glucose, phosphates, salts, etc. Step 736 may in embodiments involve sensing a concentration of a nutrient and in response to a relatively low concentration, adding nutrient(s) to the bioreactor. Step 736 may involve the use of a processor, pumps, valves, fluid conduit, etc. to add nutrients to feed the cells. Alternatively, the additions of nutrients, such as glucose may be added based on a predetermined schedule.

In some embodiments, step 728 may involve circulating media in the EC space. The media may include nutrients necessary for expansion of the CD34+ cells. Feeding through the EC space may, in embodiments, reduce the amount of force that may be felt by the cells if media is circulated in the IC space. Circulation of media in the EC space may, in embodiments, provide sufficient nutrients (e.g., glucose) for the expansion of the HSC's (including CD34+ cells) through diffusion of the nutrients through hollow fibers. In other embodiments, step 728 may involve circulating media, with nutrients (e.g., glucose), in the IC space for more direct feeding.

Step 740 may involve controlling the growth environment of the bioreactor. As may be appreciated, in addition to nutrients, the environment for optimizing growth of cells may involve a number of different parameters. For example, the temperature, pH, oxygen concentration, carbon dioxide concentration, waste concentration, metabolite concentration etc. may be monitored and controlled as part of step 740. In one specific embodiment, a flow rate of a fluid flowing through an extracapillary space (EC) side of a bioreactor may be used in controlling the pH, oxygen concentration, carbon dioxide concentration, waste concentration, metabolite concentration etc. in the intracapillary space where the cells are expanding.

Flow 700 proceeds from step 740 to step 744 where cells are removed from the bioreactor. Step 744 may involve a number of sub-steps. For example, a harvest process 748, which itself includes a number of steps, may be performed as part of step 744. In embodiments, step 748 may involve changing circulation rates on the intracapillary space (IC) and extra capillary space (EC) sides of the bioreactor. In other embodiments, step 744 may involve circulating various materials to ensure that any cells that may have attached themselves to the inside surface of fibers are released and removed from the bioreactor. As one example, a protease may be added to break down proteins, such as glycoproteins that may aid in binding of the cells to the fibers.

In one embodiment, as part of a harvest process 748, fluid within the bioreactor (e.g., intracapillary space) may be circulated at a relatively high rate. The circulation of the fluid may promote suspension of the cell expanded at step 728. The circulation may occur for a predetermined period of time to ensure that the expanded cells are suspended in the fluid and as many as possible may be recovered from the bioreactor. Flow 700 ends at step 752.

Flow 800 may be performed in embodiments to grow cells, such as CD34+ cells in co-culture. In embodiments, the co-culture may improve growth of the CD34+ cells. Flow 800 starts at step 804 and proceeds to step 808 where first cells (e.g., human mesenchymal stem cells (hMSC's)) may be introduced into a bioreactor. In embodiments, the bioreactor (e.g., bioreactor 100 (FIG. 1)) may be a hollow fiber bioreactor that includes a number of hollow fibers (e.g., hollow fibers 116 (FIG. 1)).

In embodiments, hollow fibers in the hollow fiber bioreactor may be conditioned prior to step 808. For example, in order to allow the hMSC's to adhere to the interior wall of the hollow fibers, the hollow fibers may be coated with for example a glycoproteins (fibronectin, collagen). The coating process may involve a number of substeps.

The cells introduced at step 808 may be introduced into the intracapillary space, e.g., in the interior of the hollow fibers, of the hollow fiber bioreactor. Step 808 may involve the use of a processor (1100, (FIG. 11)), pumps, valves, fluid conduit, etc. to introduce cells into a bioreactor. In one embodiment, step 808 may involve opening valves (e.g., 564, 514, 664, and/or 614) and activating pumps (e.g., 554 and 654).

In other embodiments, step 808 may introduce the cells into an extracapillary space, e.g., on the outside of the hollow fibers, of the hollow fiber bioreactor. Step 808 may involve the use of a processor (1100, (FIG. 11)), pumps, valves, fluid conduit, etc. to introduce cells into a bioreactor. In one embodiment, step 808 may involve opening valves (e.g., 570, 576, 670, and/or 676) and activating pumps (e.g., 578 and/or 678).

Flow passes from step 808 to step 812, where the first cells are exposed to first growth conditions. The first growth conditions may be optimized for growing the first cells introduced at step 808. For example, step 812 may involve feeding the first cells with a first growth media (optional step 816) that includes nutrients for growing the first cells. The growth media may include one or more of various nutrients, including glucose, phosphates, salts, etc.

After a predetermined period of time (which may depend on a certain number of the first cells having been grown within the bioreactor), flow 800 passes to 820 where second cells (e.g., HSC's, hematopoietic progenitor cells (CD34+), etc.) may be introduced into the bioreactor. In embodiments, the second cells are introduced into an intracapillary space just like the first cells. In other embodiments, as noted above, the first cells may be in the extracapillary space, while the second cells may be introduced into the intracapillary space.

In some embodiments, prior to introducing second cells, a washout procedure may be performed to remove the previous fluid from the bioreactor. As may be appreciated, the fluid in the bioreactor may include nutrient tailored for growing the first cells. Embodiments may provide for flushing this fluid out of the bioreactor prior to, or as part of step 820, and introducing the second cells in to the bioreactor.

Step 820 may involve the use of a processor (1100, (FIG. 11)), pumps, valves, fluid conduit, etc. to introduce second cells into a bioreactor. In one embodiment, step 820 may involve opening valves (e.g., 564, 514, 664, and/or 614) and activating pumps (e.g., 554 and 654).

Flow passes from step 820 to step 824, where the second cells are exposed to second growth conditions. The second growth conditions may be optimized for growing the second cells introduced at step 820. For example, step 820 may involve feeding the second cells with a second growth media (at optional step 828) that includes nutrients for growing the second cells. The second media may include one or more of various nutrients, including glucose, phosphates, salts, etc.

Additionally, in some embodiments, step 820 may involve the optional step of 832 adding growth factors that promote growth of the second cells, e.g., CD34+ cells. In embodiments, the growth factors, e.g., cytokines, may be added to promote the proliferation of cells. As one example, when growing CD34+ cells, the growth factor(s) may include one or more of: recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. This is merely one example and in other embodiments, different growth factors, combination of growth factors, or other proteins may be used. In embodiments, the growth factors may be added to the intracapillary space of the hollow fiber bioreactor.

In embodiments, at least a portion of the growth factors may be introduced with the cells at step 820. For example, the media in which the cells are in when introduced into the bioreactor may be conditioned with a combination of growth factors including one or more of recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. In these embodiments, step 820, and optional step 832, may involve supplementing growth factors that may have already been added to the bioreactor with the cells.

Flow passes from step 824 to step 836, where cells are expanded in co-culture. Step 836 may involve a number of optional sub-steps. For example, the cells may be fed at optional sub-step 840. Additional glucose or other nutrients may be provided to the cells as they expand in co-culture. At sub-step 844, other conditions may be controlled to expand the cells. For example, temperature, pH, gas concentrations, etc. may be monitored and changed in order to control the environment for expansion of the cells.

Flow 800 proceeds from step 836 to step 848 where cells are removed from the bioreactor. Step 848 may involve a number of sub-steps. For example, a harvest process 852, which itself includes a number of steps, may be performed as part of step 848. In embodiments, step 848 may involve changing circulation rates on the intracapillary space (IC) and extra capillary space (EC) sides of the bioreactor. In other embodiments, step 848 may involve circulating various materials to ensure that any cells that may have attached themselves to the inside surface of fibers are released and removed from the bioreactor. As one example, a protease may be added to break down proteins, such as glycoproteins (fibronectin, collagen) that may aid in binding of the cells to the fibers.

In one embodiment, as part of a harvest process 852, fluid within the bioreactor (e.g., intracapillary space) may be circulated at a relatively high rate. The circulation of the fluid may promote suspension of the cell expanded at step 836. The circulation may occur for a predetermined period of time to ensure that the expanded cells are suspended in the fluid and as many as possible may be recovered from the bioreactor. Flow 800 ends at step 856.

Flow 900 starts at step 904 and proceeds to step 908 where first cells (e.g., human mesenchymal stem cells (hMSC's)) may be grown in a static growth chamber. Step 908 may involve use of a flask or a gas permeable reactor, where fluid is not moved by pumps. Rather, the growth chamber remains stationary and fluid does not flow after being added to the chamber.

Flow 900 may then pass from step 908 to step 912 where second cells are grown statically in the static growth chamber. In embodiments, the second cells may be hematopoietic progenitor cells (e.g., CD34+ cells). After step 912, the second cells, which may have been expanded in the static growth chamber, may be removed from the growth chamber, for additional expansion in a dynamic cell expansion system (e.g., CES's 500 and/or 600) where fluid may be circulated (e.g., automatically) as the cells are expanded.

Flow 900 may then pass to step 920, where first cells (e.g., hMSC's) may be introduced into a hollow fiber bioreactor that includes a number of hollow fibers. The cells introduced at step 920 may be introduced into the interior (lumen) of the hollow fibers.

In embodiments, hollow fibers in the hollow fiber bioreactor may be conditioned prior to step 920. For example, in order to allow the hMSC's to adhere to the interior wall of the hollow fibers, the hollow fibers may be coated with for example a glycoproteins (fibronectin, collagen). The coating process may involve a number of substeps.

Step 920 may involve the use of a processor (1100, (FIG. 11)), pumps, valves, fluid conduit, etc. to introduce first cells into a bioreactor. In one embodiment, step 920 may involve opening valves (e.g., 564, 514, 664, and/or 614) and activating pumps (e.g., 554 and 654).

Step 920 may involve a number of sub-steps. In embodiments, as part of introducing cells into the hollow fiber bioreactor, the bioreactor may be rotated at sub-step 922. For example, in order to have the first cells attach to as much of the interior (lumen) of the hollow fibers as possible, the bioreactor may be rotated in a specific pattern.

Figure 10A:
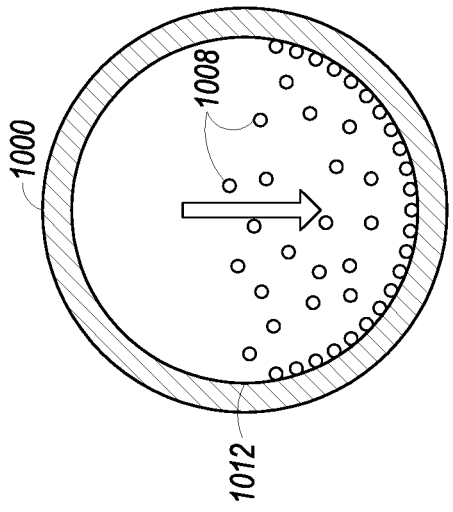
FIGS. 10A-D illustrate a cross section of a hollow fiber during rotation of a bioreactor, according to embodiments.

FIGS. 10A-D illustrate a cross-section of a hollow fiber 1000 (e.g., fibers 116 (FIG. 1)) during a process of introducing, and attaching, first cells to an interior of hollow fibers. In FIG. 10A, fluid 1004 with first cells 1008 is circulated around an intracapillary space of a hollow fiber membrane with a pump (see FIGS. 5 and 6 and description above). As shown in FIG. 10A, initially 1008 cells are distributed throughout the fluid.

Figure 10B:
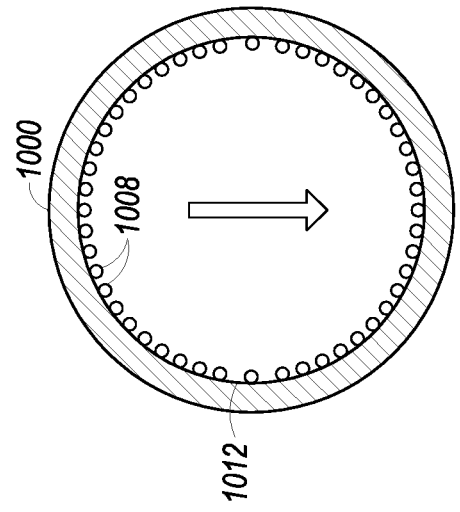

The pump may then be stopped, which results in the first cells settling, and after a period of time, attaching onto a portion of the inside 1012 of the hollow fiber, as shown in FIG. 10B. In embodiments, the hollow fiber may have previously been coated with a compound to promote adhesion of the cells to the hollow fiber inside wall. For example, the lumen of the hollow fiber may have been coated with a glycoprotein, such as fibronectin.

After the first cells 1008 have settled and attached, the bioreactor (and consequently fiber 1000) may be rotated 180 degrees. Examples of methods for rotating a bioreactor when loading cells, in order to distribute cells more evenly on the inside surface of hollow fibers, is described in at least U.S. Pat. No. 9,617,506, issued Apr. 11, 2017, entitled "EXPANDING CELLS IN A BIOREACTOR," which is hereby incorporated by reference in its entirety as if set forth herein in full.

In some embodiments, after the rotation, the pump may be activated again to circulate the remaining, unattached, first cells 1008 in the intracapillary space of the hollow fiber membrane. In other embodiments, the pump may not be reactivated.

Figure 10C:
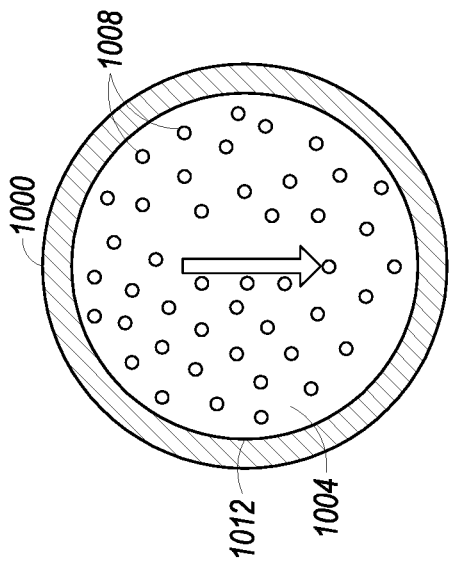
Figure 10D:
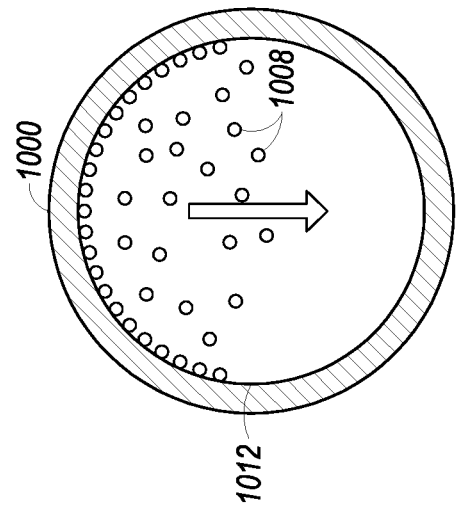

As shown in FIGS. 10C, a second portion of the first cells 1008 may then begin to settle and attach to a second portion of the inside 1012 of the hollow fiber 1000. After a period of time, a second portion of the first cells 1008 may attach as shown in FIG. 10D. In this way, the first cells 1008 (e.g., hMSC's) may be distributed more evenly around an entire inside surface 1012, e.g., both top and bottom of the inside of a hollow fiber.

Referring again to FIG. 9, flow passes from step 920 to step 924, where the first cells are exposed to first growth conditions. The first growth conditions may be optimized for growing the first cells introduced at step 920. For example, step 924 may involve feeding the first cells with a first growth media (optional step 928) that includes nutrients for growing the first cells. The growth media may include one or more of various nutrients, including glucose, phosphates, salts, etc.

After a predetermined period of time (which may depend on a certain number of the first cells having been grown within the bioreactor), flow 900 passes to 932 where second cells (e.g., HSC's, hematopoietic progenitor cells (CD34+) etc.) may be introduced into the bioreactor. In embodiments, the second cells are introduced into an intracapillary space just like the first cells. In other embodiments, as noted above, the first cells may be in the extracapillary space, while the second cells may be introduced into the intracapillary space.

In some embodiments, prior to introducing second cells, a washout procedure may be performed to remove the previous fluid from the bioreactor. As may be appreciated, the fluid in the bioreactor may include nutrient tailored for growing the first cells. Embodiments may provide for flushing this fluid out of the bioreactor prior to, or as part of step 932, and introducing the second cells in to the bioreactor.

Step 932 may involve the use of a processor (1100, (FIG. 11)), pumps, valves, fluid conduit, etc. to introduce second cells into a bioreactor. In one embodiment, step 932 may involve opening valves (e.g., 564, 514, 664, and/or 614) and activating pumps (e.g., 554 and 654).

Flow passes from step 932 to step 936, where the second cells are exposed to second growth conditions. The second growth conditions may be optimized for growing the second cells introduced at step 932. For example, step 936 may involve feeding the second cells with a second growth media (at optional step 940) that includes nutrients for growing the second cells. The second media may include one or more of various nutrients, including glucose, phosphates, salts, etc.

Additionally, in some embodiments, step 936 may involve the step 944 of adding growth factors that promote growth of the second cells, e.g., CD34+ cells. In embodiments, the growth factors, e.g., cytokines, may be added to promote the proliferation of cells. As one example, when growing CD34+ cells, the growth factor(s) may include one or more of: recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. This is merely one example and in other embodiments, different growth factors, combination of growth factors, or other proteins may be used. In embodiments, the growth factors may be added to the intracapillary space of the hollow fiber bioreactor.

In one embodiment, at least a portion of the growth factors may be introduced with the cells at step 936. For example, the media in which the cells are in when introduced into the bioreactor may be conditioned with a combination of growth factors including one or more of recombinant human Flt3 ligand (rhFlt-3L), recombinant human stem cell factor (rhSCF), recombinant human thrombopoietin (rhTPO), recombinant human (rh) Glial-derived neurotrophic factors, and combinations thereof. In these embodiments, step 936, and optional step 944, may involve supplementing growth factors that may have already been added to the bioreactor with the cells.

Flow passes from step 936 to step 948, where cells are expanded in co-culture. Step 948 may involve a number of optional sub-steps. For example, the cells may be fed at optional sub-step 952. Additional glucose or other nutrients may be provided to the cells as they expand in co-culture. At sub-step 956, other conditions may be controlled to expand the cells. For example, temperature, pH, gas concentrations, etc. may be monitored and changed in order to control the environment for expansion of the cells.

Flow 900 proceeds from step 948 to step 960 where cells are removed from the bioreactor. Step 960 may involve a number of sub-steps. For example, a harvest process 964, which itself includes a number of steps, may be performed as part of step 960. In embodiments, step 964 may involve changing circulation rates on the intracapillary space (IC) and extra capillary space (EC) sides of the bioreactor. In other embodiments, step 964 may involve circulating various materials to ensure that any cells that may have attached themselves to the inside surface of fibers are released and removed from the bioreactor. As one example, a protease may be added to break down proteins, such as glycoproteins that may aid in binding of the cells to the fibers.

In one embodiment, as part of a harvest process 964, fluid within the bioreactor (e.g., intracapillary space) may be circulated at a relatively high rate. The circulation of the fluid may promote suspension of the cell expanded at step 948. The circulation may occur for a predetermined period of time to ensure that the expanded cells are suspended in the fluid and as many as possible may be recovered from the bioreactor. Flow 900 ends at step 968.

With respect to flows 700, 800, and 900 illustrated in FIGS. 7-9, the operational steps depicted are offered for purposes of illustration and may be rearranged, combined into other steps (e.g., add steps 908 and/or 912 into flows 700 and/or 800), used in parallel with other steps, etc., according to embodiments of the present disclosure. Fewer or additional steps may be used in embodiments without departing from the spirit and scope of the present disclosure. Also, steps (and any sub-steps) may be performed automatically in some embodiments, such as by a processor (1100 (FIG. 11)) executing pre-programmed tasks stored in memory, in which such steps are provided merely for illustrative purposes.

Also, it is noted that although flows 700, 800, and 900 have been described above with various steps in particular order, the present invention is not limited thereto. In other embodiments, the various steps and sub-steps may be performed in a different order, in parallel, partially in the order shown in FIGS. 7-9, and/or in sequence as shown in FIGS. 7-9. Also, the description above indicating that the step or sub-steps are performed by particular features or structures is not intended to limit the present invention. Rather, the description is provided merely for illustrative purposes. Other structures or features not described above may be used in other embodiments to perform one or more of the steps of flows 700, 800, and 900. Furthermore, flows 700, 800, and 900 may include some optional steps. However, those steps above that are not indicated as optional should not be considered as essential to the invention, but may be performed in some embodiments of the present invention and not in others.

Figure 11:
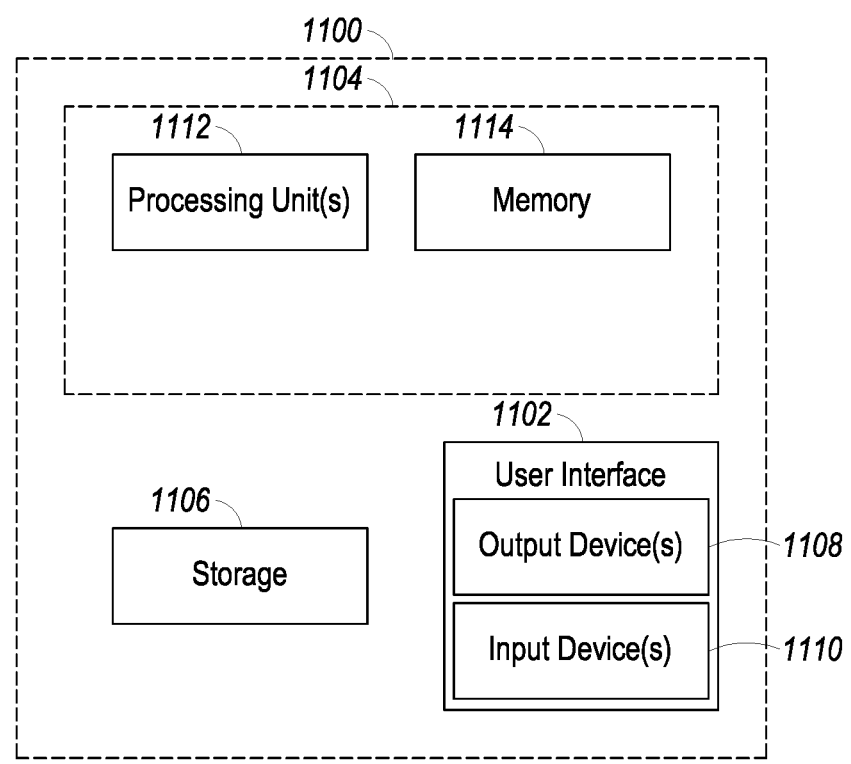
FIG. 11 illustrates components of a computing system that may be used to implement embodiments.

FIG. 11 illustrates example components of a computing system 1100 upon which embodiments of the present disclosure may be implemented. Computing system 1100 may be used in embodiments, for example, where a cell expansion system uses a processor to execute tasks, such as custom tasks or pre-programmed tasks performed as part of processes, such as the process illustrated by flows 700, 800, and 900 and described above.

The computing system 1100 may include a user interface 1102, a processing system 1104, and/or storage 1106. The user interface 1102 may include output device(s) 1108, and/or input device(s) 1110 as understood by a person of skill in the art. Output device(s) 1108 may include one or more touch screens, in which the touch screen may comprise a display area for providing one or more application windows. The touch screen may also be an input device 1110 that may receive and/or capture physical touch events from a user or operator, for example. The touch screen may comprise a liquid crystal display (LCD) having a capacitance structure that allows the processing system 1104 to deduce the location(s) of touch event(s), as understood by those of skill in the art. The processing system 1104 may then map the location of touch events to user interface (UI) elements rendered in predetermined locations of an application window. The touch screen may also receive touch events through one or more other electronic structures, according to embodiments. Other output devices 1108 may include a printer, speaker, etc. Other input devices 1110 may include a keyboard, other touch input devices, mouse, voice input device, etc., as understood by a person of skill in the art.

Processing system 1104 may include a processing unit 1112 and/or a memory 1114, according to embodiments of the present disclosure. The processing unit 1112 may be a general purpose processor operable to execute instructions stored in memory 1114. Processing unit 1112 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits, etc., as understood by a person of skill in the art.

The memory 1114 may include any short-term or long-term storage for data and/or processor executable instructions, according to embodiments. The memory 1114 may include, for example, Random Access Memory (RAM), Read-Only Memory (ROM), or Electrically Erasable Programmable Read-Only Memory (EEPROM), as understood by a person of skill in the art. Other storage media may include, for example, CD-ROM, tape, digital versatile disks (DVD) or other optical storage, tape, magnetic disk storage, magnetic tape, other magnetic storage devices, etc., as understood by a person of skill in the art.

Storage 1106 may be any long-term data storage device or component. Storage 1106 may include one or more of the systems described in conjunction with the memory 1114, according to embodiments. The storage 1106 may be permanent or removable. In embodiments, storage 806 stores data generated or provided by the processing system 104.

EXAMPLES

Some examples that may implement aspects of the embodiments are provided below. Although specific features may be described in these examples, they are provided merely for illustrative and descriptive purposes. The present invention is not limited to the examples provided below.

Example 1

Initial expansion of unselected cord blood-derived (CB) HSCs, CD34+ cells from three (3) donors are acquired from AllCells® (Alameda, CA) by positive immunomagnetic selection of cord blood and grown in co-culture with bone marrow-derived hMSCs under static conditions (5% $CO_2$ & 37.0° C.) with serum-free CellGenix (Freiburg, Germany) CellGro® GMP SCGM with the addition of StemCell2MAX™ supplement (rhFlt-3L, rhSCF, rhTPO, rhGlial-derived neurotrophic factors) at a 1:100 concentration to develop the inoculum for a hollow fiber cell expansion system, e.g., the Quantum® Cell Expansion System (CES). Each of the Quantum CES bioreactors is coated with five (5) mg of human fibronectin overnight and seeded with unmatched hMSCs at $3.0 \times 10^3/cm^2$ five (5) days in advance of HSC introduction. The bioreactors are seeded with CB-derived CD34+ cells in CellGro® GMP SCGM+ StemCell2MAX at a cell density of $3.0 \times 10^4$/mL for a total seeding of $5.7 \times 10^6$ cells and subsequently expanded for 6.6 days using a mixed gas (5% $CO_2$, 20% $O_2$, balance $N_2$) at 37.0° C. in co-culture. Cells are seeded to the bioreactor, expanded, and harvested using automated tasks on the Quantum® CES. Specifically, cells are grown in the intracapillary loop of the bioreactor and base media additions are made through the extracapillary loop of the system in order to enhance hMSC-CB CD34+ cell interactions. Metabolites are quantified daily with Abbott i-STAT® analyzers. Cells are counted with a Beckman Coulter Vi-CELL™ XR Cell Viability Analyzer using a diameter size range of 5-50 μm. Harvested cells are stained for surface biomarkers with BD Mouse Anti-Human CD34-FITC, BD Mouse Anti-Human CD34-PE, BD Mouse Anti-Human CD38-APC, MB CD133/1-PE, and eBioscience Fixable Viability Dye eFluor® 780 and analyzed by flow cytometry using a BD FACSCanto II equipped with BD FACSDiva software. Fluorescent microscopy images are captured with a Zeiss Axio Observer A1 microscope equipped with ZEN pro software. The Stem Cell Technologies Human CFU Methocult™ Assay is used to induce the differentiation of harvested CB-derived CD34+ cells.

TABLE 1

CB-derived CD34+ Cell Seeding and Harvest Cell Numbers

| CES System Yield CES Run | Bioreactor Seeding | Bioreactor Harvest | Vi-CELL Viability | Fold Increase | Expansion Days | DS | DT (hrs) |
|---|---|---|---|---|---|---|---|
| Donor 1 | $5.70 \times 10^6$ | $7.95 \times 10^7$ | 83.8% | 13.9 | 6.6 | 3.8 | 41.7 |
| Donor 2 | $5.70 \times 10^6$ | $9.94 \times 10^7$ | 85.1% | 17.4 | 6.6 | 4.1 | 38.4 |
| Donor 3 | $5.70 \times 10^6$ | $8.89 \times 10^7$ | 89.2% | 15.6 | 6.6 | 4.0 | 40.0 |
| Average | $5.70 \times 10^6$ | $8.93 \times 10^7$ | 86.0% | 15.7 | 6.6 | 4.0 | 40.0 |

Figure 12:
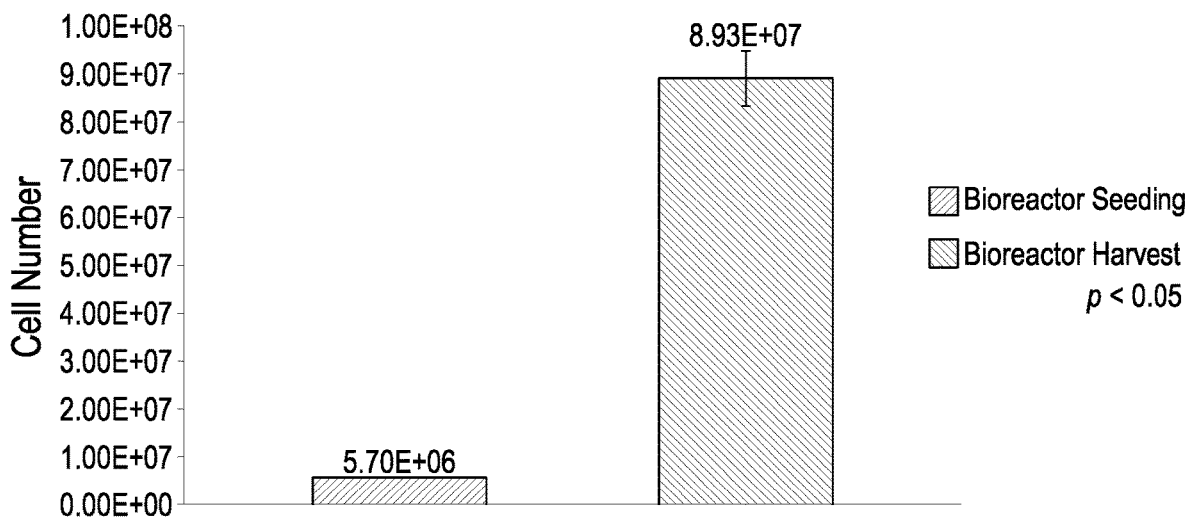
FIG. 12 illustrates a bar graph of the number of cells grown according to one embodiment for expansion of CD34+ cells in a bioreactor system.
Figure 13:
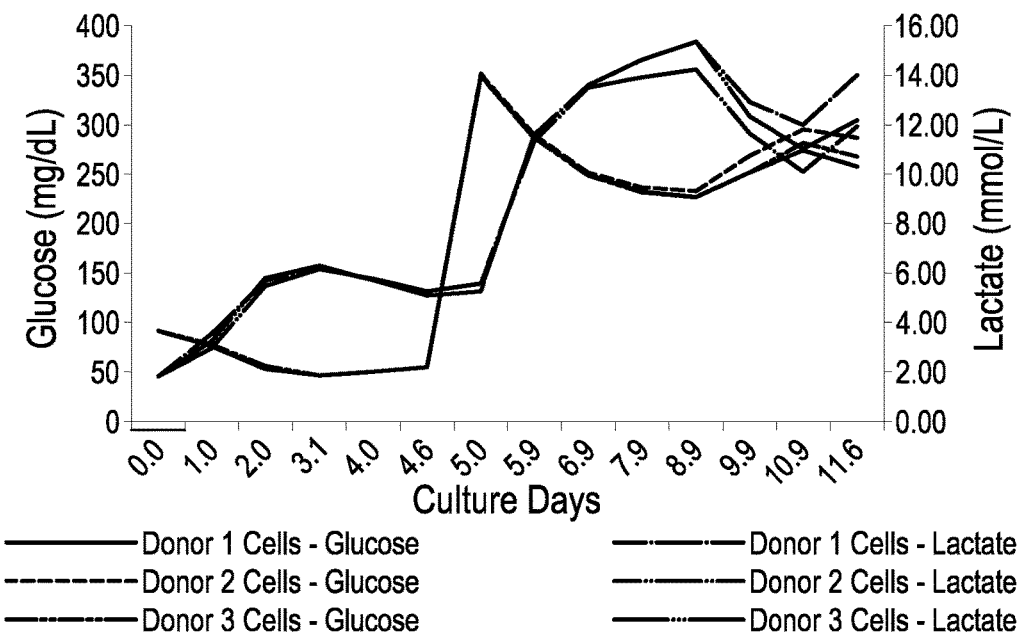
FIG. 13 illustrates a graph showing metabolic profile according to one embodiment for expansion of CD34+ cells.
Figure 14:
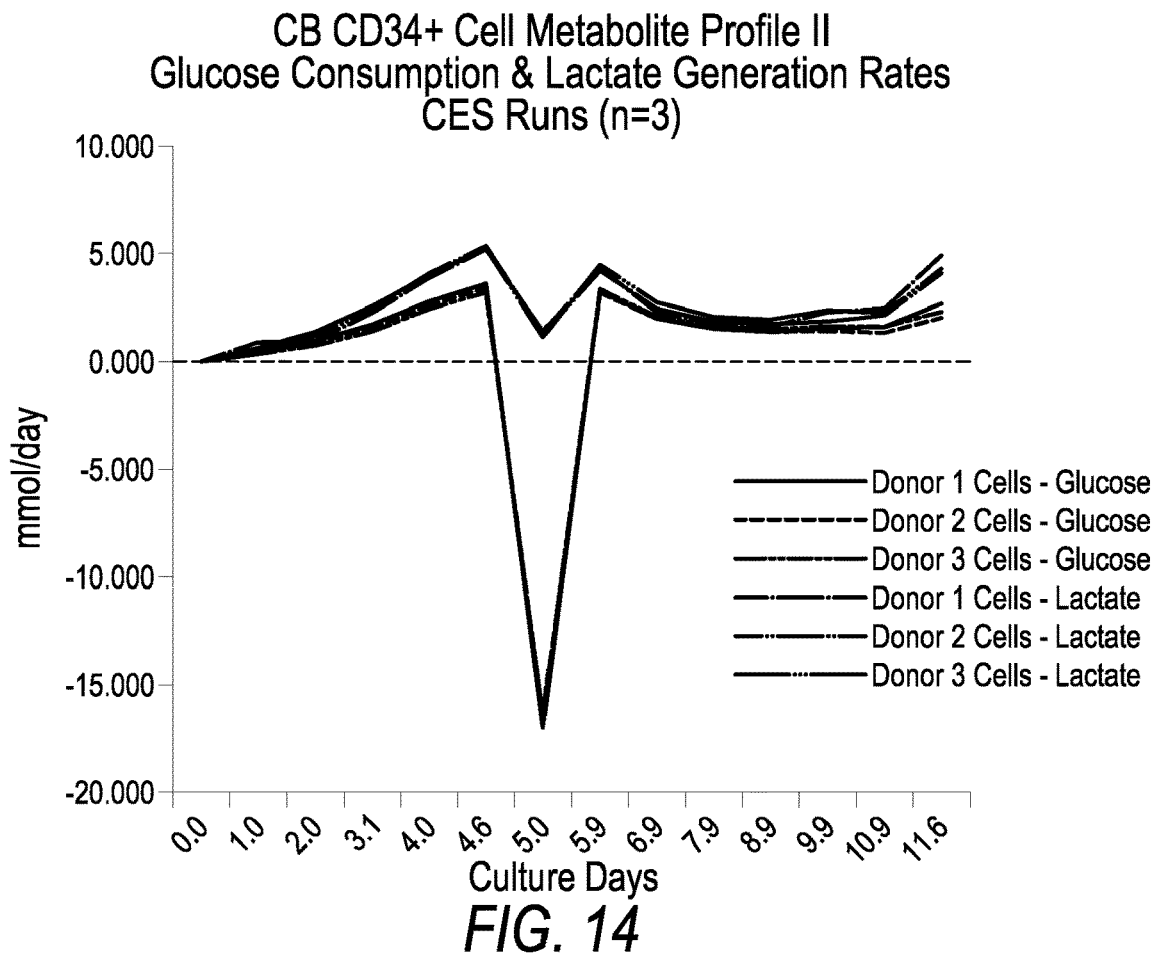
FIG. 14 illustrates a graph showing metabolic rates according to one embodiment for expansion of CD34+ cells.

FIG. 12 illustrates a bar graph of some of the data shown above in Table 1, namely showing the average number of cells harvested from the various donors. FIG. 13 illustrates a graph showing metabolic profile for the various donors. FIG. 14 illustrates a graph showing metabolic rates for the various runs.

The results may suggest that the Quantum CES hollow fiber membrane bioreactor can support the expansion of CB-derived CD34+, CD38-CD133+ progenitor cells in co-culture using an automated CES. The growth factor supplement of rhFlt-3L, rhSCF, rhTPO, rhGlial-derived neurotrophic factors may support the co-culture of CB-derived CD34+ lineage cells. Expanded CB-derived CD34+ cells may demonstrate lineage differentiation in the presence of appropriate cytokines and supplements (SCF, GM-CSF, IL-3, GSF, EPO). Table 2 below provides a summary of flow cytometry results.

TABLE 2

Summary Of Flow Cytometry Results

| Quantum Run | CD34+CD38− | CD34+CD38+/− | CD34+CD133+ |
|---|---|---|---|
| Donor 1 | 4.3% | 4.9% | 1.0% |
| Donor 2 | 5.1% | 6.8% | 2.5% |
| Donor 3 | 4.3% | 7.3% | 0.8% |
| Average | 4.6% | 6.3% | 1.4% |

Example 2

The culture of I-Mag selected human HSC CB CD34+ cells (frozen CB008F-2) obtained from AllCells using IMDM media supplemented with FBS or human AB serum in mono- or co-culture with human mesenchymal stem cells (hMSCs) to improve the media cost framework of CD34+ expansion is explored. Cell culture devices include the Wilson G-Rex 10 Gas Permaeable Membrane devices and conventional tissue culture polystyrene flasks. After the results of the first experiment, a decision is made to switch to a StemSpan SPEM II media containing modified IMDM (BSA, rh-insulin, transferrin) plus FBS or Human Serum AB as well as to increase the cell seeding density in order to improve cell growth and biomarker expression.

Experiment 1

T25 TCPS Flasks are seeded with hMSC-P2T1 at 1,000 cells/cm$^2$ in Gibco alpha-MEM (Cat. No. 32561-037) Complete Medium (CM224), incubated at 37° C. (5% $CO_2$), and grown to 80% confluency on Day-6 prior to seeding with thawed CB CD34+ cells. By comparison, no hMSCs are seeded into the Wilson G-Rex gas permeable cell culture device. CB CD34+ cells are seeded at a concentration of 2.0×10$^4$/mL and grown with 7 mL of Gibco IMDM (Cat. No. 31980-030), 20% HyClone FBS (Cat. No. 5H30070.03) or 18% Akron HS-AB (Cat. No. AK9340-0100), plus Gibco Penicillin/Streptomycin/Neomycin antibiotics (Cat. No. 15640-055) for four (4) days. The CD34+ cell seeding density is based on a recommendation to maintain the cell concentration below 3.0×10$^4$/mL. Culture vessels are weighed to determine culture volumes and cell counts are captured with a calibrated Beckman Coulter Vi-Cell XR Cell Viability Analyzer on Days 0, 2, and 4.

Experiment 2

Six (6) T25 TCPS Flasks are seeded with hMSC-P2T1 at 8.48×10$^3$/cm$^2$ in Gibco alpha-MEM Complete Medium (CM231), incubated at 37° C. (5% $CO_2$), and grown to 80% confluency on Day-3 prior to seeding with thawed (37° C.) CB CD34+ cells (AllCells CB-CD34+, Cat. No. CB008F-2, ID No. CBP140129C). CB CD34+ cells (2.5 mL) are resuspended in 22.5 mL of StemSpan SFEM II media, centrifuged at 500xg for 7 minutes, resuspended in 10 mL of respective complete media, and counted with a calibrated Beckman Coulter Vi-Cell NR Cell Viability Analyzer. Each flask media is exchanged with 6 mL of sterile filtered (Corning 0.22 µm PES) StemSpan SFEM II Complete Media 20% FBS (HyClone Cat. No. 5H30070.03) or 20% HS-AB (Innovative Research (Cat. IPLA-SERAB-OTC-16138), Gibco Pennicillin/Streptomycin/Neomycin Antibiotics (Cat. No. 15640-055). A total of four (4) T25 co-culture flasks are seeded with CB CD34+ cells at 3.00×10$^4$/mL or 3.00×10$^5$/mL into 6 mL per flask with StemSpan SFEM II media supplemented with either 20% FBS or 20% HS-AB, incubated at 37° C. (5% $CO_2$) for four (4) days. Suspension cells from each flask are removed on Day-2, transferred to a 15 mL sterile centrifuge tube, centrifuged at 500xg for 7 minutes, resuspended in 6 mL of their respective Complete StemSpan SFEM II media, and returned to T25 co-culture flasks for incubation. On Day-4, images of suspension cells are captured by phase-contrast photomicroscopy (Olympus CKX41 with QCapture Pro 6.0 software), flasks are weighed to determine flask volume, and cells are counted as previously described. Aliquots (1.25×10$^5$ cells) of the high cell seeding density are prepared for flow cytometry staining (BD Pharmingen FITC Mouse Anti-human CD34 Cat. 555821, BD Pharmingen FITC Mouse IgG1K isotype control Cat. 555748, BD Pharmingen APC Mouse Anti-human CD38 Cat. 555462, BD Pharmingen Mouse IgG1K Isotype Control Cat. 555751, BD Pharmingen PE Mouse Anti-human CD34 Cat. 555822, BD Pharmingen PE Mouse IgG1K Isotype Control Cat. 555749, Miltenyi Biotec CD133/1-PE Cat. 180-080-801) using a modified version of the Flow Cytometry Prep Protocol. Flow data are acquired and analyzed without fixative using a BD FACSCanto® II flow cytometer equipped with BD FACSDiva® v6.1.3 software.

Experiment 1 may evaluate the mono- and co-culture of cord blood derived CD34+ cells at the low seeding density of 2.00×10$^4$/mL in a total volume of 7 mL using IMDM base media supplemented with 20% FBS or 18% HS. T25 tissue culture polystyrene (TCPS) flasks and gas permeable G-Rex-10 vessels are used as the primary static culture environment.

Figure 15:
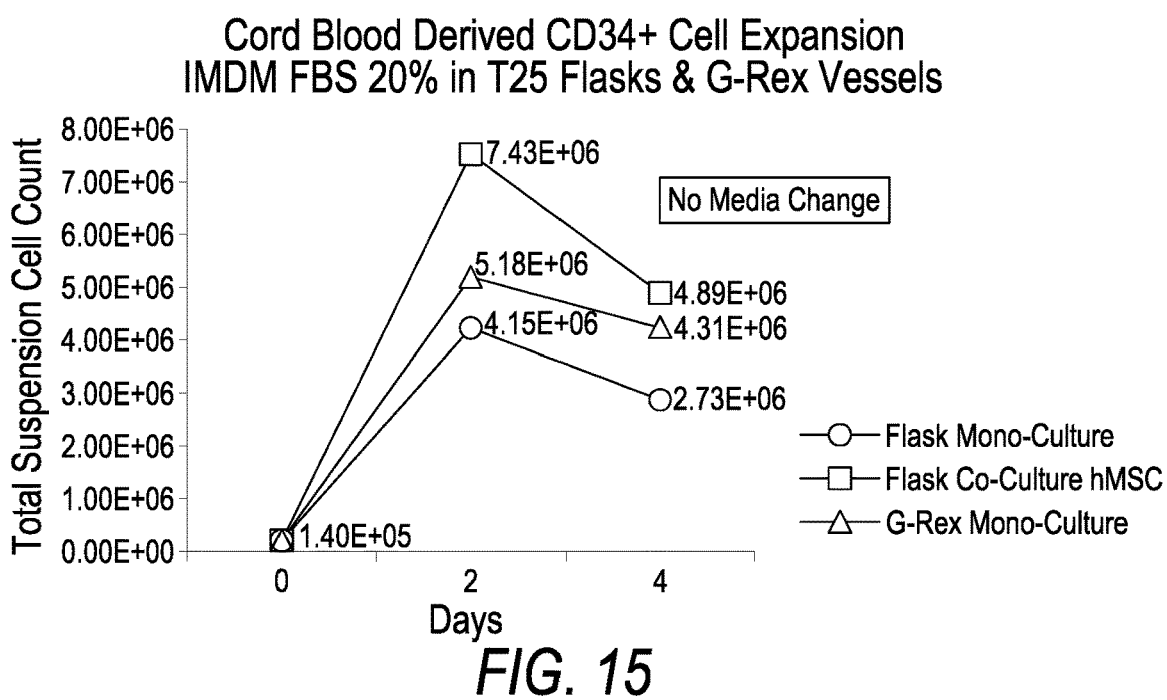
FIG. 15 illustrates a graph showing cell counts according to one embodiment for expansion of CD34+ cells.
Figure 16:
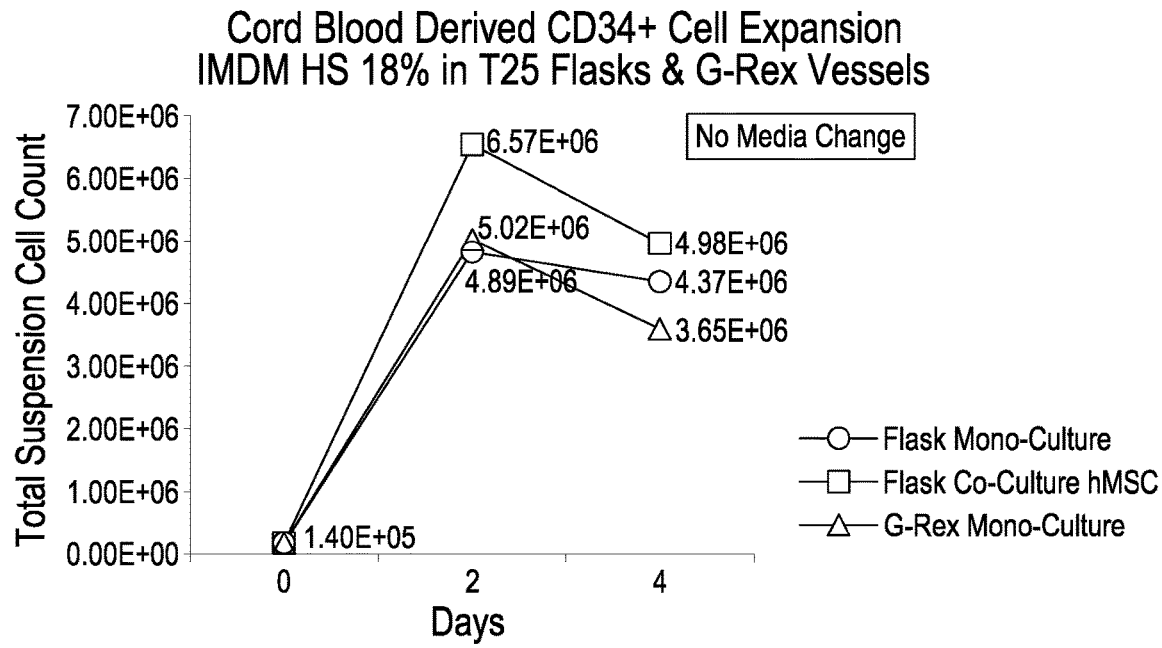
FIG. 16 illustrates a graph showing cell counts according to another embodiment for expansion of CD34+ cells.

FIG. 15 illustrates a graph showing cell counts from Experiment 1 with FBS. FIG. 16 illustrates a graph showing cell counts from Experiment 1 with Human Serum.

Both the FBS and HS supplemented IMDM demonstrate an increase in cell count by Day-2. However, there is also a decrease in cell concentration by Day-4. There is also reduction in cell membrane integrity from Day-2 to Day-4 in both of the supplemented media from 87% to 76.4% with FBS and from 88.5% to 76.3% with HS. In our case, this may be due to the lack of a media change on Day-3 or the low cell seeding density of 2.00×10$^5$/mL. In summary, the 20% FBS supplemented media may generate a 7.5-7.6 fold-increase in flask co-culture, 7.1 fold-increase in flask mono-culture, and a 7.0-7.2 fold-increase in the G-Rex-10 mono-culture by Day-4. By comparison, the 18% HS supplemented media may generate a 7.3-7.5 fold-increase in flask co-culture, 6.8 fold-increase in flask mono-culture, and a 6.7-6.9 fold-increase in the G-Rex10 mono-culture by Day-4.

Figure 17:
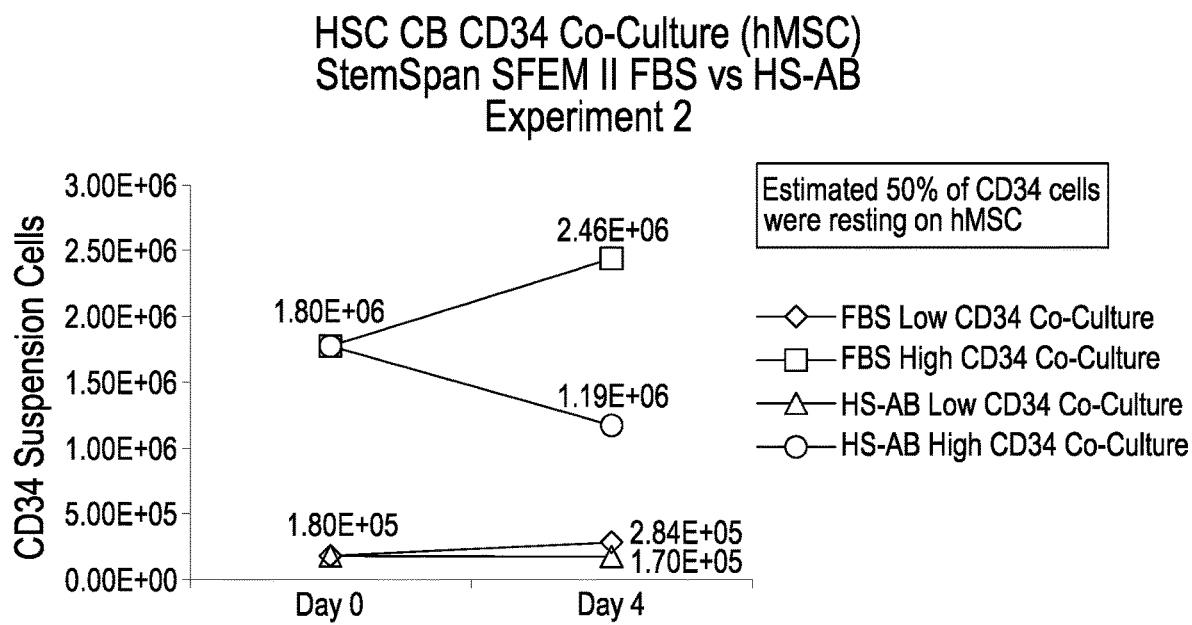
FIG. 17 illustrates a graph showing cell counts according to another embodiment for expansion of CD34+ cells.

Experiment 2 may evaluate both low and high seeding densities. FIG. 17 illustrates a graph showing CD34+ cells in both low and high seeding density conditions. Both the low (3.00×10$^4$/mL) and high (3.00×10$^5$/mL) CB CD34+ cell seeding density in 6 mL of StemSpan SFEM II supplemented with 20% FBS may generate an increase of suspension cell count on Day-4 of 57% and 36% respectively. In contrast, the 20% HS-AB supplemented media may generate a reduced suspension cell count over the same time 4-day culture period.

Figure 18:
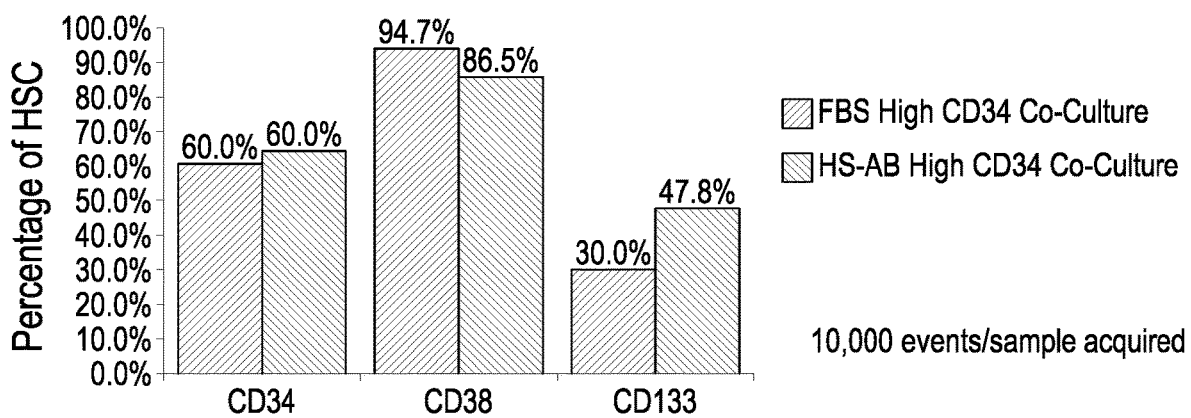
FIG. 18 illustrates a bar graph showing different types of biomarkers on cells grown according to embodiments.

FIG. 18 illustrates a bar graph showing flow cytometry results. These flow cytometry results suggest that the majority of the CD34+ cells may also express the CD38+ biomarker in either the FBS or HS-AB supplemented media at the high cell seeding condition. The CD38 biomarker may be indicative of early progenitor CD34+ cell populations. More mature CD34+ cells may gradually become CD38 low/—during expansion in short-term culture after Day-4. CD133+CD34+ blood progenitor cells may be putitive markers of platelet engraftment in patients undergoing autologous peripheral blood stem cell transplantation. These data also indicate that the FBS and HS-AB supplemented media may support a CD133+ cell subpopulation, 30% and 47% respectively, in static co-culture.

Example 3

Below is an example of a protocol that may be used in embodiments. The protocol indicates possible modification from a conventional protocol(s) utilized when using a cell expansion system (CES).

CES Cell Load Modification 3—Load with Circ. Distribution & Rotation

A conventional Pre-selected MSC Expansion Protocol, may be performed with the following modifications shown in combined bold, underline, and italics below. Rotate the bioreactors 180 degrees and allow the cells to settle to the top of the hollow fiber membrane (HFM) for 5 minutes.

Then rotate the bioreactor back to the "home" horizontal position and proceed with the expansion protocol. The rationale for the modification is to distribute the cells over the entire surface area of the bioreactor hollow fiber (FIGS. 10A-D).

Day 0: Attach Feeder Cells with Rotation

Purpose: enables adherent cells to attach to the bioreactor membrane while allowing flow on the EC circulation loop. The pump flow rate to the IC loop is set to zero.

Prior to loading the cells into all a CES with Distribution and Rotation, install a Custom Task using the following existing/modified steps: Config>Task via the touch screen display or GUI. These solutions and corresponding volumes are based on the either default or modified settings for these custom tasks.

TABLE 3

Solutions for Attaching Cells, Modification
Table 3: Solutions for Attach Cells

| Bag | Solution in Bag | Volume |
|---|---|---|
| Cell Inlet | None | N/A |
| Reagent | None | N/A |
| IC Media | *Media with FBS or Serum-Free* | 6 mL/hour |
| Wash | None | N/A |
| EC Media | None | N/A |

TABLE 4 hMSC Feeder Layer Loading & Seeding
Table 4: Custom 3 Task Settings to Load hMSCs

| Setting | Step 1 | Step 2 | Step 3 | Step 4 | Step 5 |
|---|---|---|---|---|---|
| IC Inlet | Cell | IC Media | None | None | IC Media |
| IC Inlet Rate | *25* | *25* | *0.00* | 0.00 | 0.1 |
| IC Circulation Rate | *150* | *150* | *200* | 0.00 | 20 |
| EC Inlet | None | None | None | IC Media | None |
| EC Inlet Rate | 0.00 | 0.00 | 0.00 | 0.1 | 0.00 |
| EC Circulation Rate | 30 | 30 | 30 | 30 | 30 |
| Outlet | EC Waste | EC Waste | EC Waste | EC Waste | IC Waste |
| Rocker Control | In Motion: (−90° to 180°) | In Motion: (−90° to 180°) | In Motion: (−90° to 180°) | Stationary: *180°* | Stationary: 0° |
| Stop Condition | Empty Bag | IC Volume: 22 mL | *Time: 2 min* | *Time: 1,440 min* | Manual: |
| Estimated Fluid | Unknown | <0.1 L | Unknown | <0.2 L | Unknown |
| Omit or Include | Include | Include | Include | Include | Include |

Return to conventional cell feeding tasks on Day 2 or as needed and continue with the pre-cultured hMSC expansion protocol using Feed Cells Task.

Day 5: Introduce CB CD34+Suspension Cells with Rotation

IC/EC Exchange & Condition Media for CB CD34+ Cells.

Attach SCGM Base Media to IC Media line. Perform IC/EC Washout and Condition Media Tasks respectively.

Attach Cell Inlet bag with CB CD34+ cell suspension of SCGM (98 mL)+StemCell2MAX 100X supplement (2 mL) to Cell Inlet line of the System with a sterile welder.

TABLE 5

CB CD34+ Cell Loading & Seeding
Table 5: Custom Task 7 Settings to Load CB CD34+ Suspension Cells

| Setting | Step 1 | Step 2 | Step 3 | Step 4 |
|---|---|---|---|---|
| IC Inlet | Cell | IC Media | None | None |
| IC Inlet Rate | *25* | *25* | *0.00* | 0.00 |
| IC Circulation Rate | *150* | *150* | *200* | 0.00 |
| EC Inlet | None | None | None | IC Media |
| EC Inlet Rate | 0.00 | 0.00 | 0.00 | 0.1 |
| EC Circulation Rate | 30 | 30 | 30 | *60* |
| Outlet | EC Waste | EC Waste | EC Waste | *EC Waste* |
| Rocker Control | In Motion: (−90° to 180°) | In Motion: (−90° to 180°) | In Motion: (−90° to 180°) | Stationary: 0° |
| Stop Condition | Empty Bag | IC Volume: 22 mL | Time: 2 min | Manual: |
| Estimated Fluid | Unknown | <0.1 L | Unknown | Unknown |
| Omit or Include | Include | Include | Include | Include |

Resuspension of Cells Prior to Harvest

The purpose of this Circulation Task is to resuspend those cells that may be attached to the hMSC feeder layer during co-culture prior to initiating the Harvest Task.

TABLE 6

Circulation and Resuspension of Cells
Table 6: Custom Task 1 Settings to Resuspend Settled CB CD34+ Cells

| Setting | Step 1 |
| --- | --- |
| IC Inlet | *None* |
| IC Inlet Rate | *0* |
| IC Circulation Rate | *200* |
| EC Inlet | *None* |
| EC Inlet Rate | *0* |
| EC Circulation Rate | *60* |
| Outlet | *EC Waste* |
| Rocker Control | *In Motion: (-90° to 180°) Dwell Time: 1 sec* |
| Stop Condition | *Time: 2 min* |
| Estimated Fluid | Unknown |
| Omit or Include | Include |

Harvest
CES Harvest Task with Modification.

TABLE 7

Harvest, Modification
Table 7: Harvest, Modified

| Setting | Step 1 |
| --- | --- |
| IC Inlet | IC Media |
| IC Inlet Rate | 400 |
| IC Circulation Rate | −70 |
| EC Inlet | *IC Media* |
| EC Inlet Rate | 60 |
| EC Circulation Rate | 30 |
| Outlet | Harvest |
| Rocker Control | In Motion: (−90° to 180°) Dwell Time: 1 sec |
| Stop Condition | IC Volume: 378 mL |
| Estimated Fluid | IC Media: 0.5 L |
| Omit or Include | Include |

It will be apparent to those skilled in the art that various modifications and variations can be made to the methods and structure of the present invention without departing from its scope. Thus it should be understood that the present invention is not be limited to the specific examples given. Rather, the present invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the present invention.

What is claimed is:

1. A method of expanding cells, the method comprising:
    coating with fibronectin an intracapillary side of a plurality of hollow fibers extending through a bioreactor;
    introducing human mesenchymal stem cells (hMSCs) into the plurality of hollow fibers coated with fibronectin by activating a pump to pump the hMSCs into the plurality of hollow fibers, stopping the pump to allow a first portion of the hMSCs to attach to a first area of an inside of the plurality of hollow fibers coated with fibronectin, rotating the bioreactor 180° from an initial start position, reactivating the pump to circulate a second portion of the hMSCs within the hollow fibers, and stopping the pump to allow the second portion of the hMSCs to attach to a second area of the inside of the hollow fibers coated with fibronectin that is opposite to the first area;
    culturing the hMSCs in a first media;
    introducing a first plurality of cells comprising CD34+ cells into the plurality of hollow fibers and rotating the bioreactor to form a co-culture of CD34+ cells and hMSCs,
    wherein the first plurality of cells is added to the hollow fiber bioreactor without purification;
    exposing the co-culture of CD34+ cells and hMSCs to a second media, which is a growth media including a soluble combination of recombinant FMS-like tyrosine kinase 3 ligand (rhFlt-3L), recombinant human stem cell factor (rhSCF), recombinant thrombopoietin (rhTPO), and recombinant human glial cell-derived neurotrophic factor (rhGDNF);
    expanding at least a portion of the first plurality of cells in the plurality of hollow fibers of the bioreactor to generate a second plurality of expanded cells by circulating nutrients including glucose the growth media through an extracapillary side of the hollow fiber bioreactor; and
    removing the second plurality of expanded cells from the bioreactor.

2. The method of claim 1, wherein the first plurality of cells is derived from cord blood.

3. The method of claim 1, wherein the human mesenchymal stem cells are bone marrow derived.

4. The method of claim 3, further comprising:
    administering the second plurality of expanded cells to a patient to reconstitute hematopoiesis in the patient.

5. The method of claim 1, further comprising:
    flushing the hollow fiber bioreactor with a washing fluid prior to introducing the first plurality of cells.

6. The method of claim 1, wherein expanding the first plurality of cells comprises controlling an environment of the hollow fiber bioreactor.

7. The method of claim 6, wherein controlling the environment of the hollow fiber bioreactor comprises:
    monitoring at least one parameter within the hollow fiber bioreactor; and
    adjusting the at least one parameter to keep the at least one parameter within an acceptable range.

8. The method of claim 7, wherein adjusting the at least one parameter comprises controlling a flow rate of the growth media flowing through the extracapillary side of the hollow fiber bioreactor.

* * * * *